US012702629B2

(12) United States Patent
Wong et al.

(10) Patent No.: US 12,702,629 B2
(45) Date of Patent: Aug. 11, 2026

(54) EVAPORATION STRATEGY GENERATED ANTIBACTERIAL ENAMEL-LIKE FLUORAPATITE-POLYACRYLIC ACID SHEET FOR FUNCTIONAL DENTAL RESTORATION

(71) Applicant: The University of Hong Kong, Hong Kong (CN)

(72) Inventors: Hai Ming Wong, Hong Kong (CN); Quan Li Li, Heifei (CN); Le Zhang, Hong Kong (CN)

(73) Assignee: The University of Hong Kong, Hong Kong (CN)

( * ) Notice: Subject to any disclaimer, the term of this patent is extended or adjusted under 35 U.S.C. 154(b) by 779 days.

(21) Appl. No.: 18/053,856

(22) Filed: Nov. 9, 2022

(65) Prior Publication Data

US 2023/0141188 A1 May 11, 2023

Related U.S. Application Data

(60) Provisional application No. 63/263,784, filed on Nov. 9, 2021.

(51) Int. Cl.

*A61K 6/887* (2020.01)
*A61C 5/20* (2017.01)
*A61K 6/20* (2020.01)
*A61K 6/69* (2020.01)
*A61K 6/838* (2020.01)

(52) U.S. Cl.

CPC ................ *A61K 6/887* (2020.01); *A61C 5/20* (2017.02); *A61K 6/20* (2020.01); *A61K 6/69* (2020.01); *A61K 6/838* (2020.01)

(58) Field of Classification Search

CPC ................................ A61K 6/838; A61K 6/887
See application file for complete search history.

(56) References Cited

U.S. PATENT DOCUMENTS 3,873,327 A * 3/1975 Duff ......................... A61K 6/69 106/35
9,005,587 B2 4/2015 LeGeros et al.

FOREIGN PATENT DOCUMENTS

CN 108144119 B 2/2021

OTHER PUBLICATIONS

Anastasiou, A.D., et al., "Antibacterial properties and regenerative potential of Sr2+ and Ce3+ doped fluorapatites; a potential solution for peri-implantitis," Scientific Reports, 2019, 9(14469):1-11.
Shanmugam, S., et al., "Copper substituted hydroxyapatite and fluorapatite: Synthesis, characterization and antimicrobial properties," Ceramics International, 2014, 40:15655-15662.
Alhilou, A., et al., "Physicochemical and Antibacterial Characterization of a Novel Fluorapatite Coating," ACS Omega, 2016, 1:264-276.
Stanic, V., et al., "Synthesis, structural characterisation and antibacterial activity of Ag+-doped fluorapatite nanomaterials prepared by neutralization method," Applied Surface Science, 2015, 337:72-80.

* cited by examiner

*Primary Examiner* — Wenwen Cai
(74) *Attorney, Agent, or Firm* — SALIWANCHIK, LLOYD & EISENSCHENK

(57) ABSTRACT

The subject invention pertains to an evaporation strategy combined with low-molecular-weight polyacrylic acid (LPAA) to generate an antibacterial dental enamel-like structure. Polystyrene (PS) plates can be used as a removable substrate for the continuous growth of fluorapatite (FAP). The FAP-LPAA composition can be used to kill microorganisms. The LPAA contained dental enamel-like FAP provides an alternative to prevent secondary caries if a carious cavity is filled with shaped dental enamel-like FAP-LPAA.

12 Claims, 68 Drawing Sheets

EVAPORATION STRATEGY GENERATED ANTIBACTERIAL ENAMEL-LIKE FLUORAPATITE-POLYACRYLIC ACID SHEET FOR FUNCTIONAL DENTAL RESTORATION

CROSS-REFERENCE TO RELATED APPLICATION

The subject application claims the benefit of U.S. Provisional Application Ser. No. 63/263,784, filed Nov. 9, 2021, which is incorporated herein by reference in its entirety.

BACKGROUND

Dental enamel can be destroyed by caries or mechanical abrasion after tooth eruption and the subsequent disappearance of ameloblasts. This process is irreversible and as such, the degraded enamel cannot be self-regenerated. Without dental treatment, the enamel caries or abrasion may lead to a deep lesion in dentin that increases the risk of pulp inflammation or pulp exposure.

Many studies have utilized metals, ceramics, or polymers as therapeutic adjuncts for the replacement of decayed enamel or filled lesion sites. Resins or composite resins are one of the most commonly used agents. However, the main disadvantage is that they generally are prone to shrinkage, which generates stress, leads to microleakage at the resin-enamel interface, and increases the likelihood of secondary caries caused by bacteria-meditated demineralization process. The applied materials simulating the properties of enamel currently available in the market are not fully effective given their different compositions and microstructures compared to natural enamel. These chemical differences between foreign materials and native enamel result in different mechanical properties and issues in compatibilities, such as the abrasion of resin or enamel when the resin is in contact with enamel or when the enamel is in contact with ceramics. These compatibility issues and the necessity of new materials that better simulate native enamel have given rise to research investigating the regeneration of enamel-like material.

The reproduction of enamel-like structures requires that the material is in densely packed, needle-like, rod-like or fiber-like crystal structures. While some promising reports have shown that a thin layer of enamel-like hydroxyapatite can be regenerated onto a demineralized enamel surface with the ability to recover early caries lesions, its translation into the clinical setting is impractical given that the processes described are onerously time-consuming and that at the clinical level. Enamel-like materials are needed at a bulk scale to fulfill the requirements of the clinic.

Meanwhile, preventing caries caused by acidogenic and aciduric bacteria is also a focus in dentistry. Although some antibacterial agents can be applied on the tooth surface, their activity can be significantly buffered by saliva, and their efficacy may be reduced by tooth brushing or antibiotic resistance.

Therefore, there remains a need for the fabrication of an enamel-like structure with sustainable antibacterial activity for dental restorations.

BRIEF SUMMARY

The subject invention pertains to an enamel-like structure composed of fluorapatite (FAP) and low-molecular-weight polyacrylic acid (LPAA) that can be used in methods to treat dental restoration. The anionic polymer, LPAA, can regulate the balance between nucleation and the crystal growth of FAP and can improve the mechanical properties of enamel-like structure via the bonding effect among the adjacent crystals by carboxy group. In certain embodiments, the crystals form a prism-like structure. The composition comprising FAP-LPAA can prevent and/or reduce the proliferation of bacteria on the enamel-like structure surface. In certain embodiments, *Streptococcus mutans* on the FAP-LPAA surface could be killed within 12 hours. LPAA is safe for human beings. Thus, LPAA can be used as a useful additive when antibacterial enamel-like FAP was generated for dental restoration.

BRIEF DESCRIPTION OF DRAWINGS

(FIGS. 1A-1D) FAP surface at the 1st day, surface at the 3rd day, fracture surface at the 3rd day, and fracture surface at the 30th day, respectively; (FIG. 1E) schematic diagram of FAP at different stages; (FIGS. 1A-1J) FAP-LPAA surface at the 1st day, surface at the 3rd day, fracture surface at the 3rd day, and fracture surface at the 30th day, respectively; and (Be) schematic diagram of FAP-LPAA at different stages. Scale Bar: (Aa) 10 μm; (Ab) 50 μm; (Ac) 40 μm; (Ad) 15 μm; (Ba) 500 nm; (Bb) 200 nm; (Bc) 100 nm; (Bd) 5 μm FIGS. 2A-2D. Characterization of FAP-LPAA. (FIG. 2A) 100 nm.

(FIG. 3A) SEM micrograph of enamel surface; (FIG. 3B) SEM micrograph of enamel cross-section; (FIG. 3C) SEM micrograph of FAP-LPAA surface; (FIG. 3D) SEM micrograph of FAP-LPAA cross-section; (FIG. 3E) EDS at the cross-section of FAP-LPAA; (FIG. 3F) HRTEM micrograph of enamel; (FIG. 3G) HRTEM of FAP-LPAA; (FIG. 3H) water contact angel of dental enamel, dentin, FAP and FAP-LPAA; (FIG. 3I) surface zeta potential of dental enamel, dentin, FAP and FAP-LPAA; and (FIG. 3J) concentration of calcium and phosphorus in demineralization solution.

Scale Bar: (FIG. 3A) 500 nm; (FIG. 3B) 1 μm; (FIG. 3C) 500 nm; (FIG. 3D) 1 μm; (FIGS. 3F-3G) 2 nm.

(FIG. 4A) Load-displacement curves of dental enamel, dentin, FAP, and FAP-LPAA; (FIG. 4B) hardness and Young's modulus of dental enamel, dentin, FAP, and FAP-LPAA; (FIG. 4C) coefficient of friction and wear depth of dental enamel, dentin, FAP, and FAP-LPAA; (FIG. 4D) worn surfaces of dental enamel; (FIG. 4E) worn surfaces of dentin; (FIG. 4F) worn surfaces of FAP; and (FIG. 4G) worn surfaces of FAP-LPAA. Scale Bar: (FIGS. 4D-4G) 100 μm; (zoomed in of FIG. 4D; FIG. 4E; FIG. 4G) 2 μm; (zoomed in of FIG. 4F) 1 μm.

(FIGS. 6A-6F) *S. mutans* at the concentration from $10^8$ to $10^3$ CFU cultured in BHI solution; and (FIGS. 6G-6L) *S. mutans* at the concentration from $10^8$ to $10^3$ CFU cultured in BHI solution containing 2 mg $mL^{-1}$ LPAA. Scale bars: 50 μm.

(FIG. 7A) $10^4$ CFU $mL^{-1}$ *S. mutans* in BHI solution containing 5 mg $mL^{-1}$ LPAA; (FIG. 7B) $10^4$ CFU $mL^{-1}$ *S. mutans* in BHI solution containing 2.5 mg $mL^{-1}$ LPAA; (FIG. 7C) $10^4$ CFU $mL^{-1}$ *S. mutans* in BHI solution containing 1.25 mg $mL^{-1}$ LPAA; (FIG. 7D) $10^4$ CFU $mL^{-1}$ *S. mutans* in BHI solution containing 0.625 mg $mL^{-1}$ LPAA; (FIG. 7E) $10^4$ CFU $mL^{-1}$ *S. mutans* in BHI solution containing 0.3125 mg $mL^{-1}$ LPAA; and (FIG. 7F) $10^4$ CFU $mL^{-1}$ *S. mutans* in BHI solution containing 0 mg $mL^{-1}$ LPAA. Scale bars: 50 μm.

(FIG. 8A) dentin; (FIG. 8B) enamel; (FIG. 8C) HA; and (FIG. 8D) FAP-LPAA. The green color indicates live bacteria while the red color indicates dead bacteria. Scale bars: 50 μm.

(FIGS. 9A-9C) cells in enamel group for 1st, 3rd, and 5th day, respectively; (FIGS. 9D-9F) cells in dentin group for 1st, 3rd, and 5th day, respectively; (FIGS. 9G-9I) cells in FAP-LPAA group for 1st, 3rd, and 5th day, respectively; and (FIGS. 9J-9L) cells in FAP group for 1st, 3rd, and 5th day, respectively. (FIG. 9M) Cell viability of SD-BMSCs from the 1st to the 5th day. Scale bars: 100 μm FIG. 10. Schematic illustration of the mineralization process and photograph of the generated translucent FAP-LPAA sheet. Polydopamine activated polystyrene (PS) substrate in calcification solution was provided with additional buoyancy force by plastic foam, keeping it at a constant distance of 3 mm from the surface of the liquid surface. High temperature (70° C.) triggered evaporation accelerated the enrichment of ions between the substrate and liquid surface. The activated surface provided nucleation sites for mineralization, and a steady stream of ions combined with organic molecules from the calcification solution below the PS substrate provided the building blocks for crystal growth. The growth time and thickness of the generated FAP-LPAA sheet were 30 days and 100 μm. Scale bars: 1 cm

DETAILED DESCRIPTION

Figure 1A:
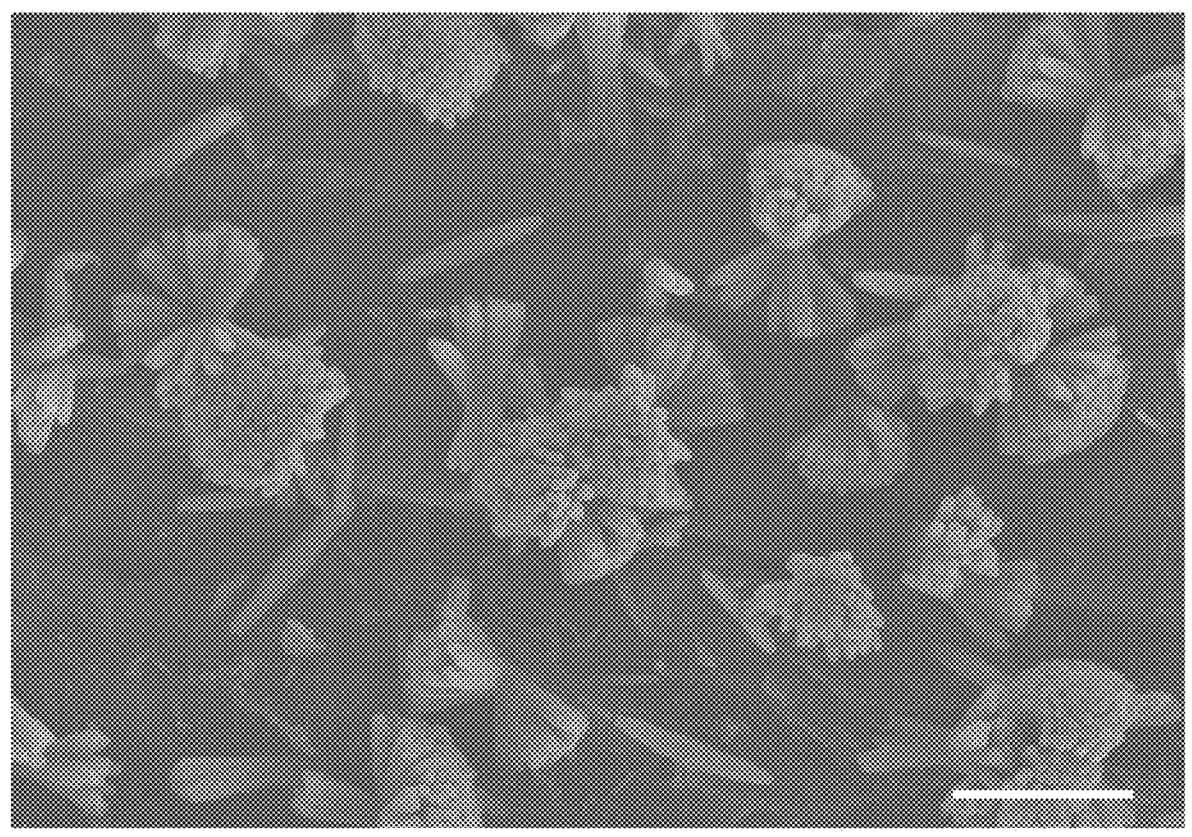
FIGS. 1A-1J. SEM morphology and growth mechanism of FAP and FAP-LPAA.
Figure 1B:
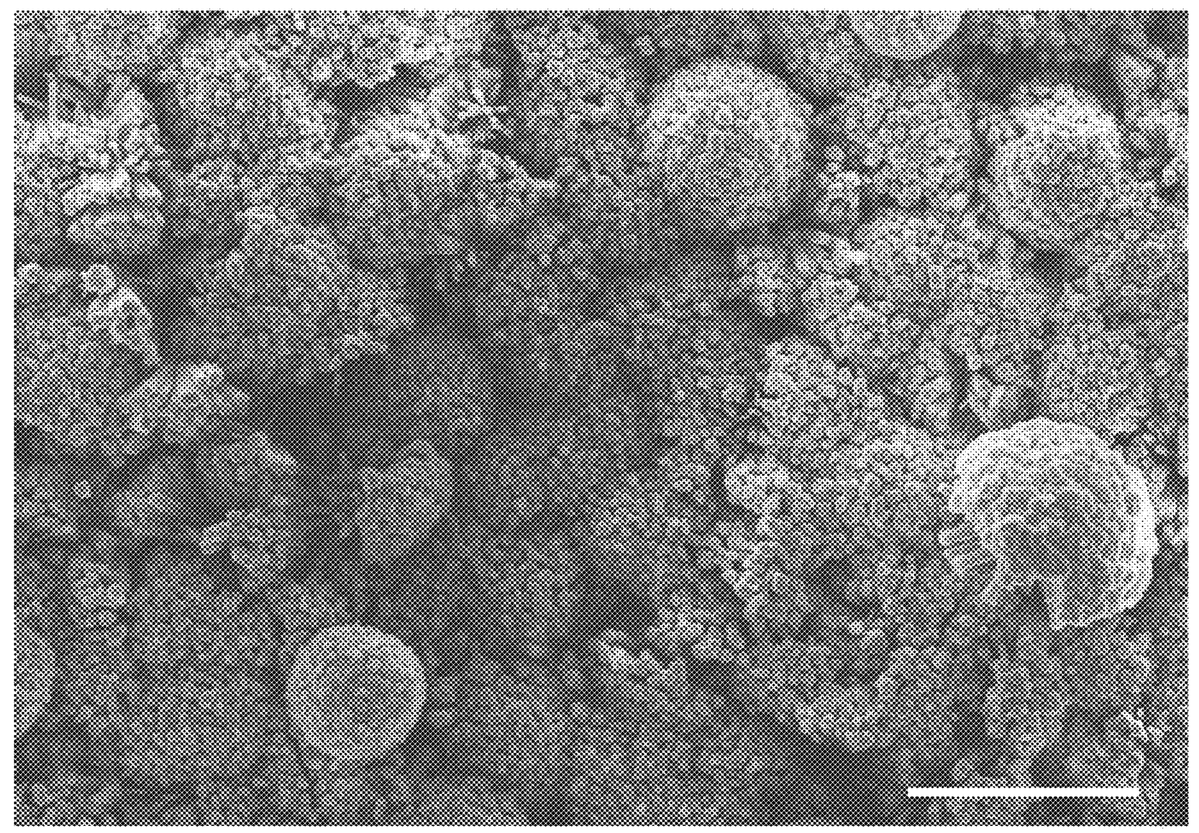
Figure 1C:
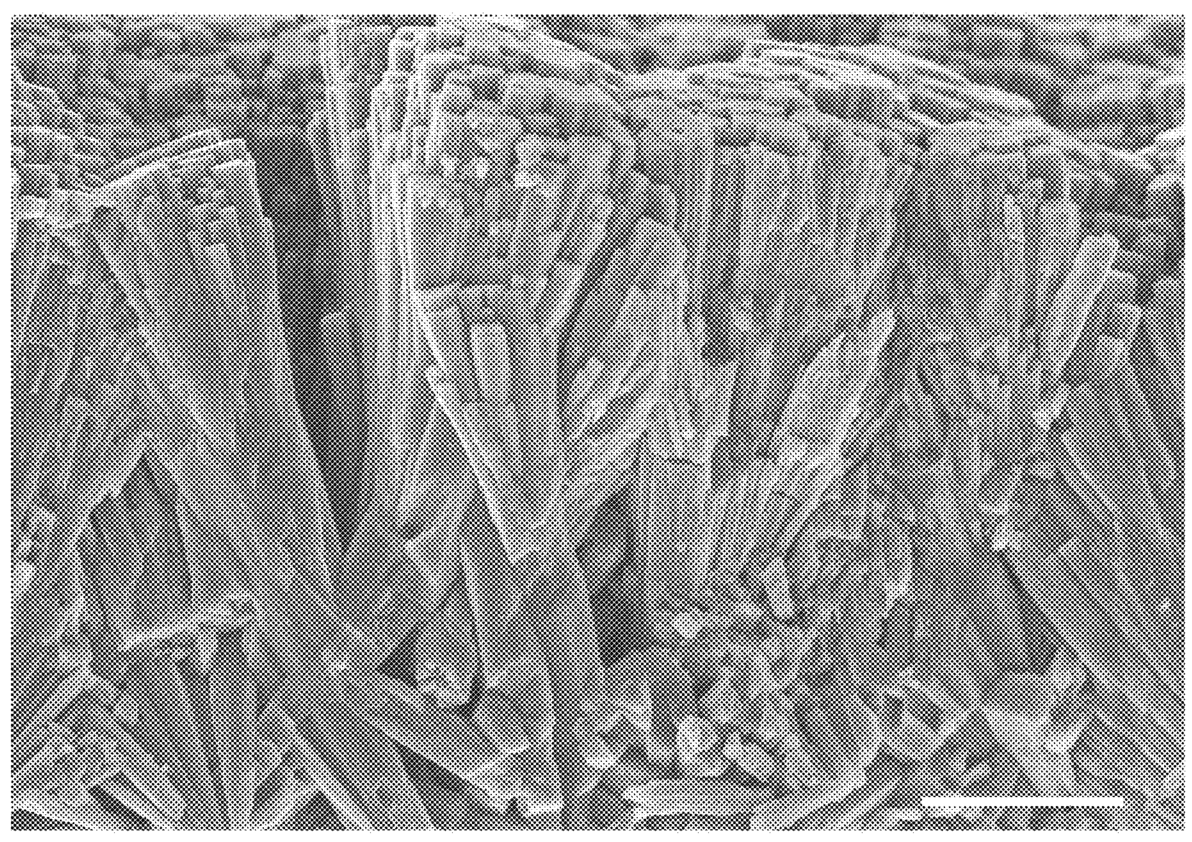
Figure 1D:
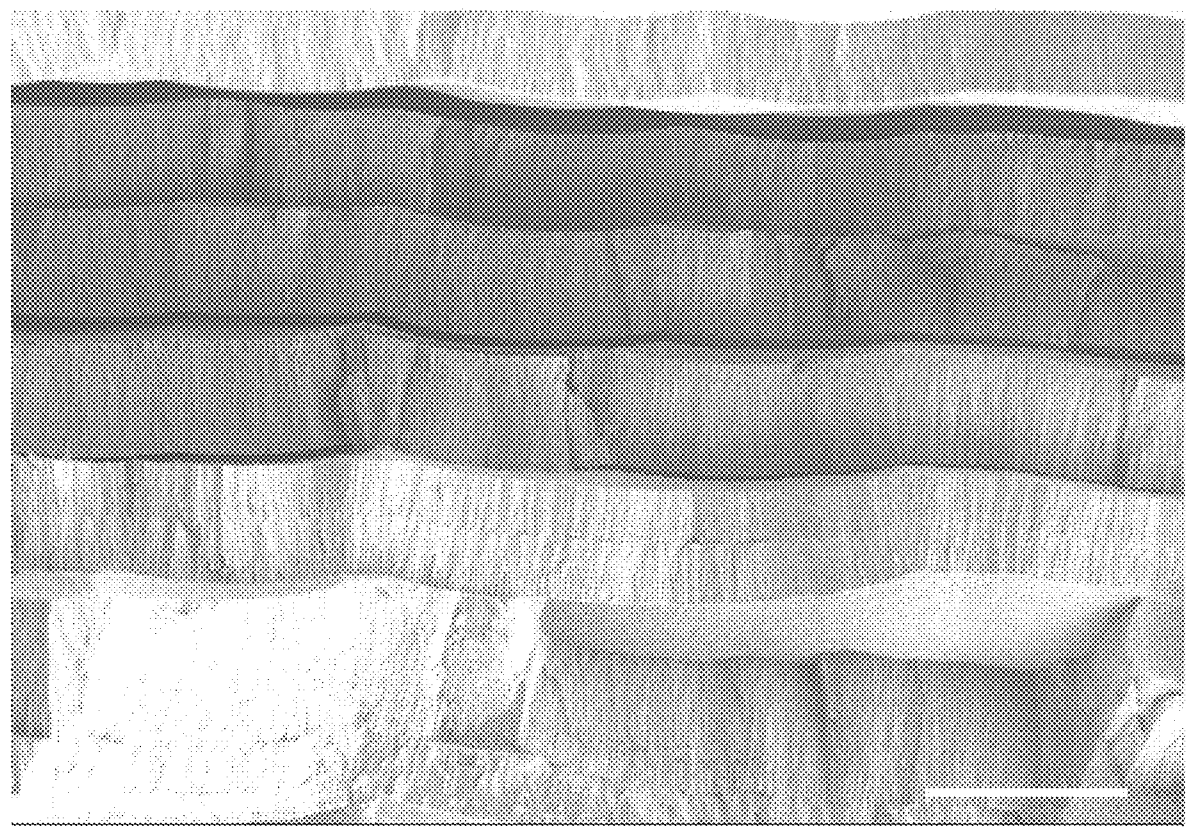
Figure 1E:
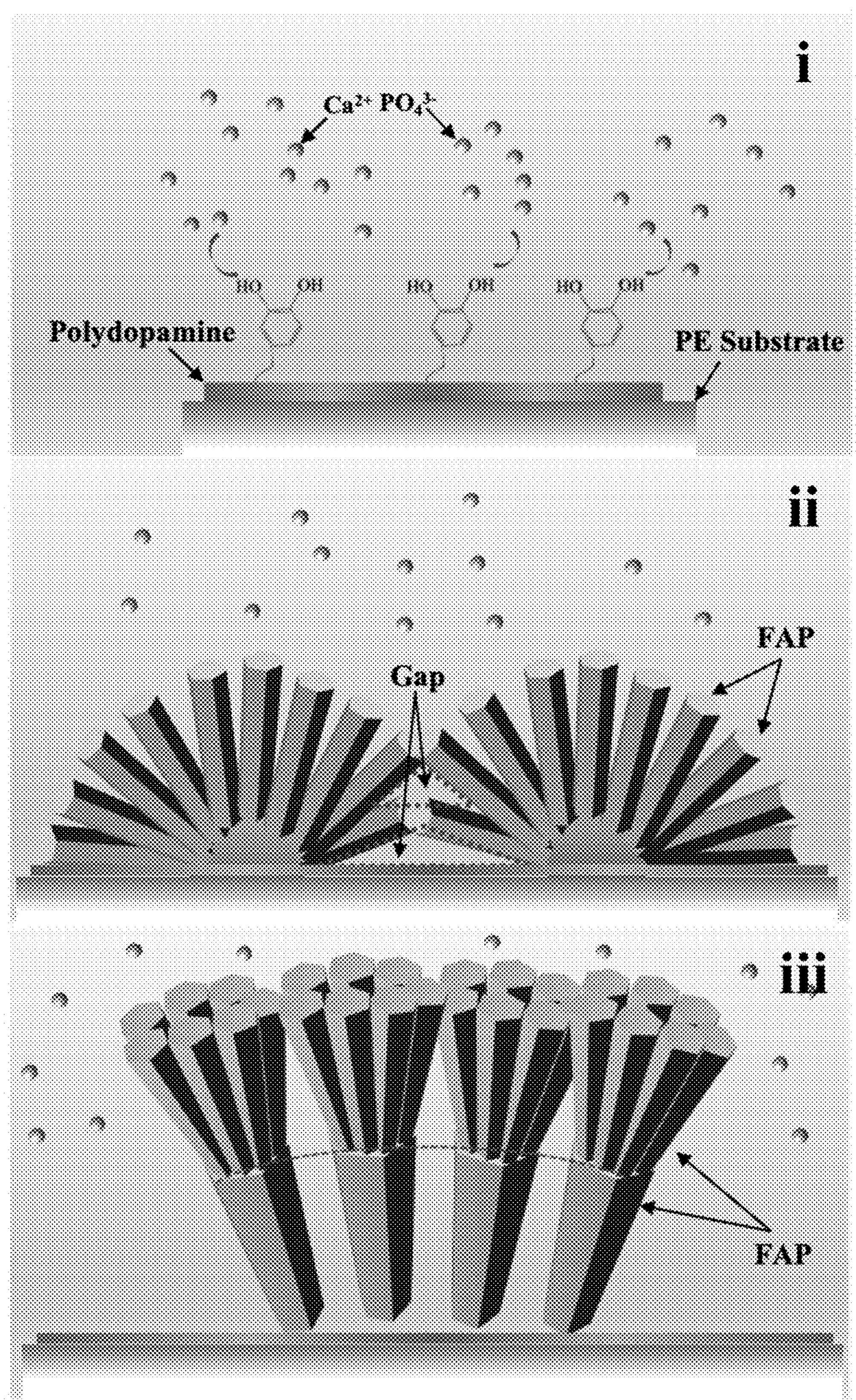
Figure 1F:
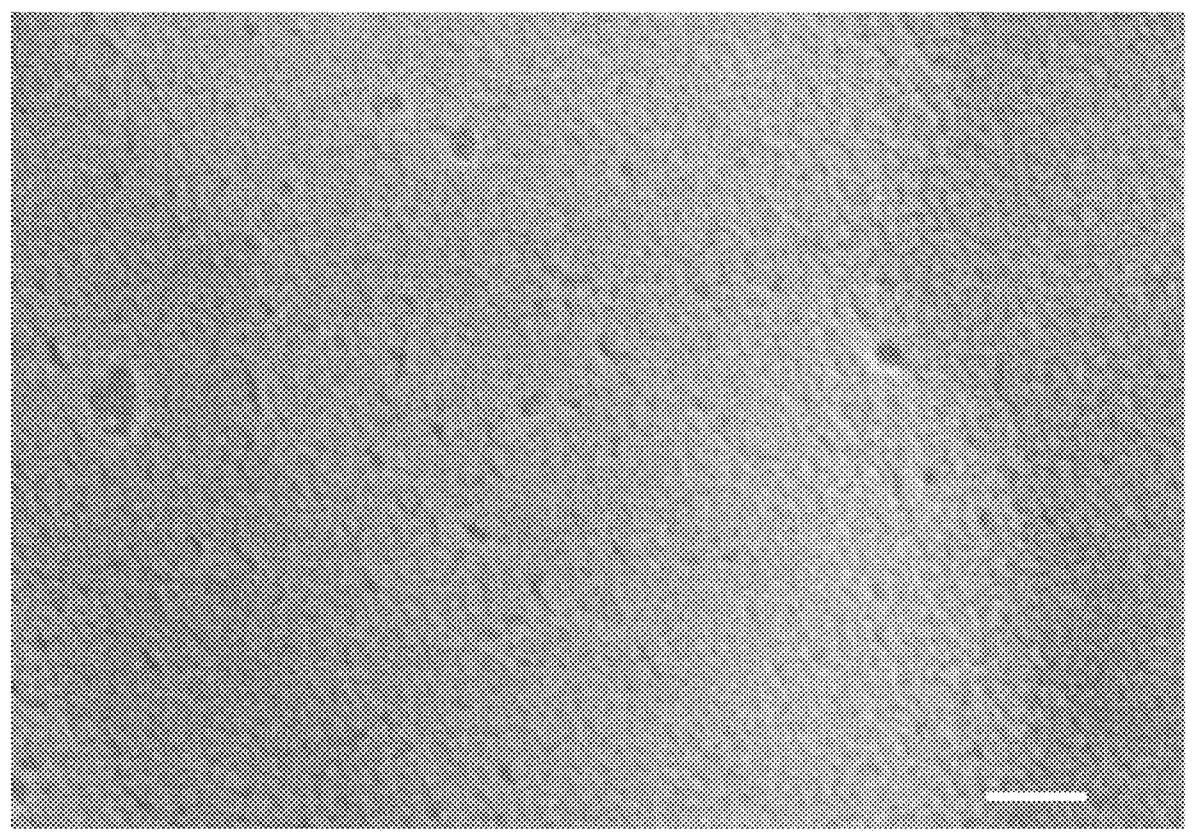
Figure 1G:
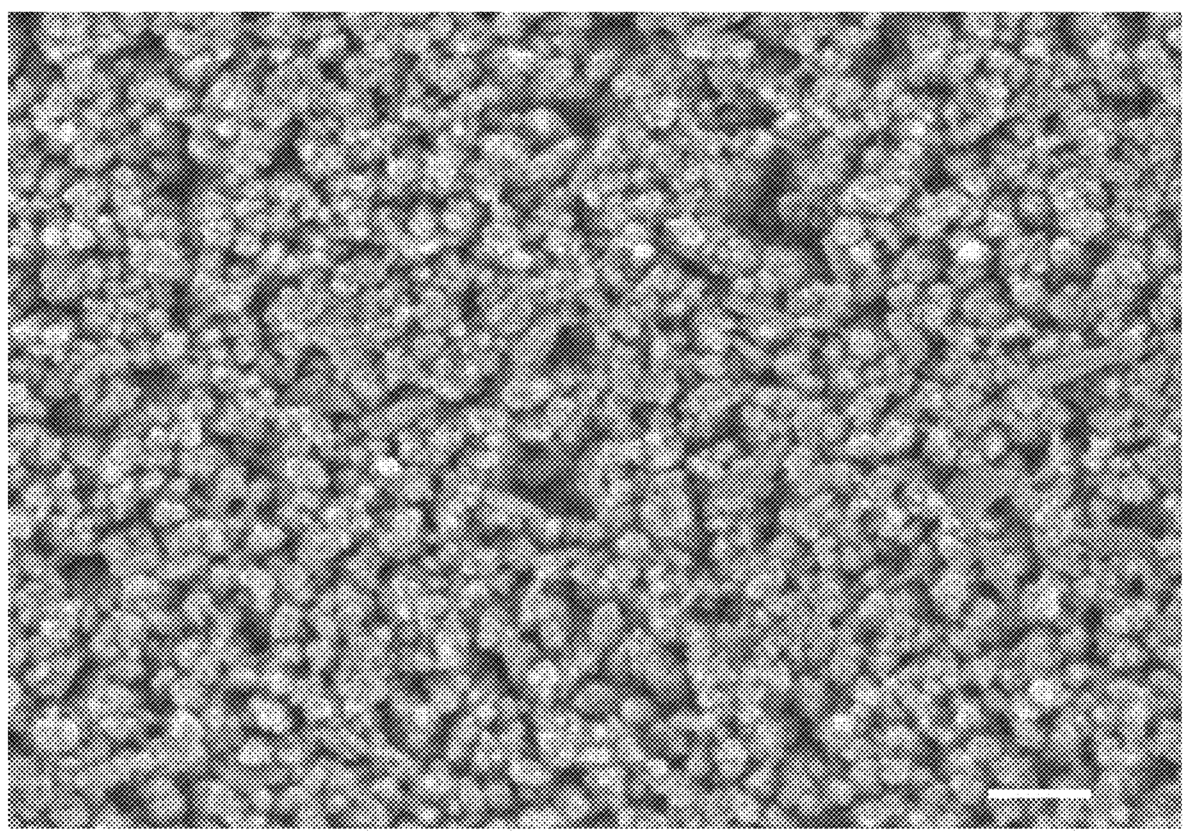
Figure 1H:
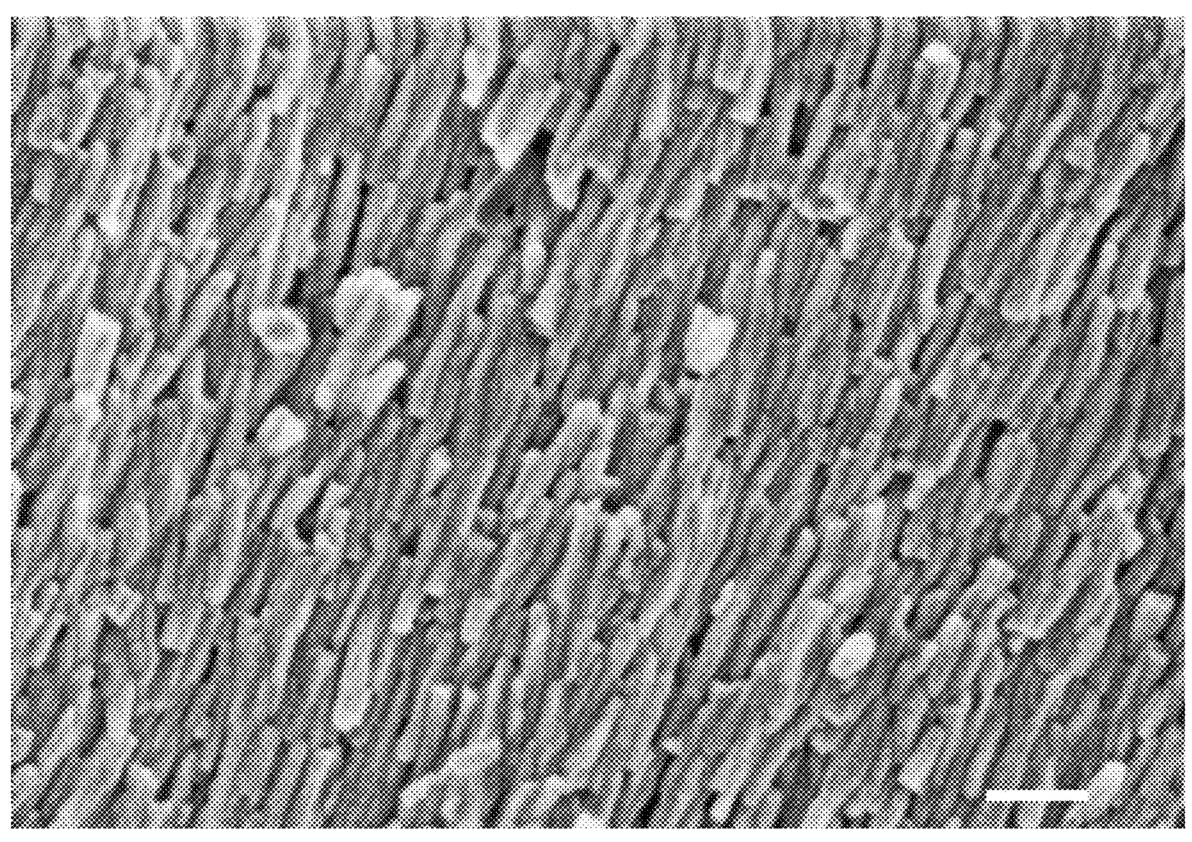
Figure 1I:
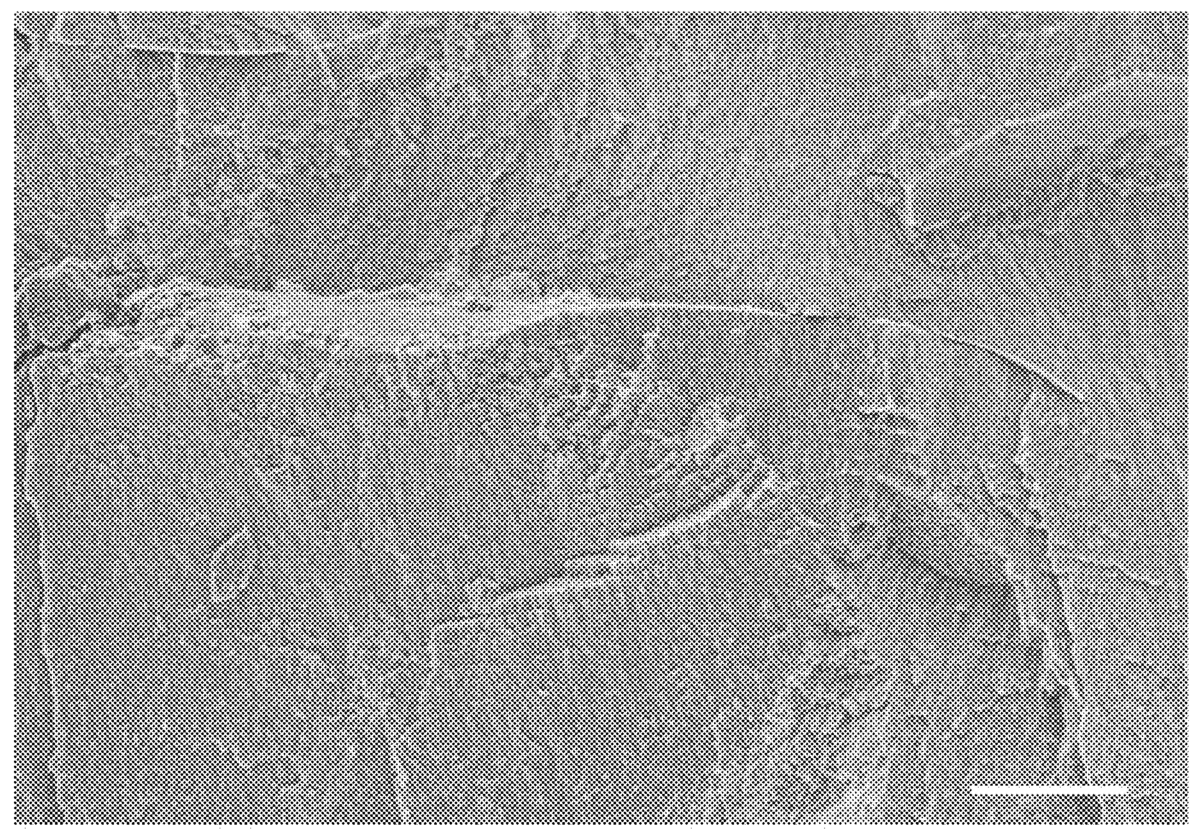
Figure 1J:
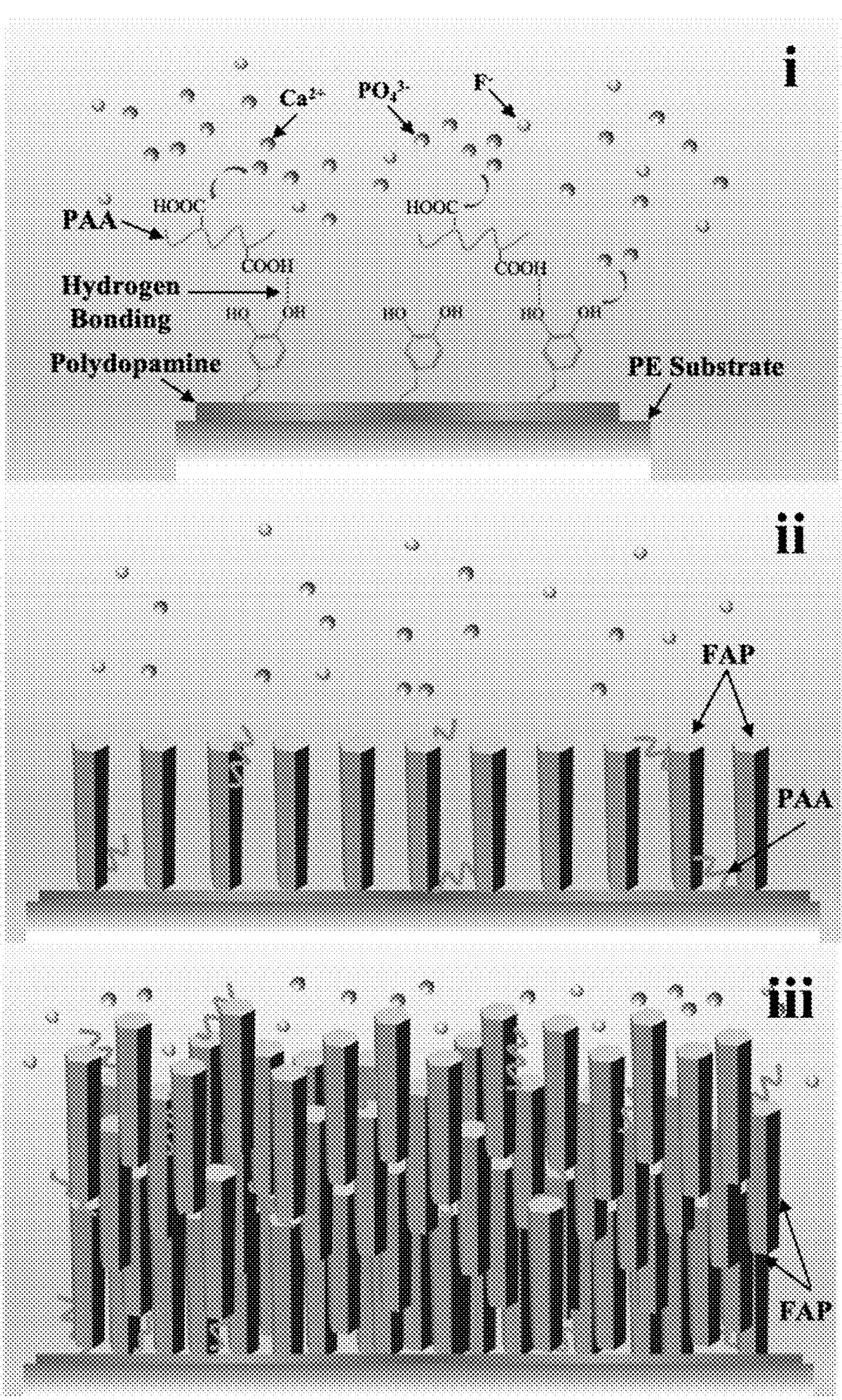
Figure 2A:
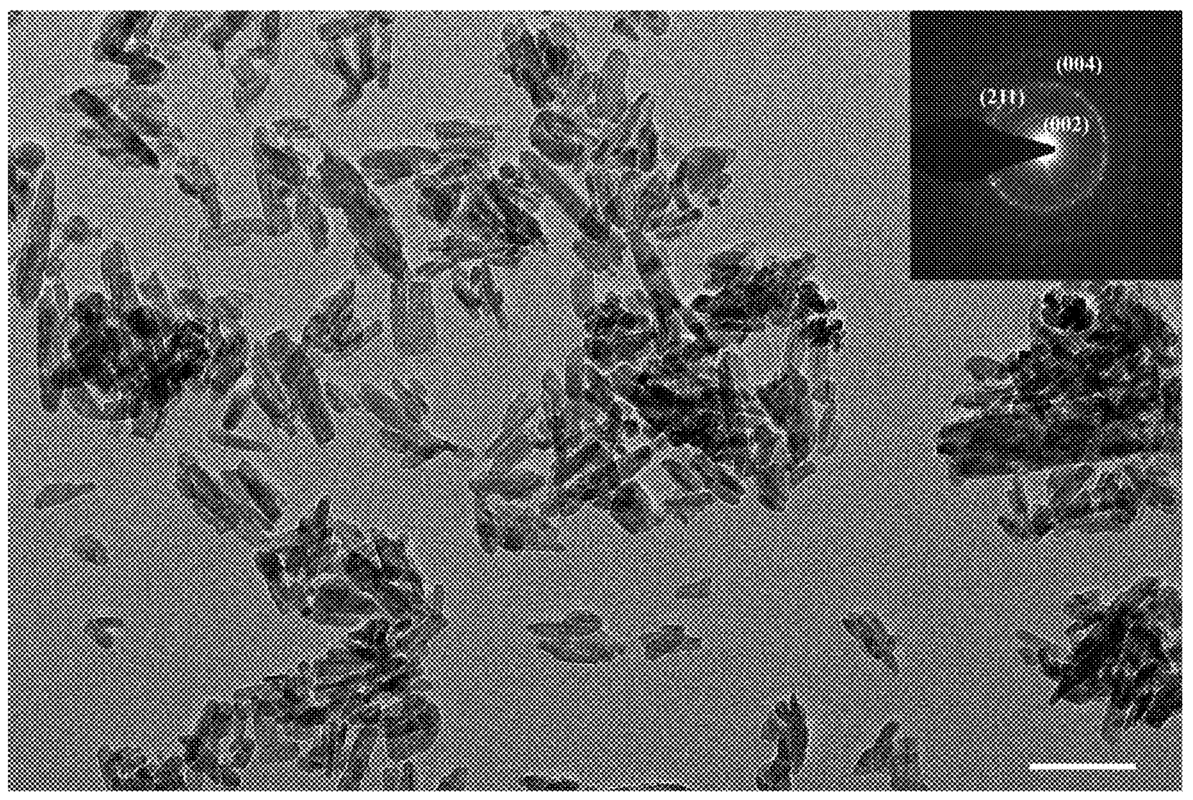
(FIG. 2A) TEM micrograph and SAED of FAP-LPAA.
Figure 2B:
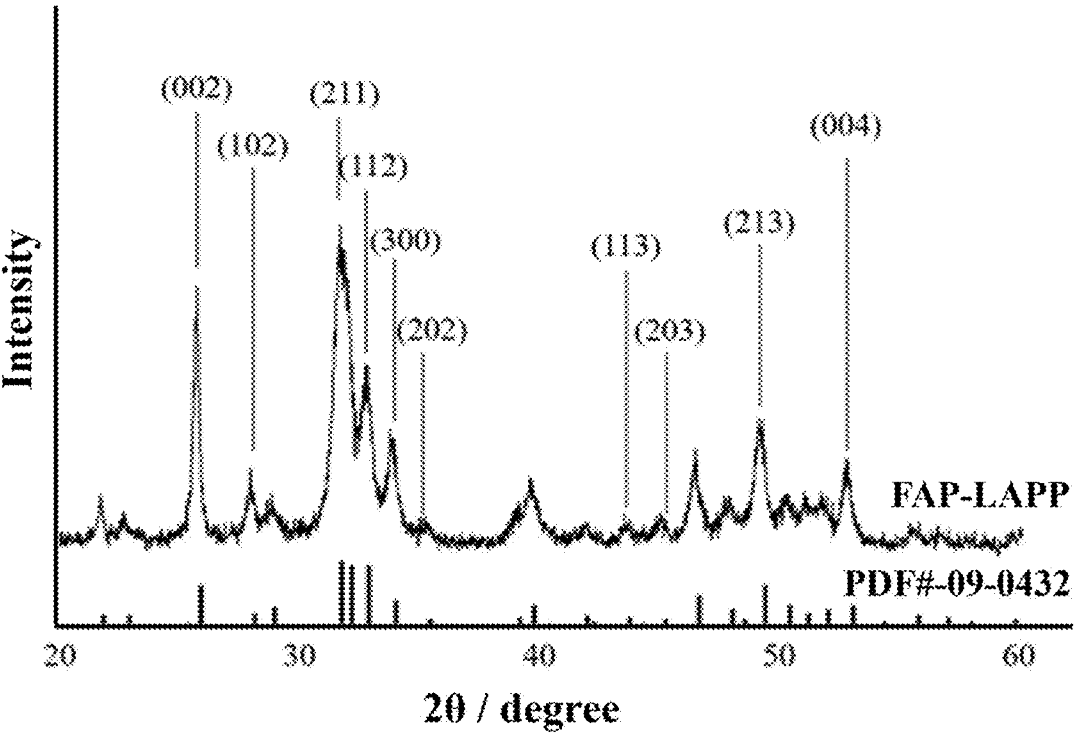
(FIG. 2B) XRD spectrum of FAP-LPAA.
Figure 2C:
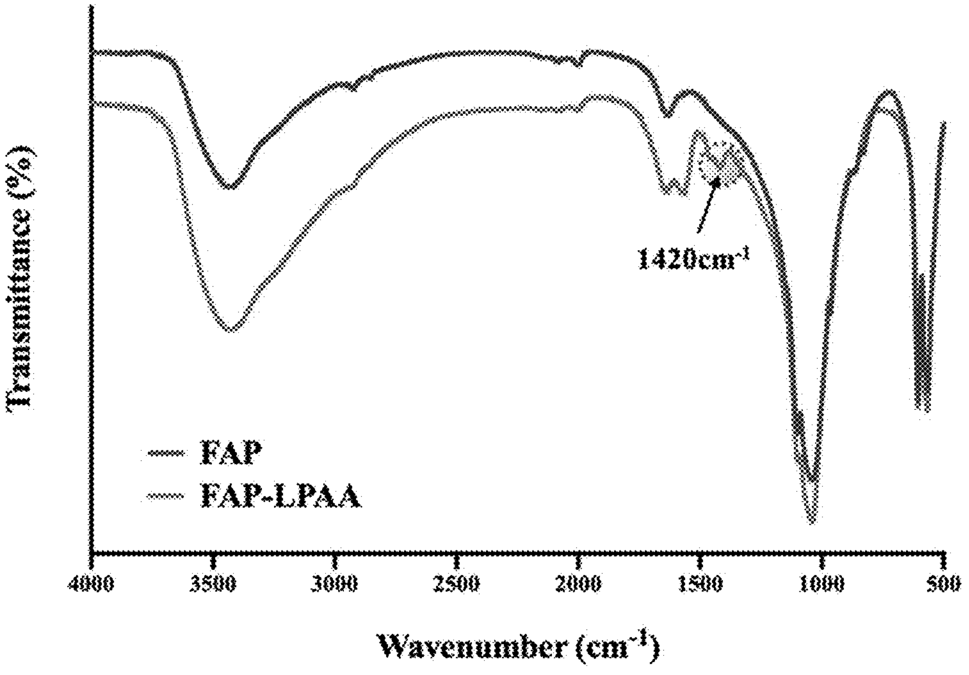
(FIG. 2C) fourier transform infrared (FTIR) spectrum of FAP and FAP-LPAA.
Figure 2D:
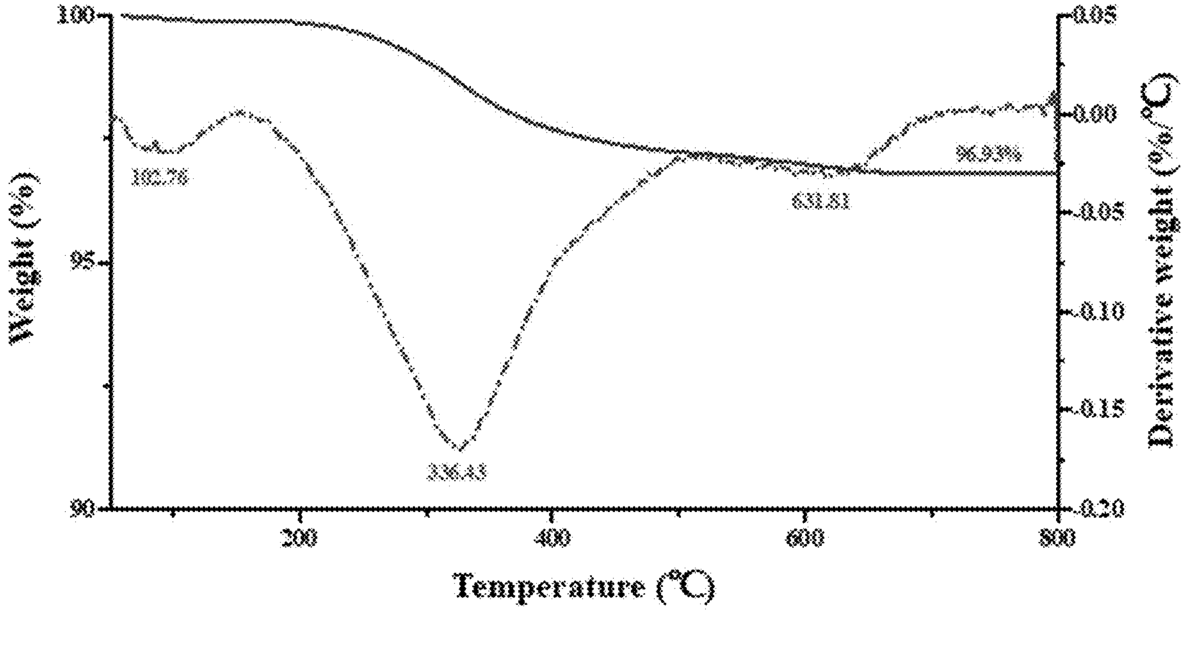
(FIG. 2D) thermogravimetric analysis of FAP-LPAA. Scale Bar.
Figure 3A:
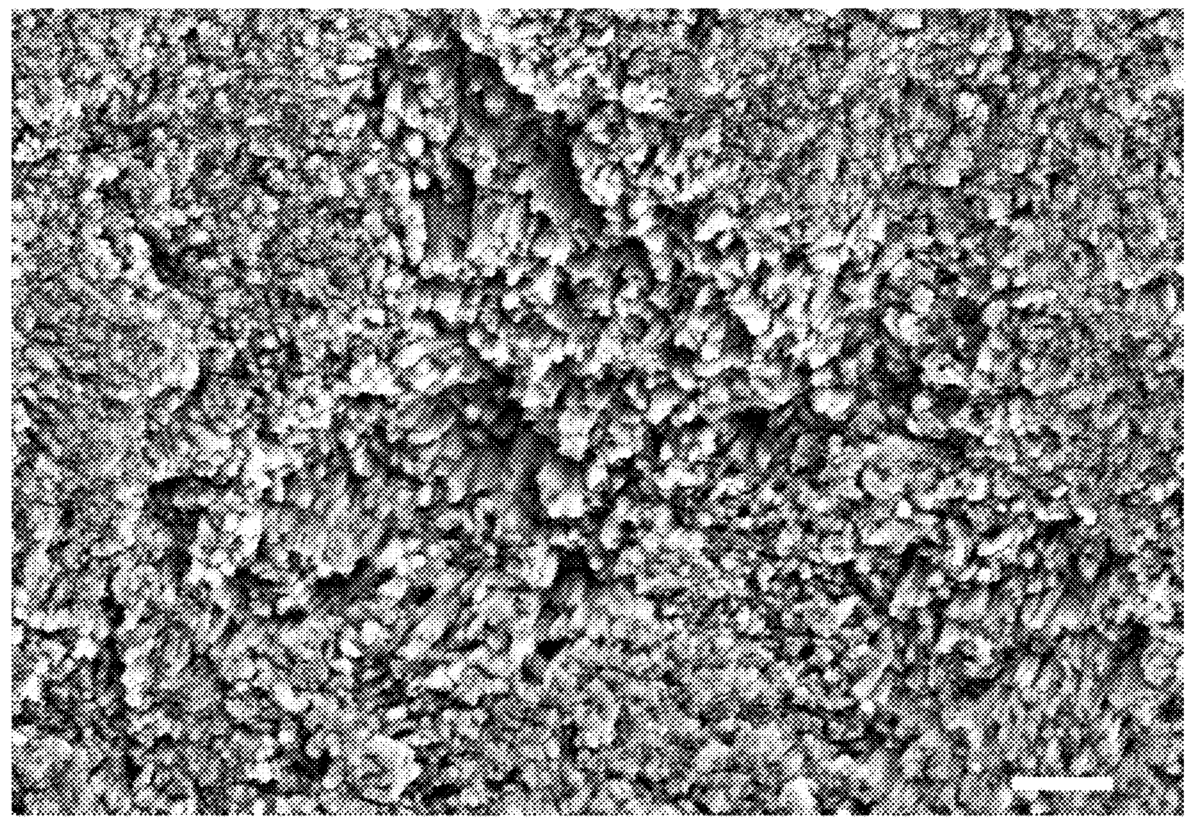
FIGS. 3A-3J. Physicochemical property of FAP-LPAA.
Figure 3B:
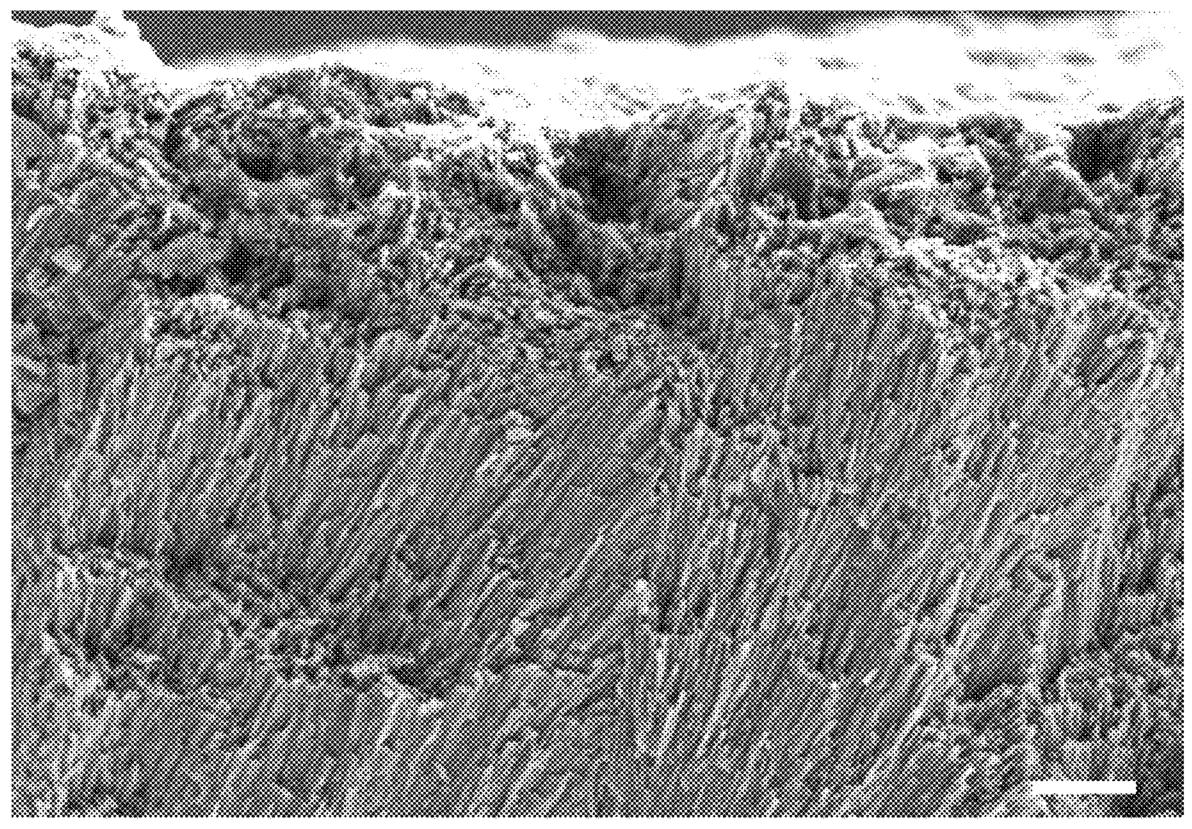
Figure 3C:
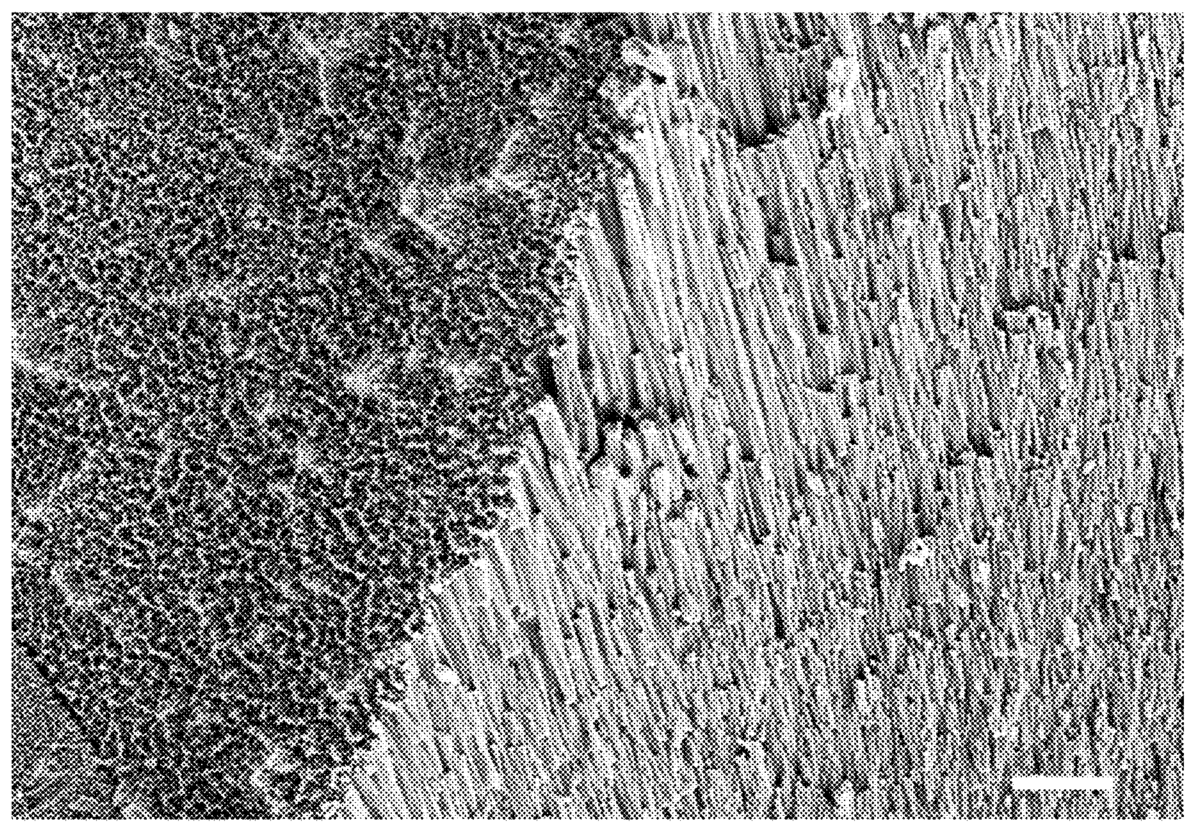
Figure 3D:
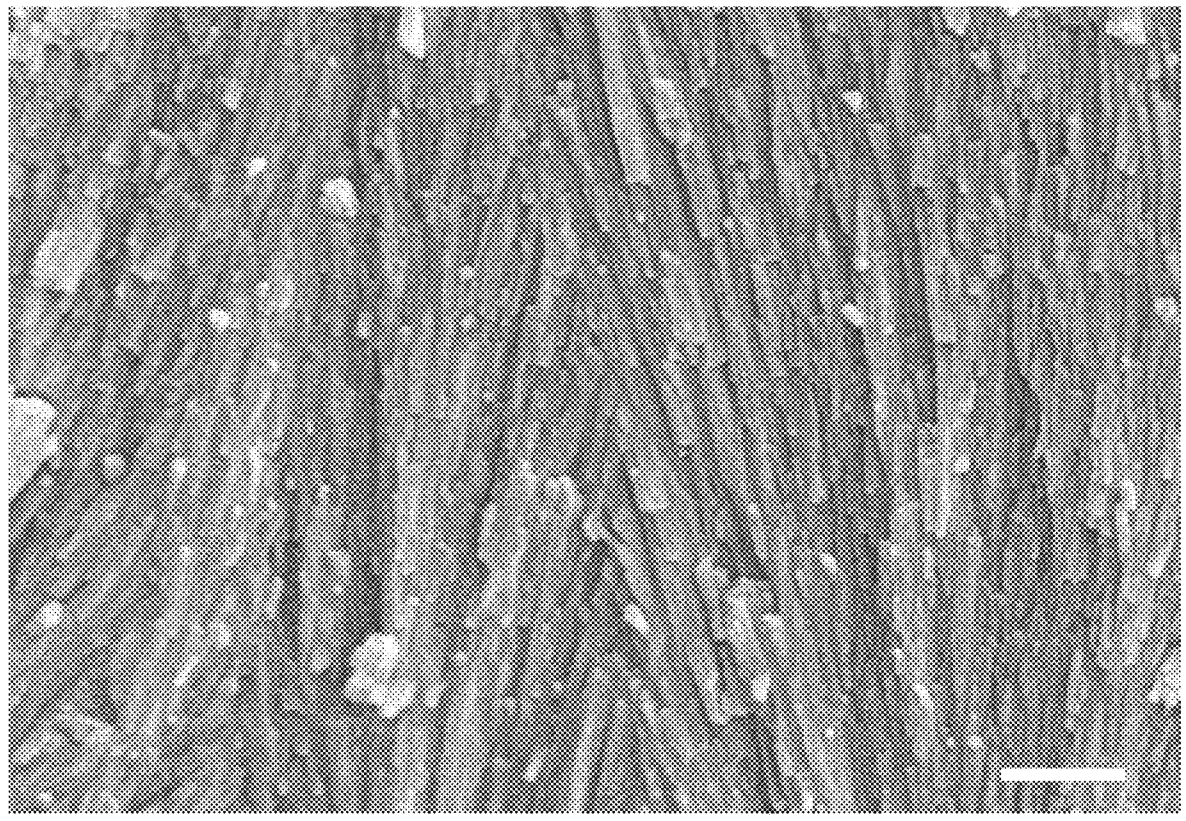
Figure 3E:
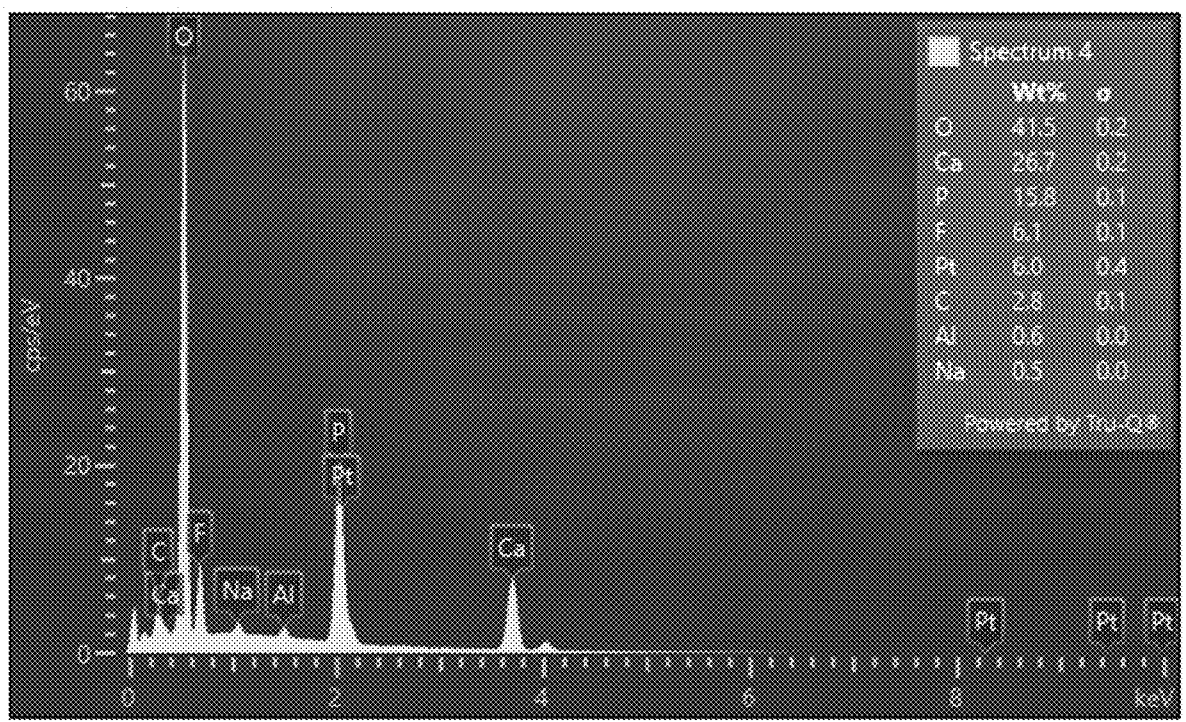
Figure 3F:
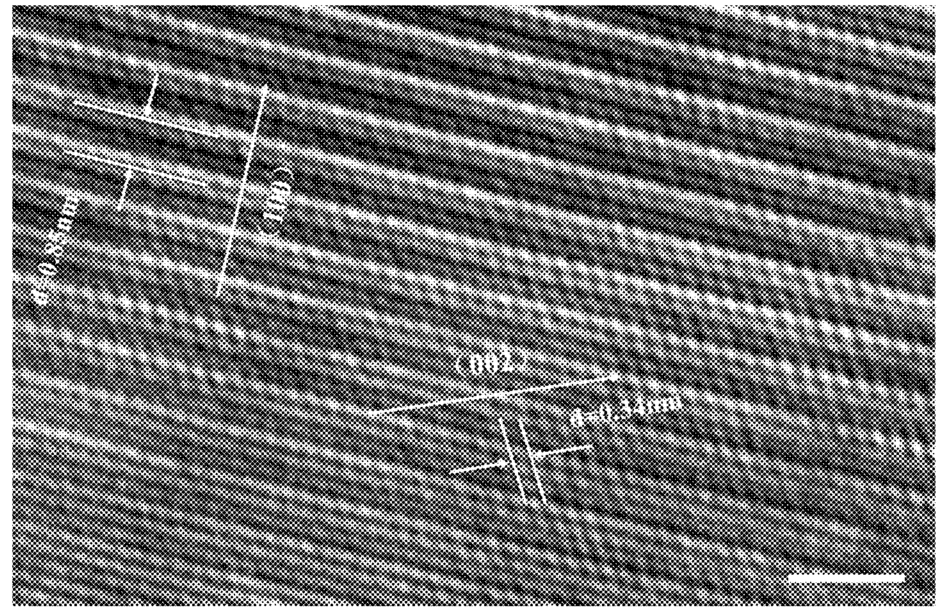
Figure 3G:
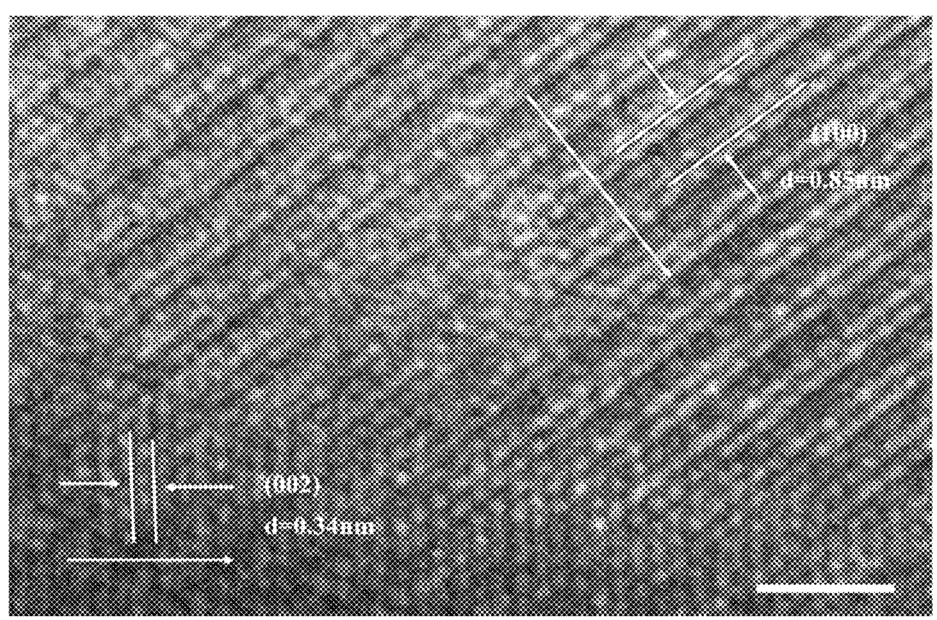
Figure 3H:
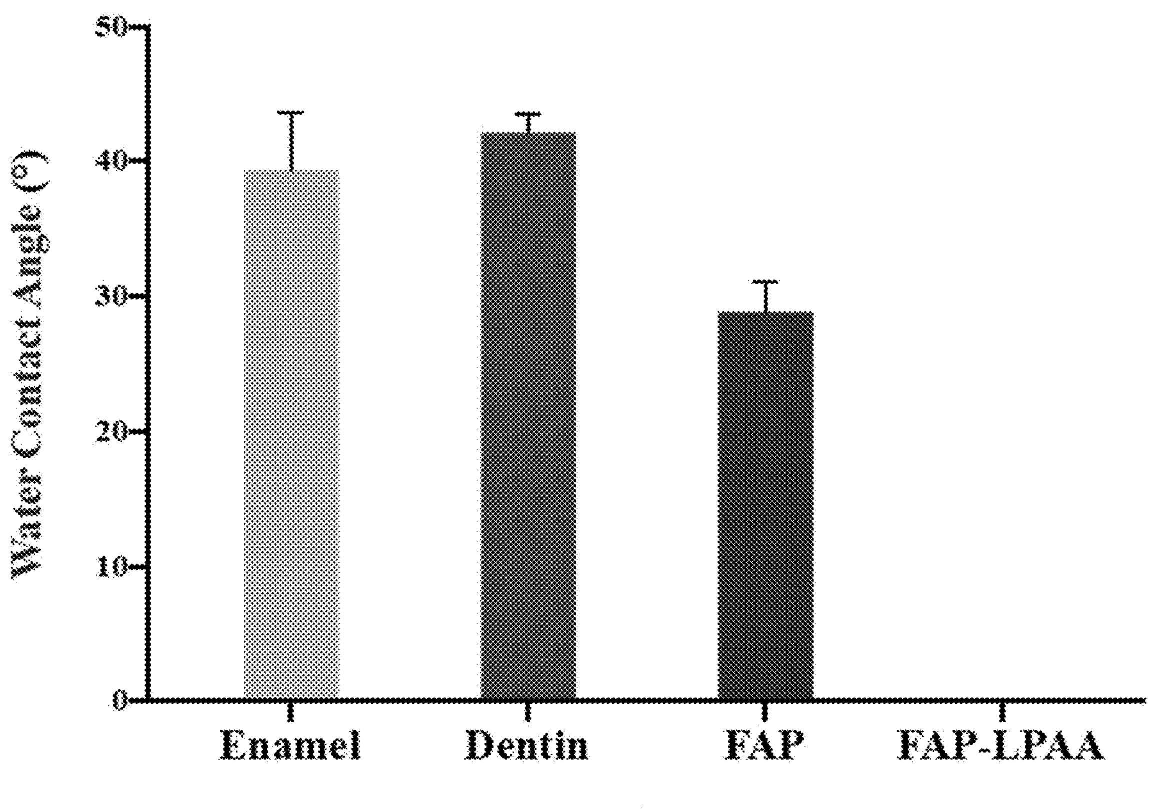
Figure 3I:
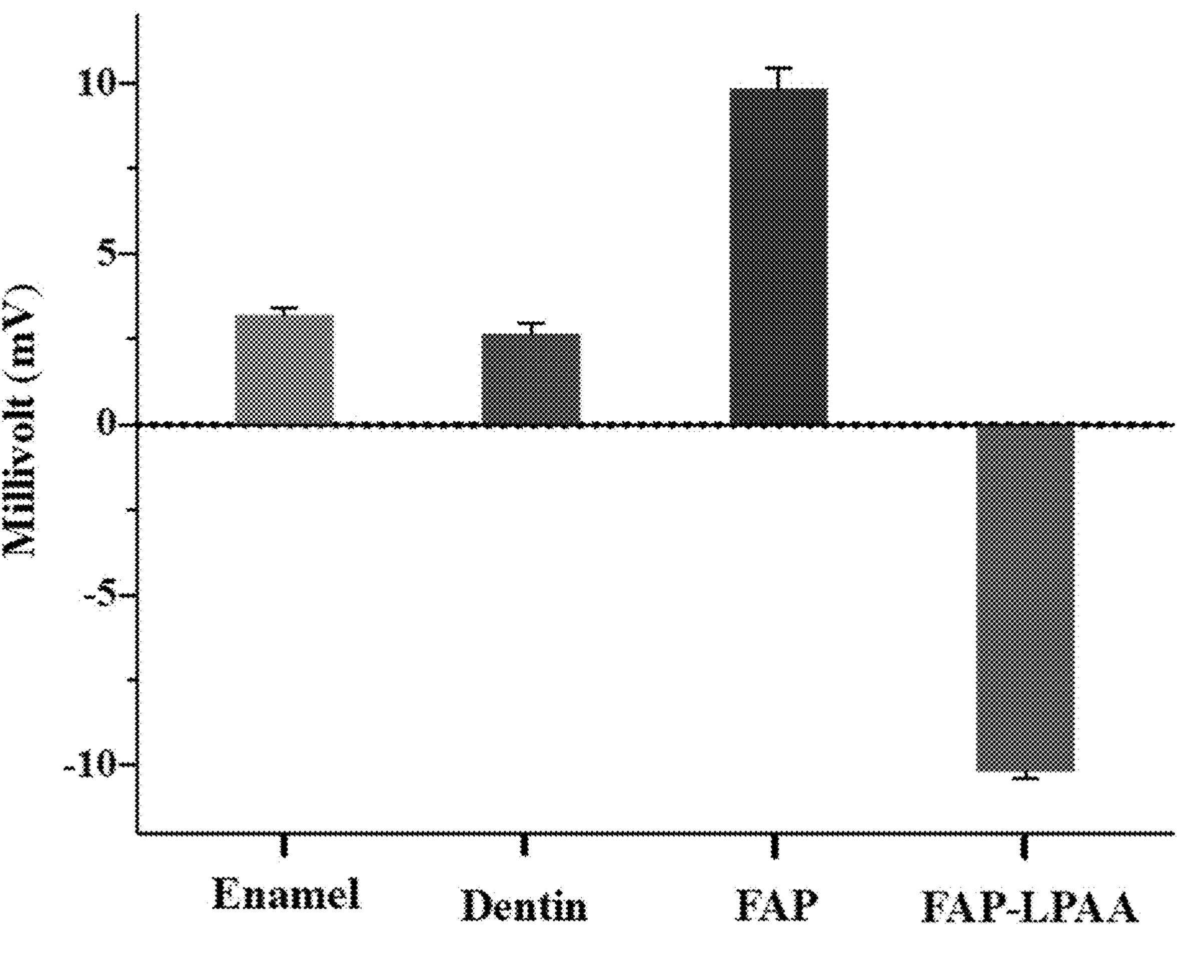
Figure 3J:
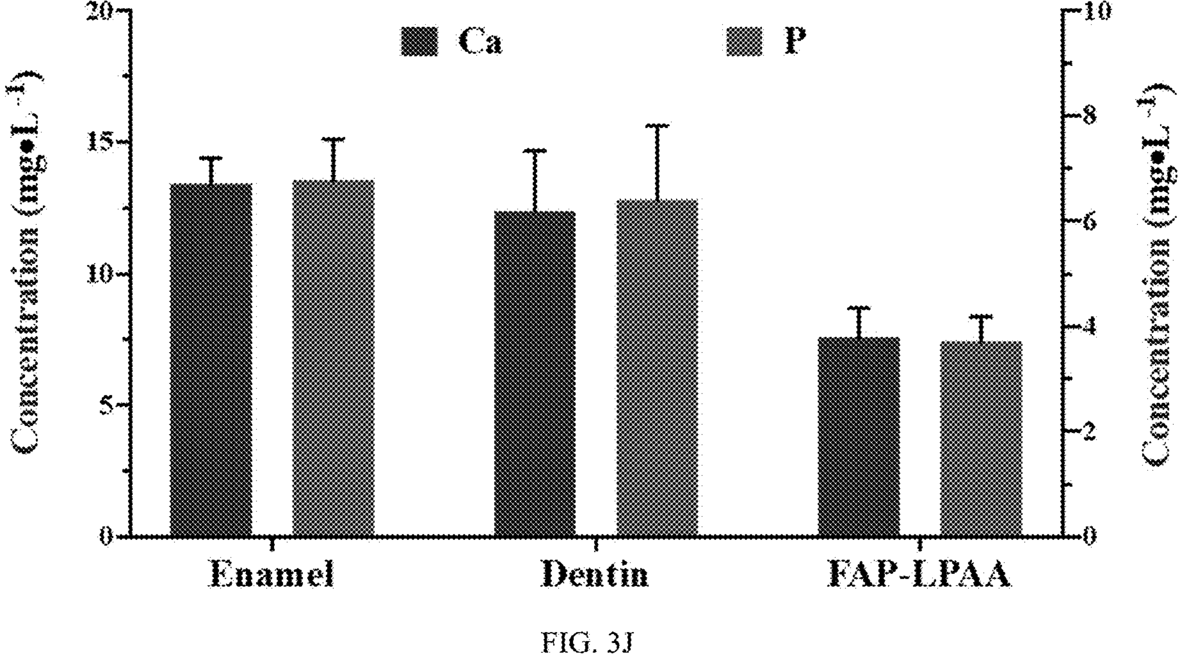
Figure 4A:
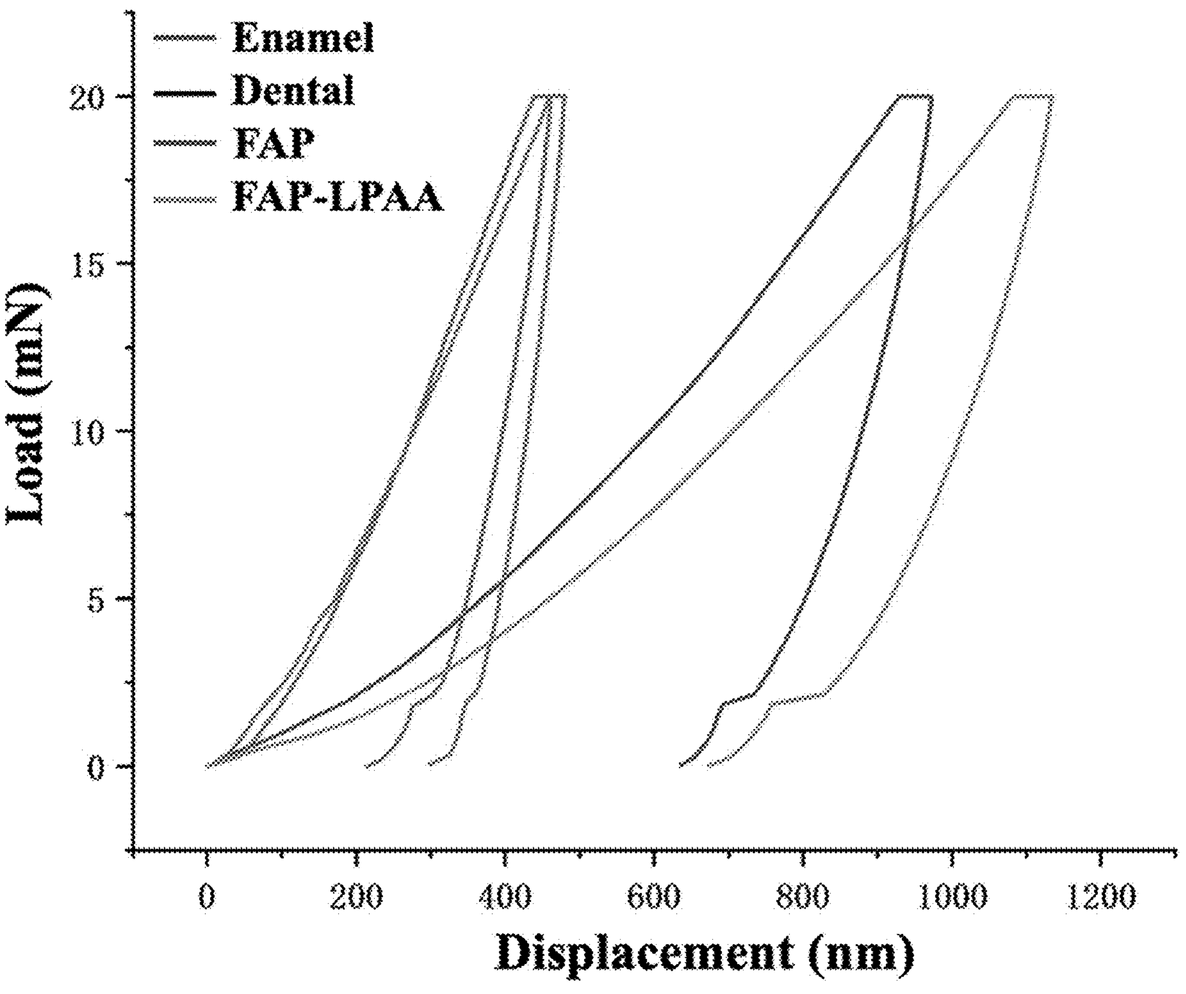
FIGS. 4A-4G. Mechanical property of FAP-LPAA.
Figure 4B:
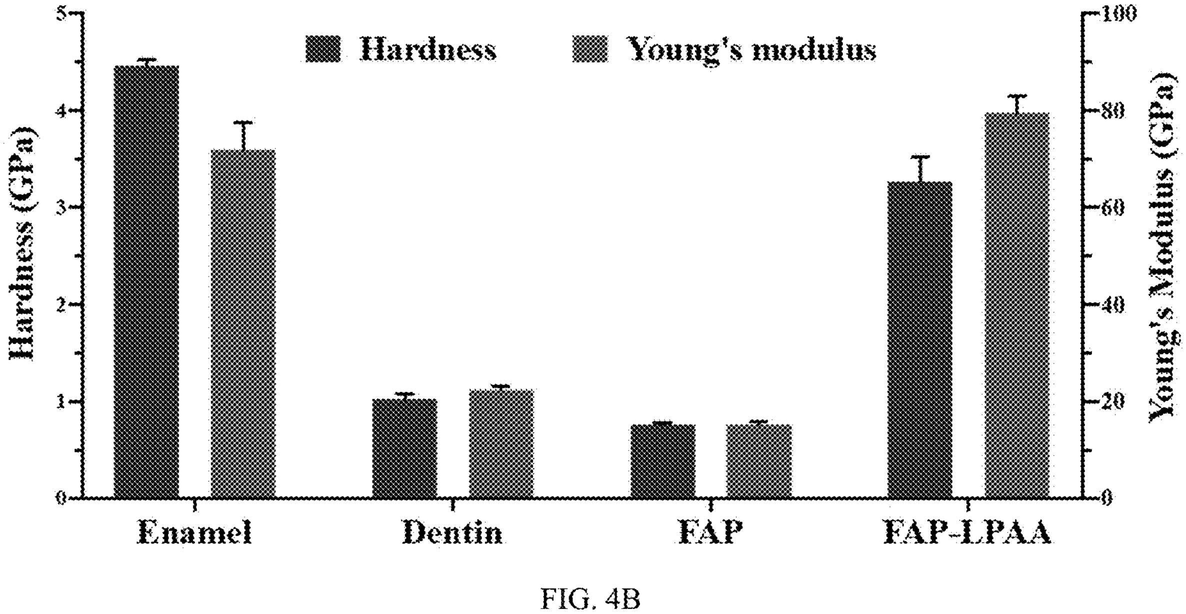
Figure 4C:
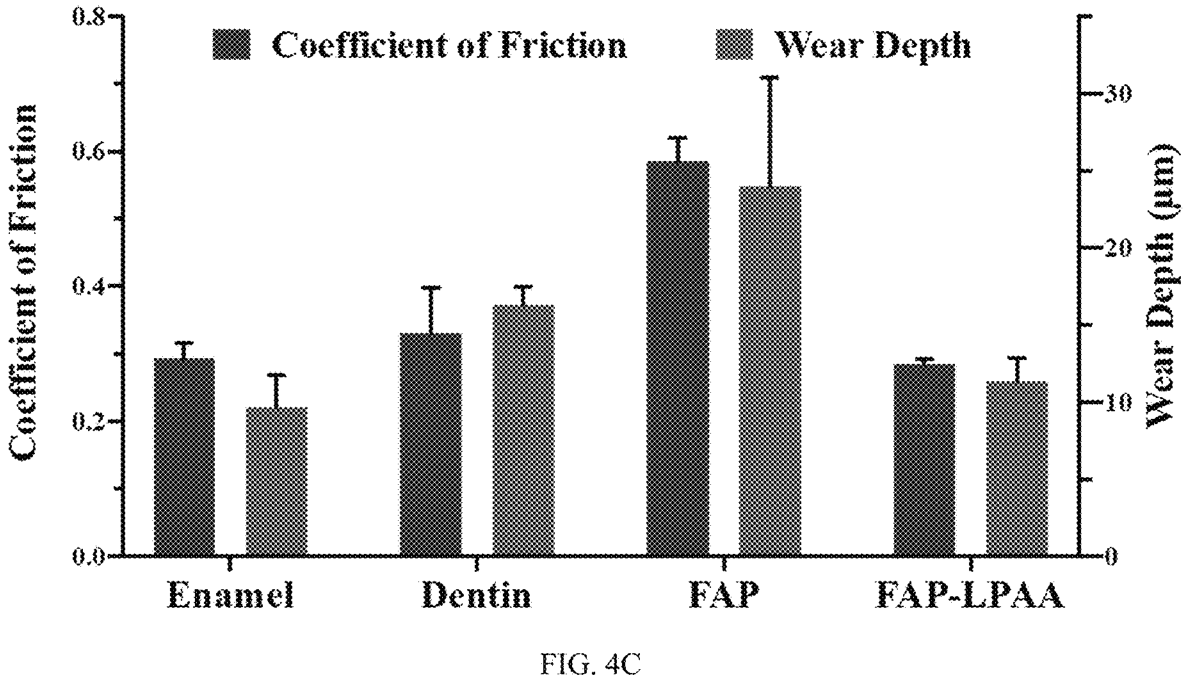
Figure 4D:
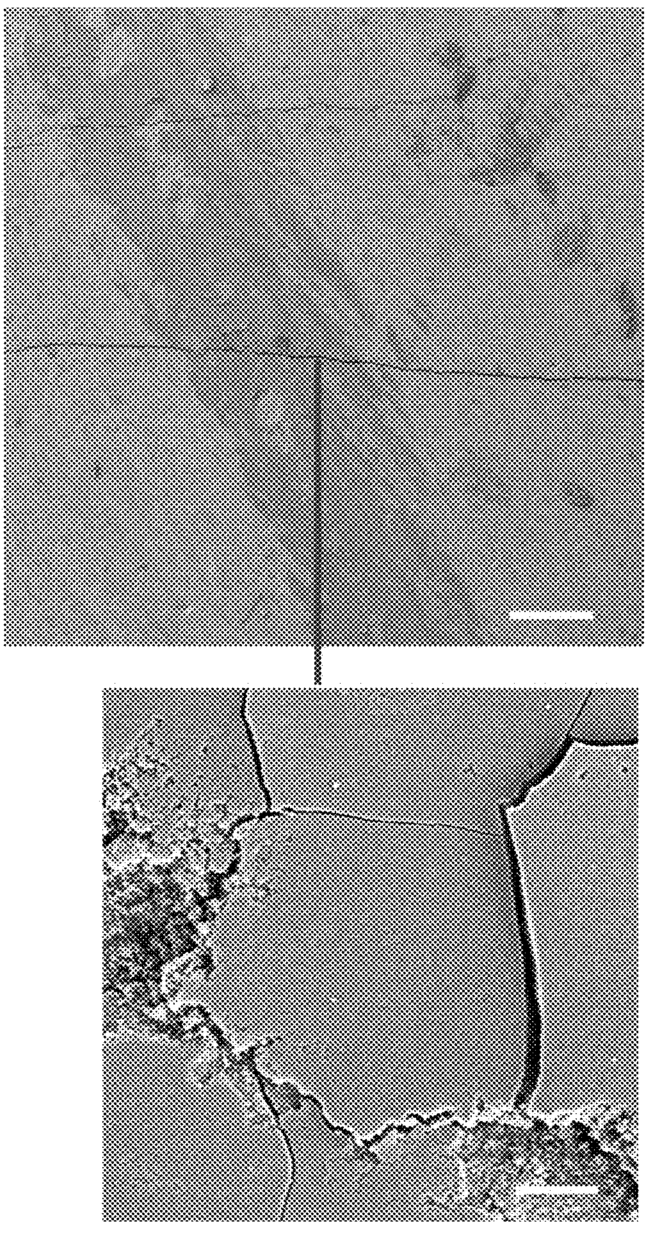
Figure 4E:
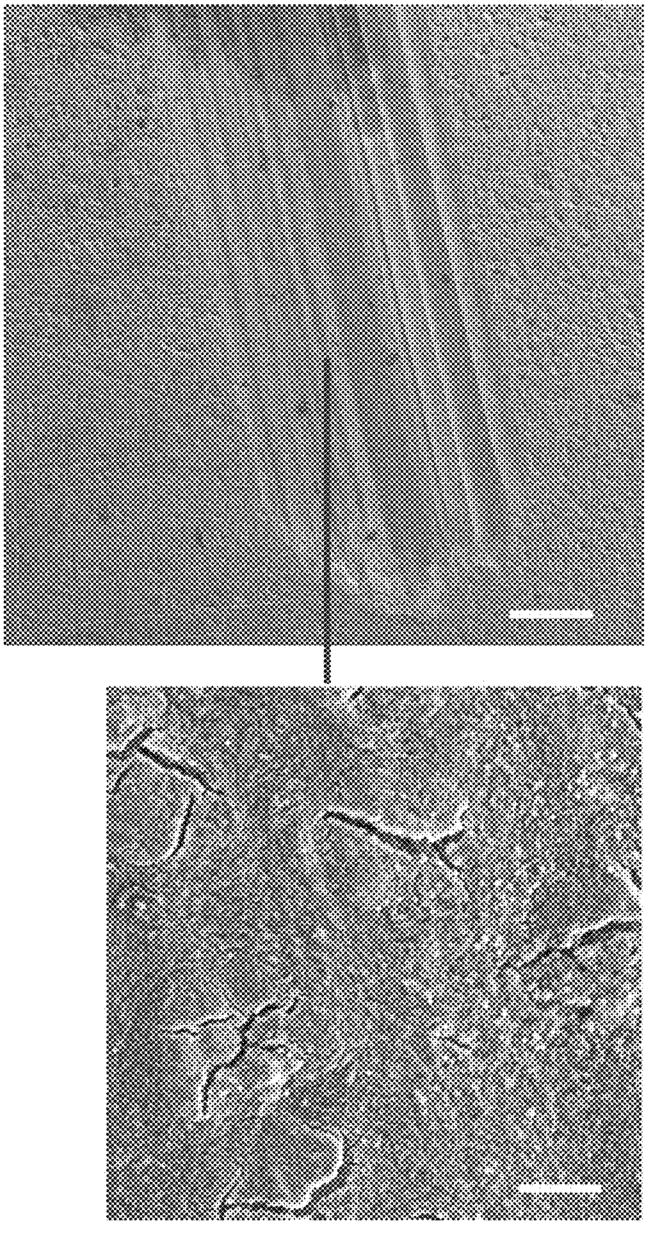
Figure 4F:
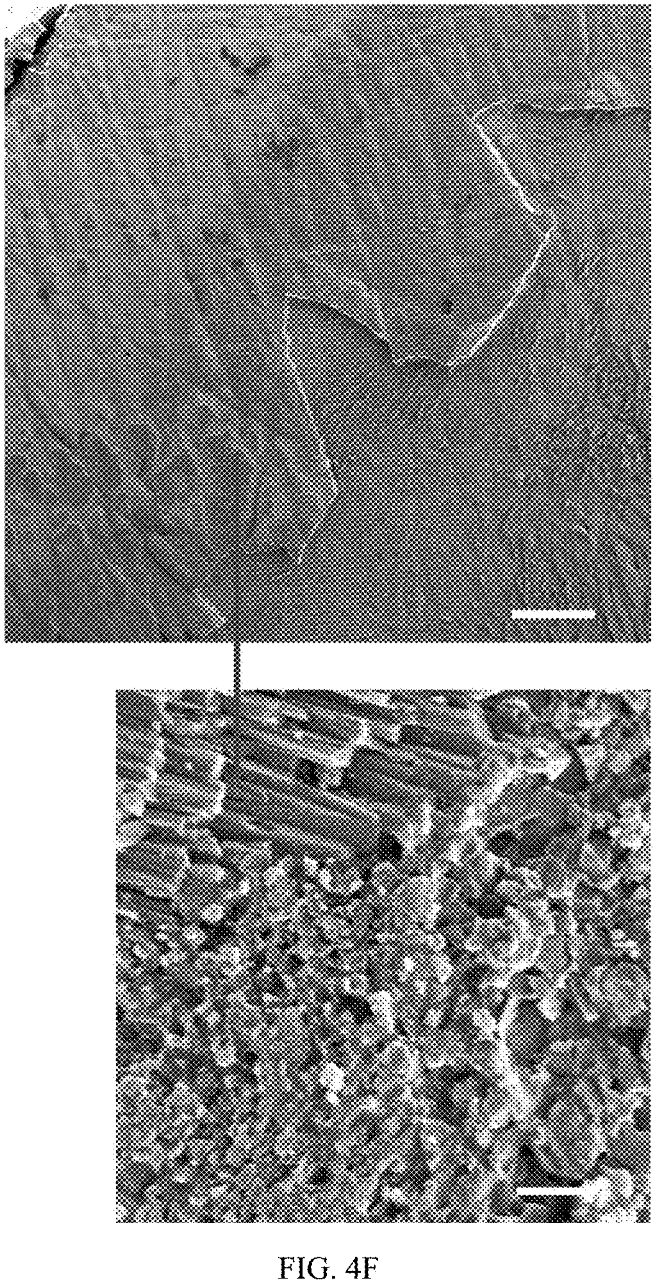
Figure 4G:
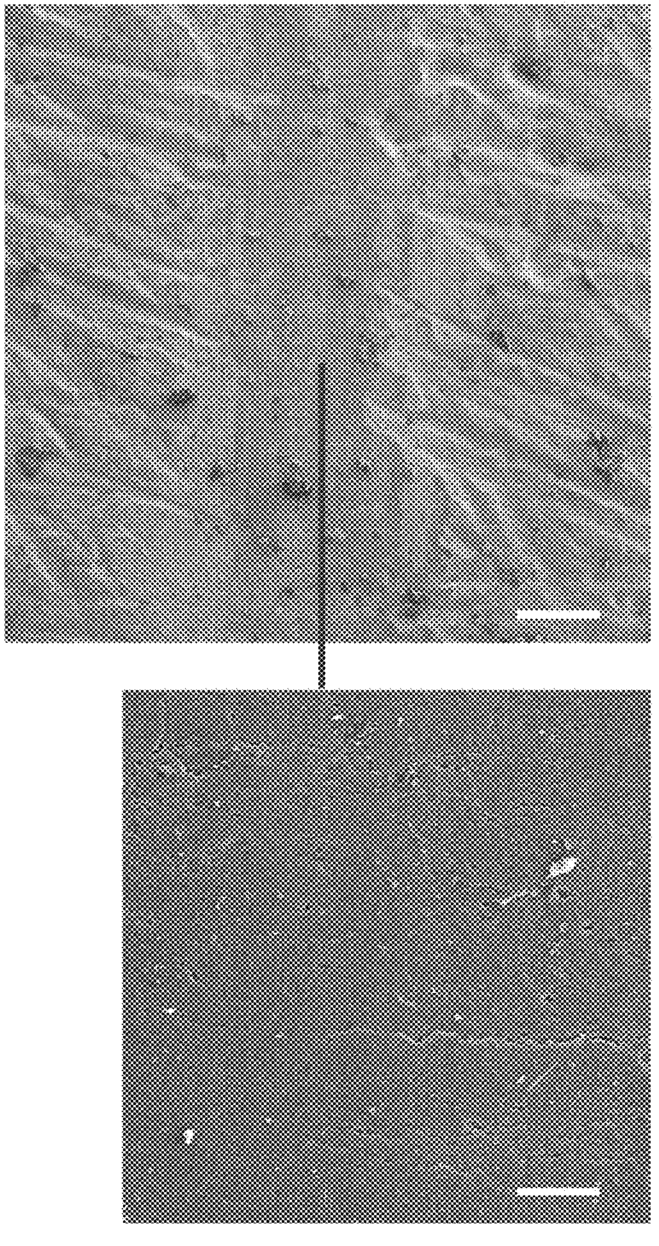
Figure 5:
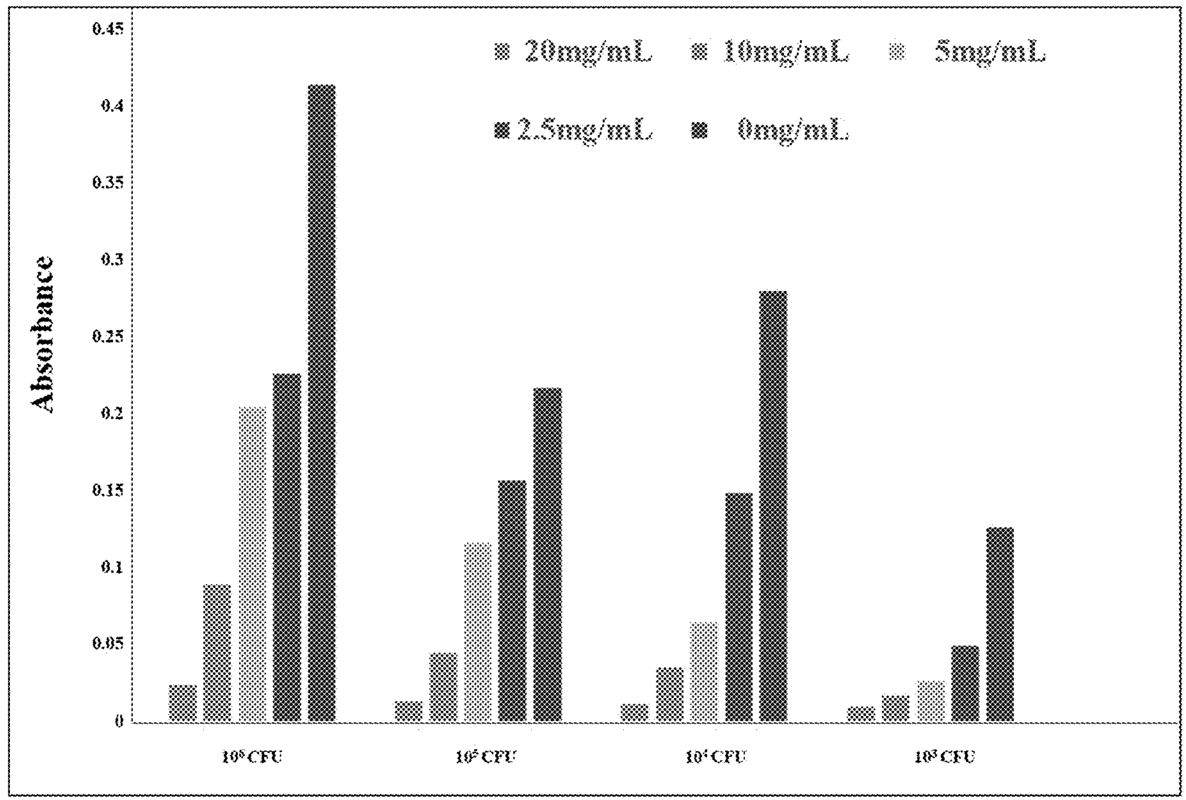
FIG. 5. Absorbance of *S. mutans* in various concentrations of LPAA and *S. mutans.*
Figure 6A:
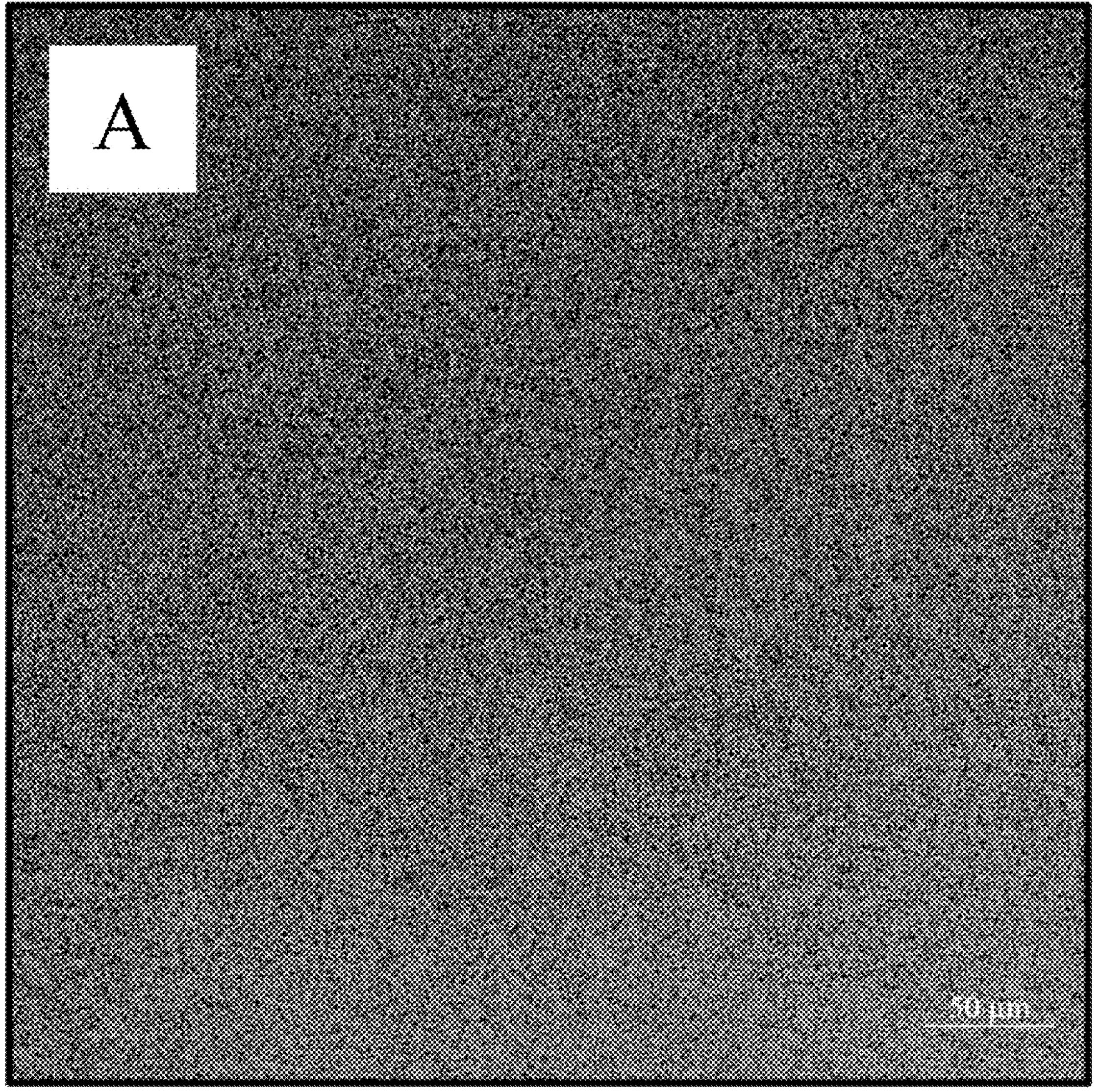
FIGS. 6A-6L. Fluorescence images of *S. mutans* in LPAA by CLSM.
Figure 6B:
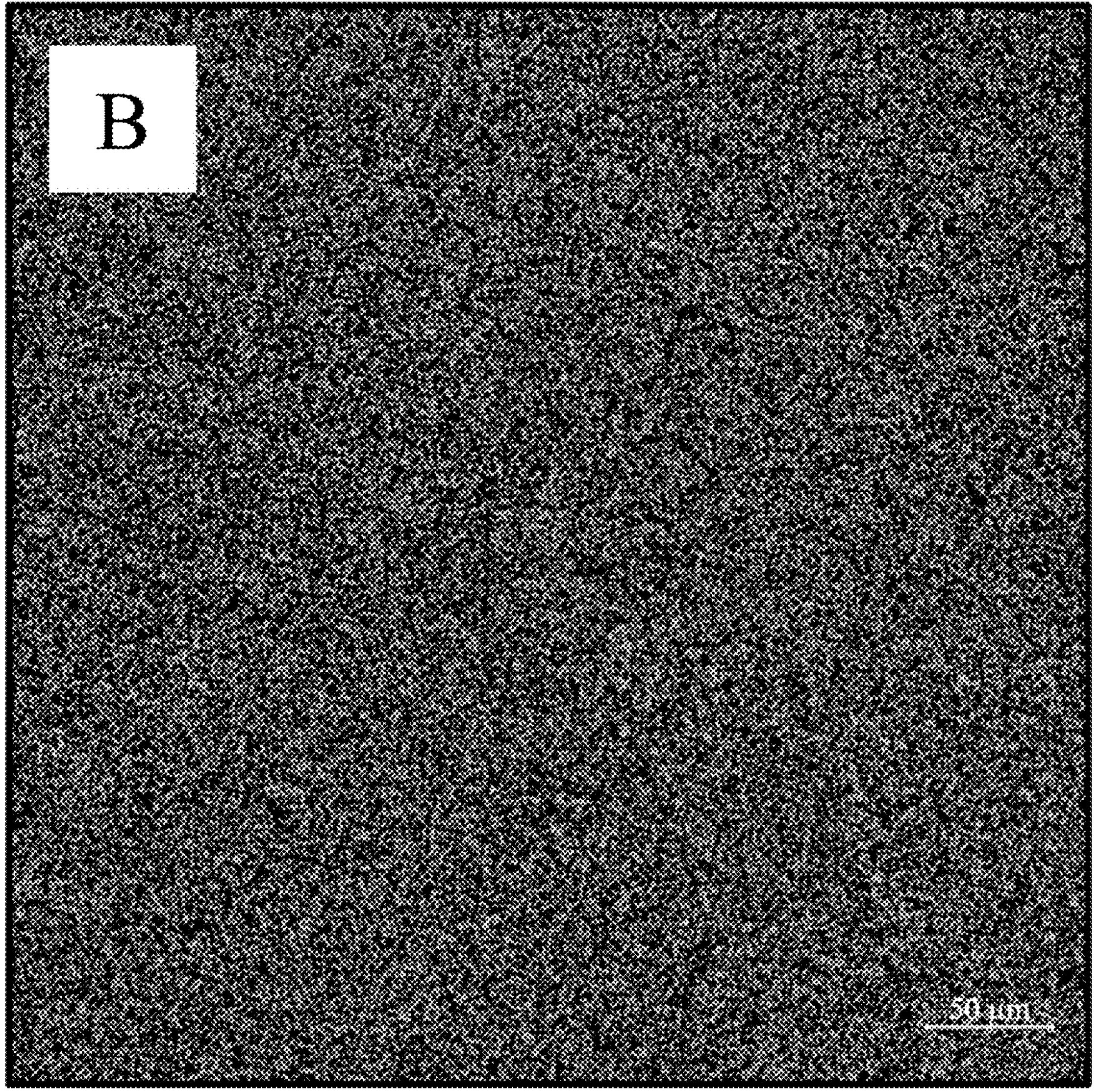
Figure 6C:
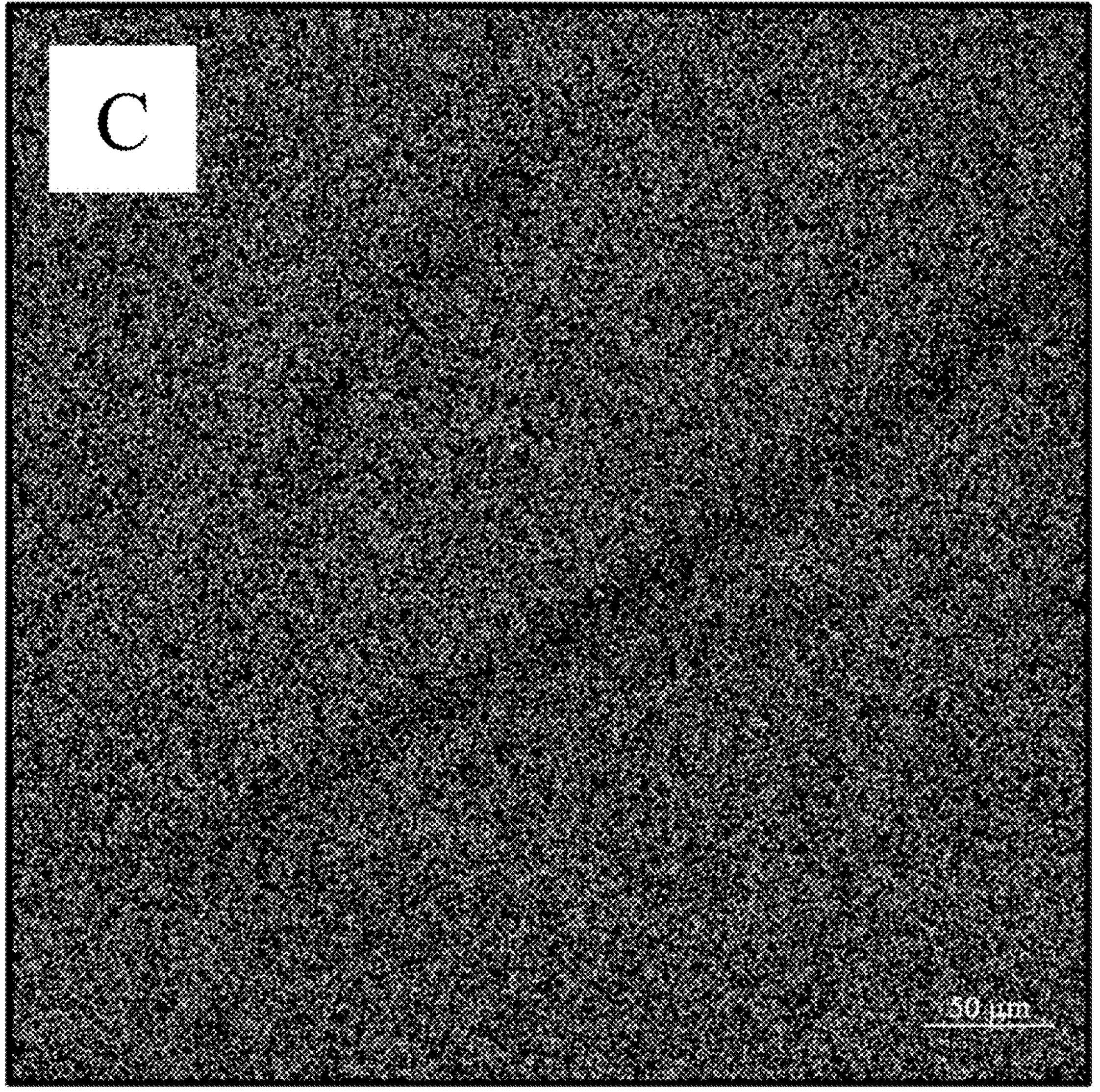
Figure 6D:
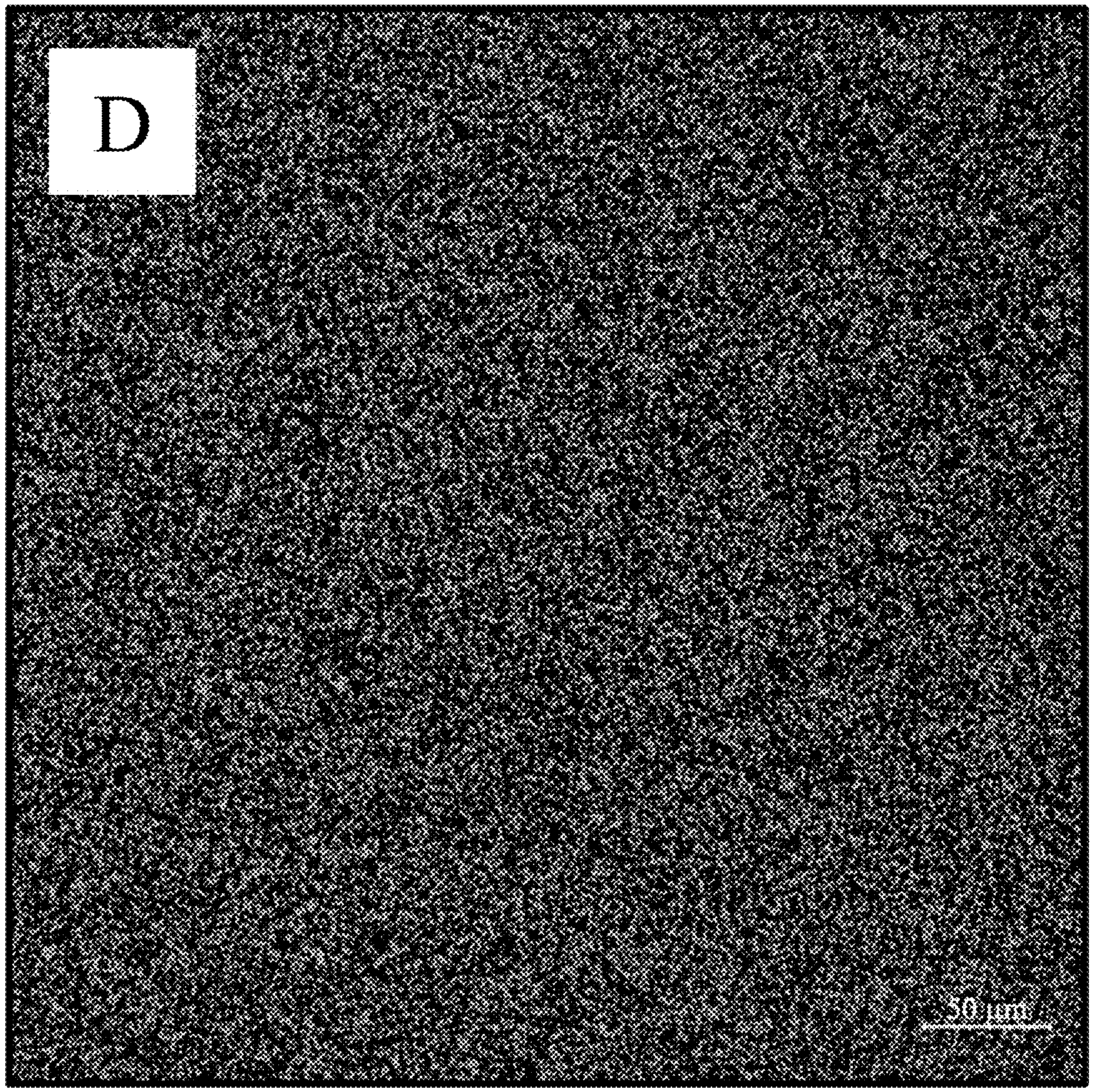
Figure 6E:
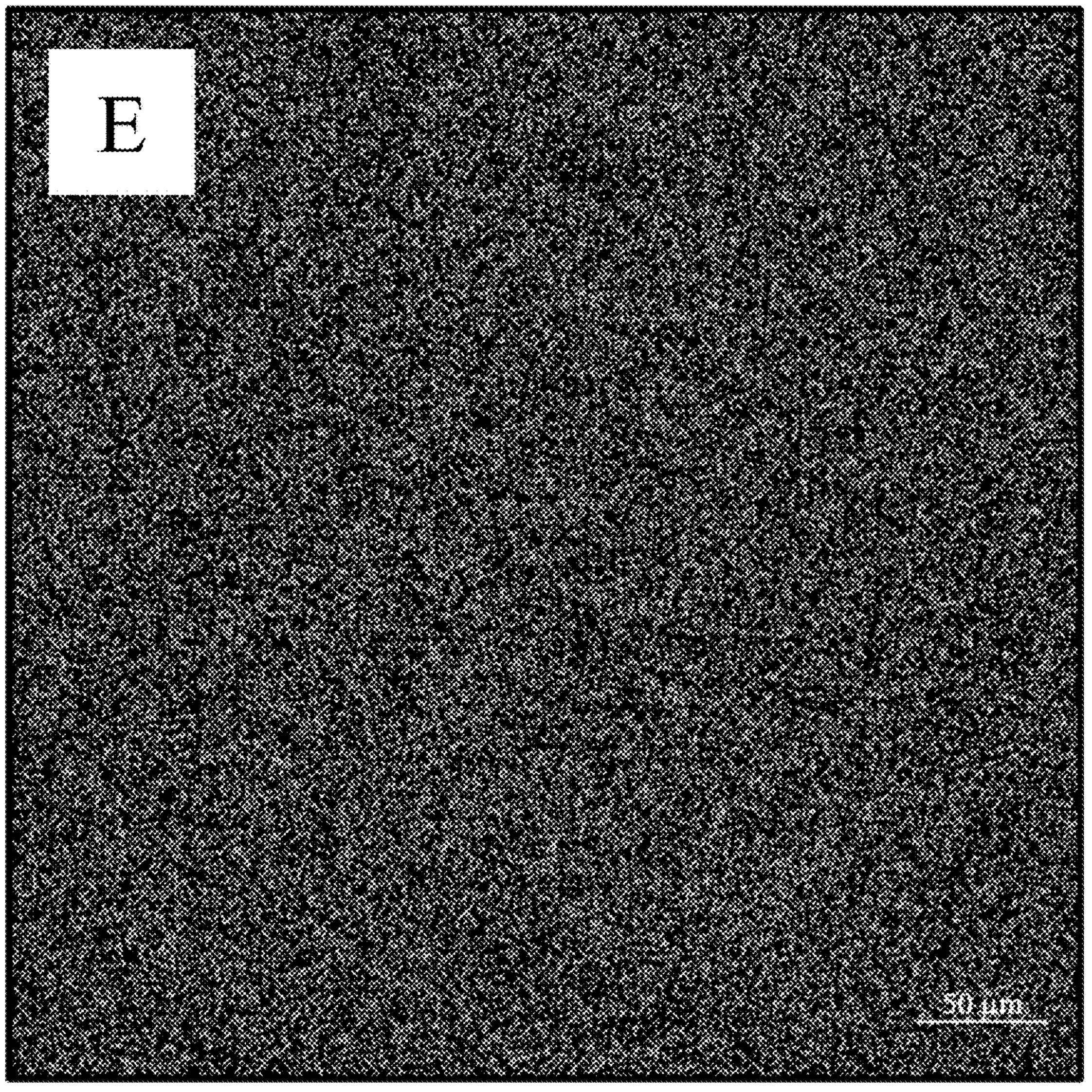
Figure 6F:
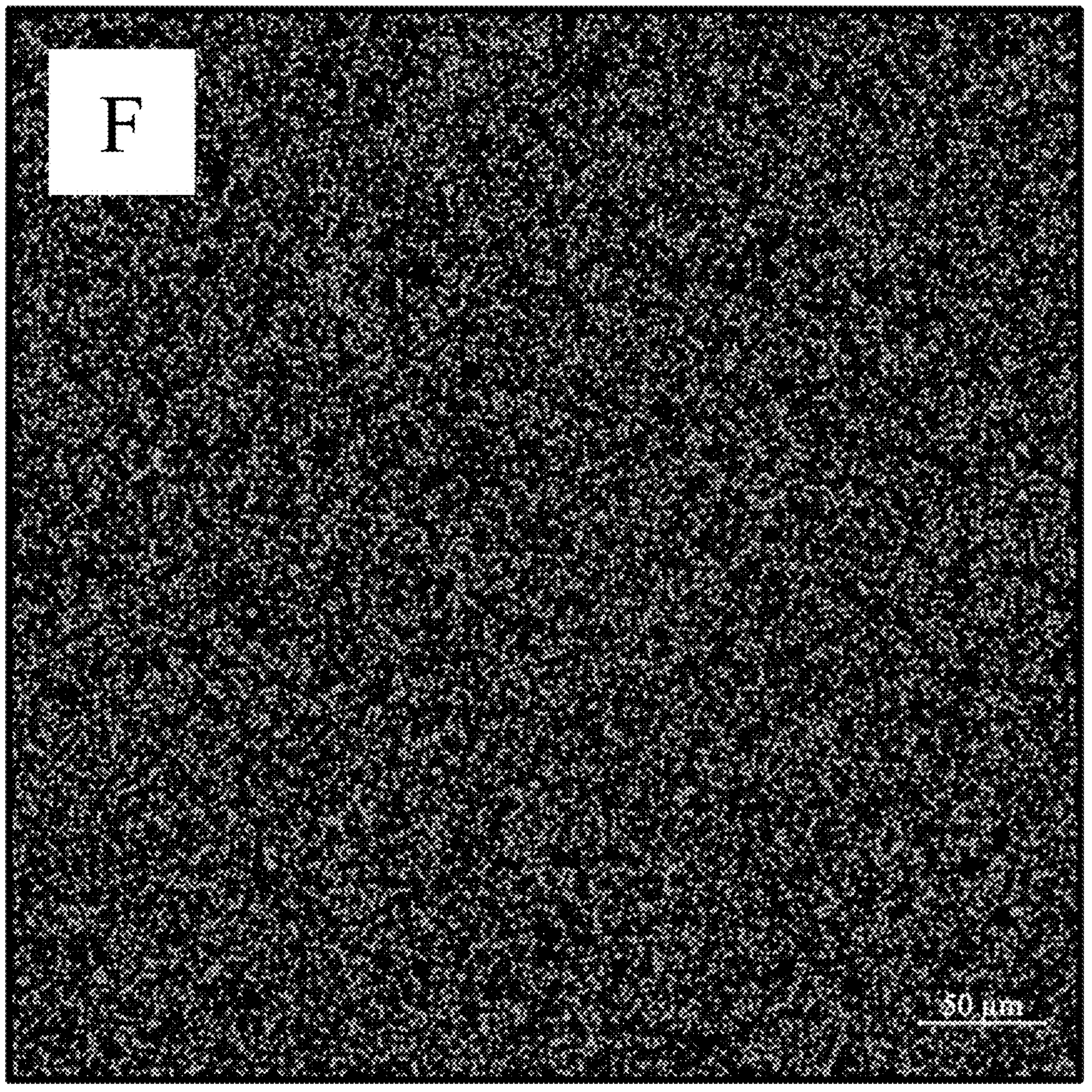
Figure 6G:
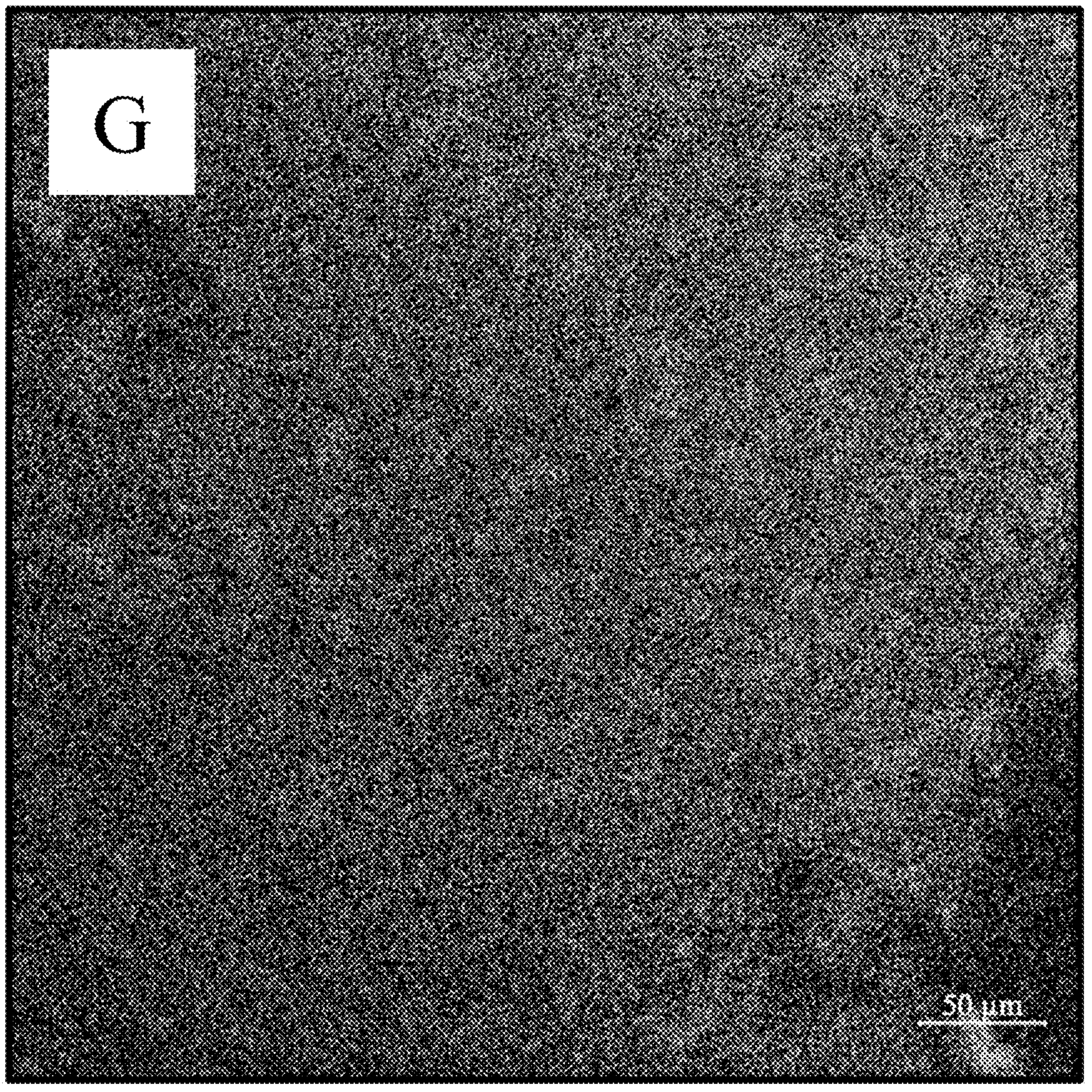
Figure 6H:
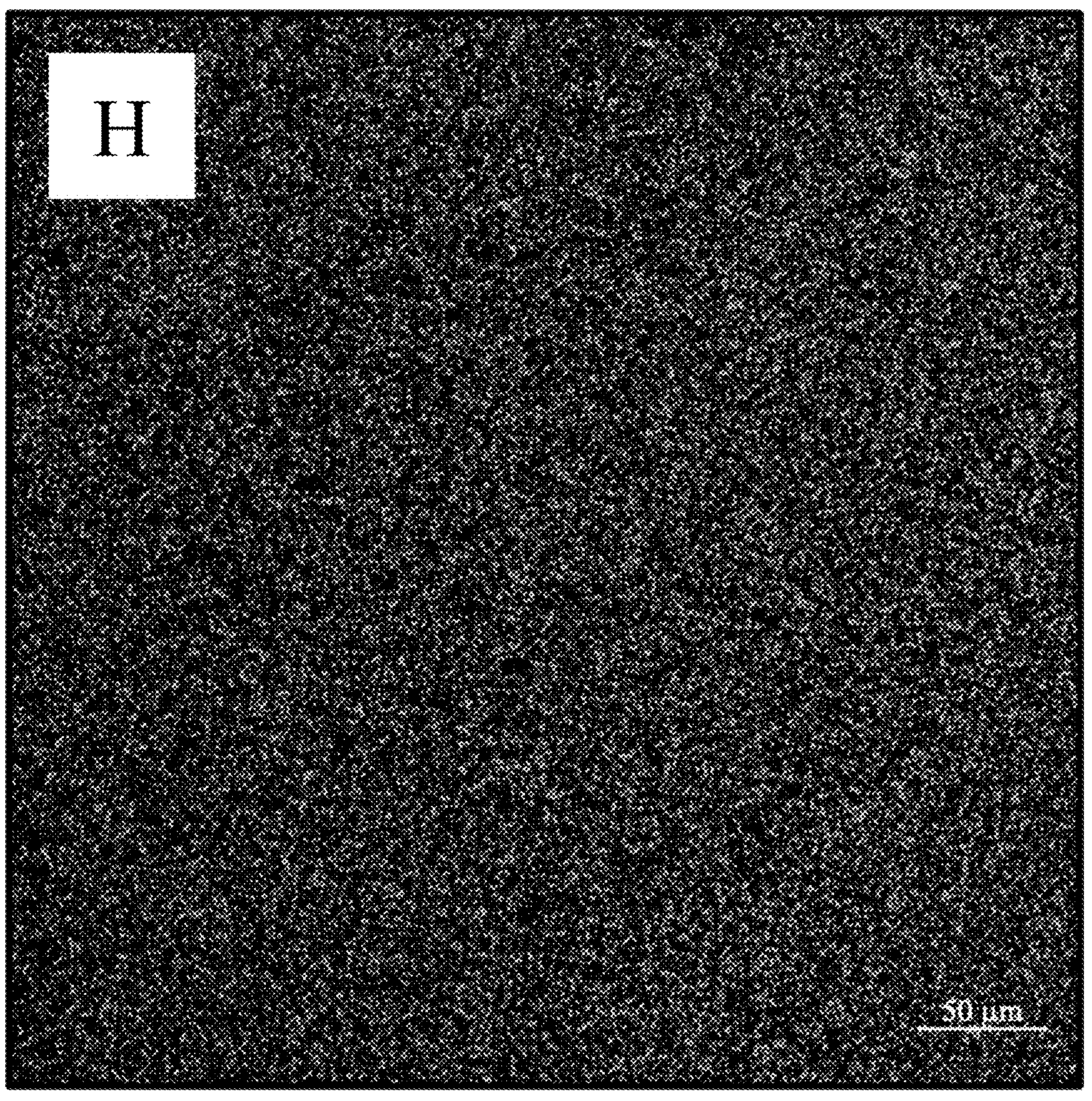
Figure 6I:
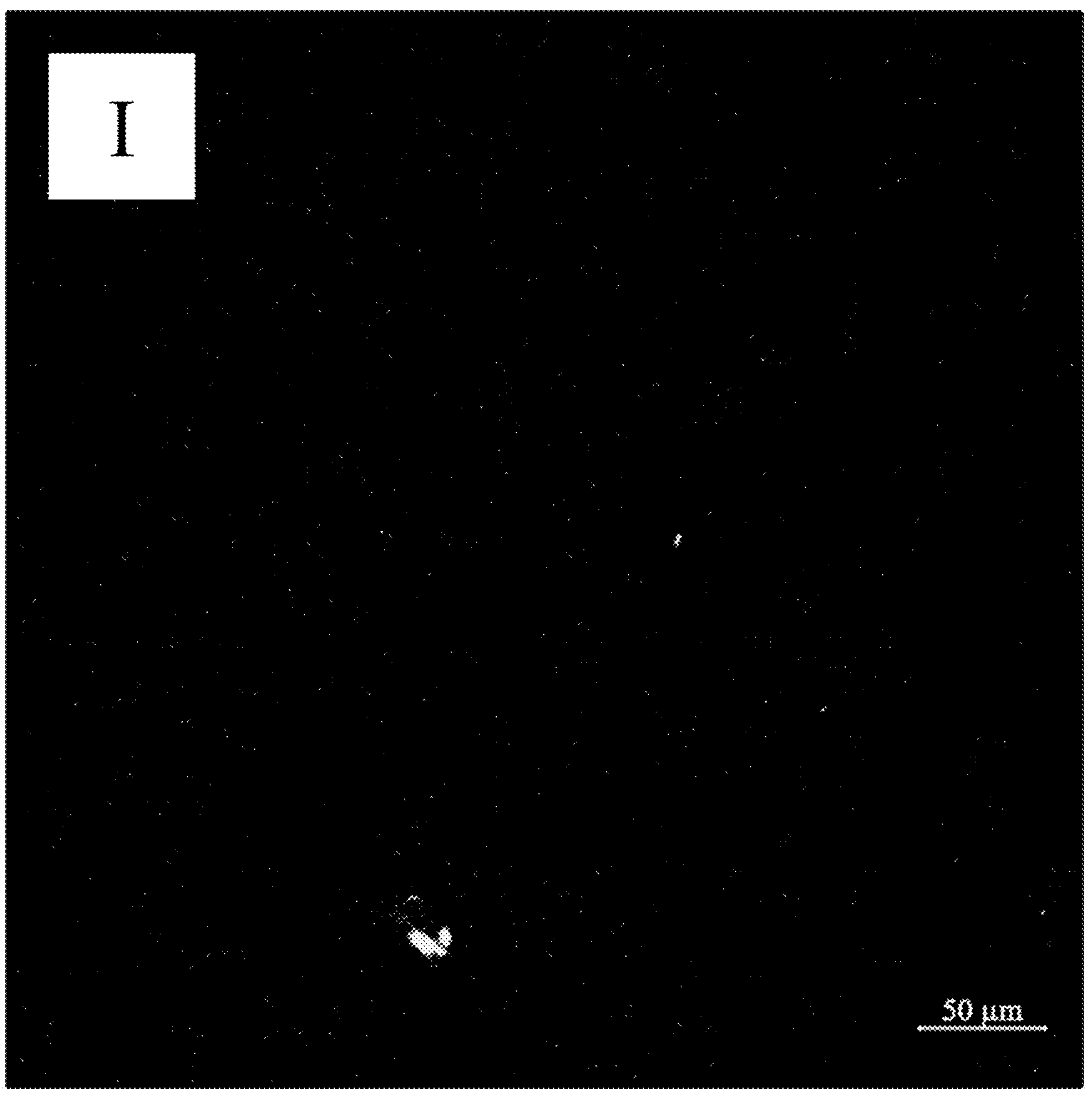
Figure 6J:
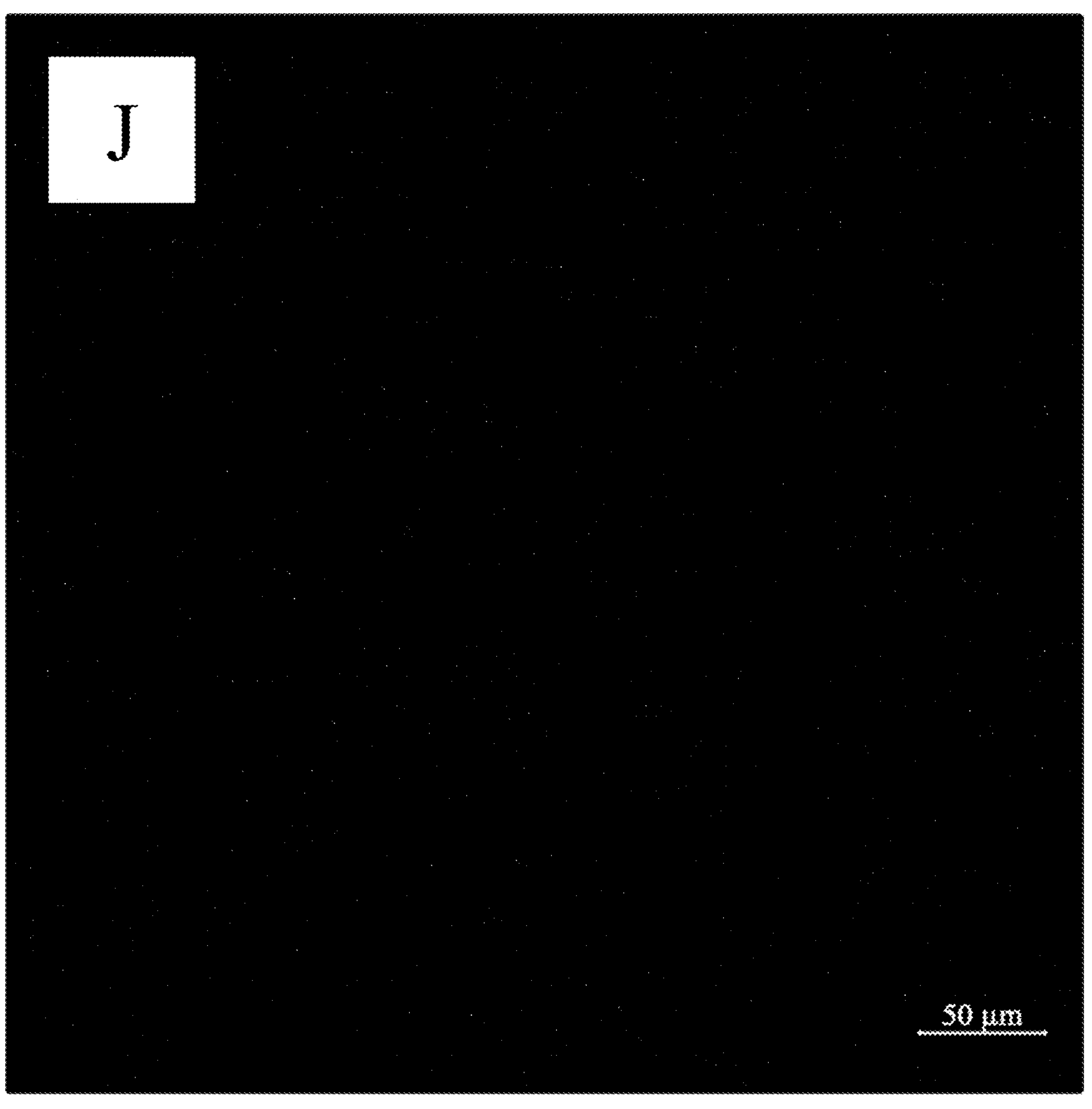
Figure 6K:
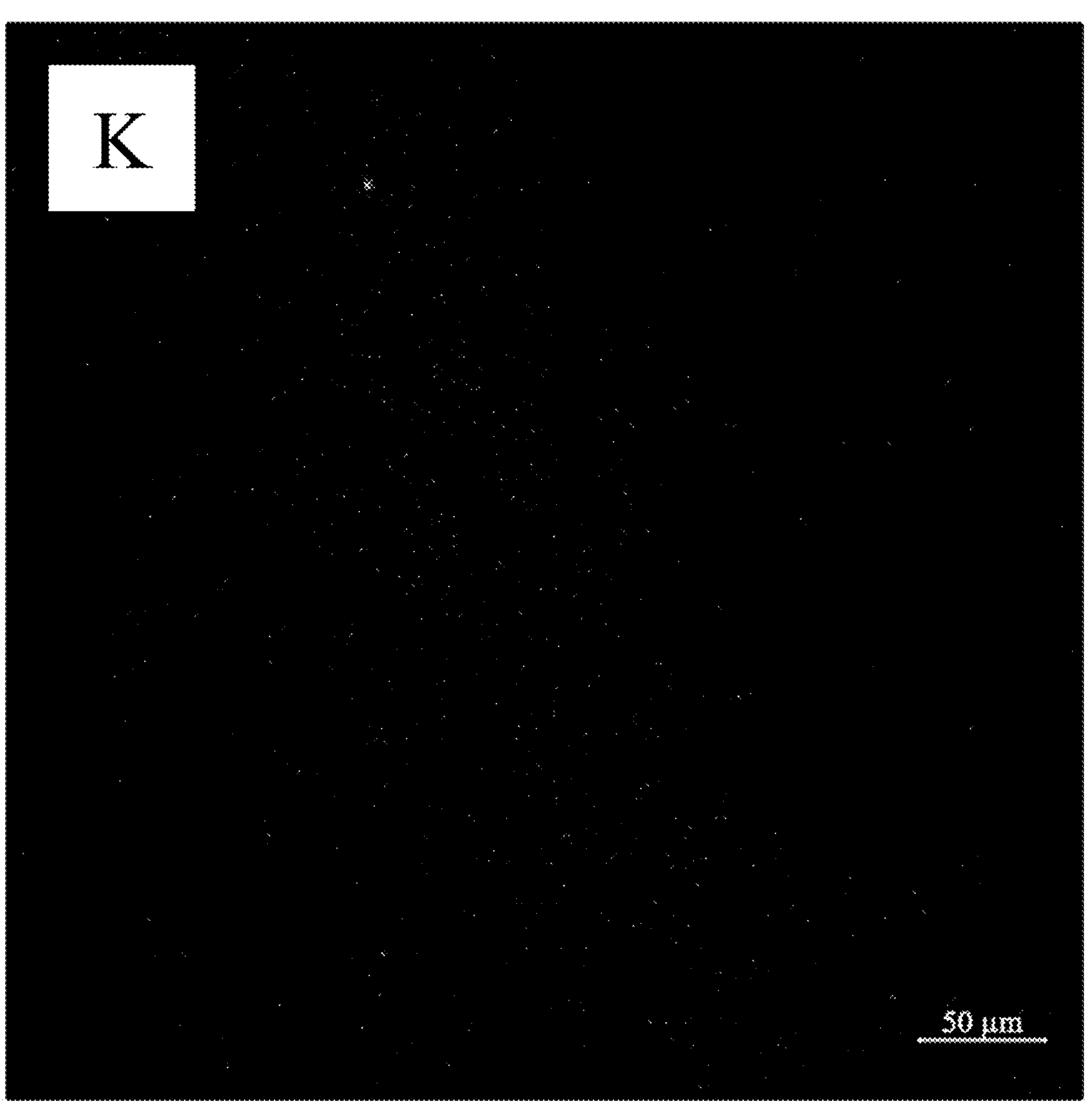
Figure 6L:
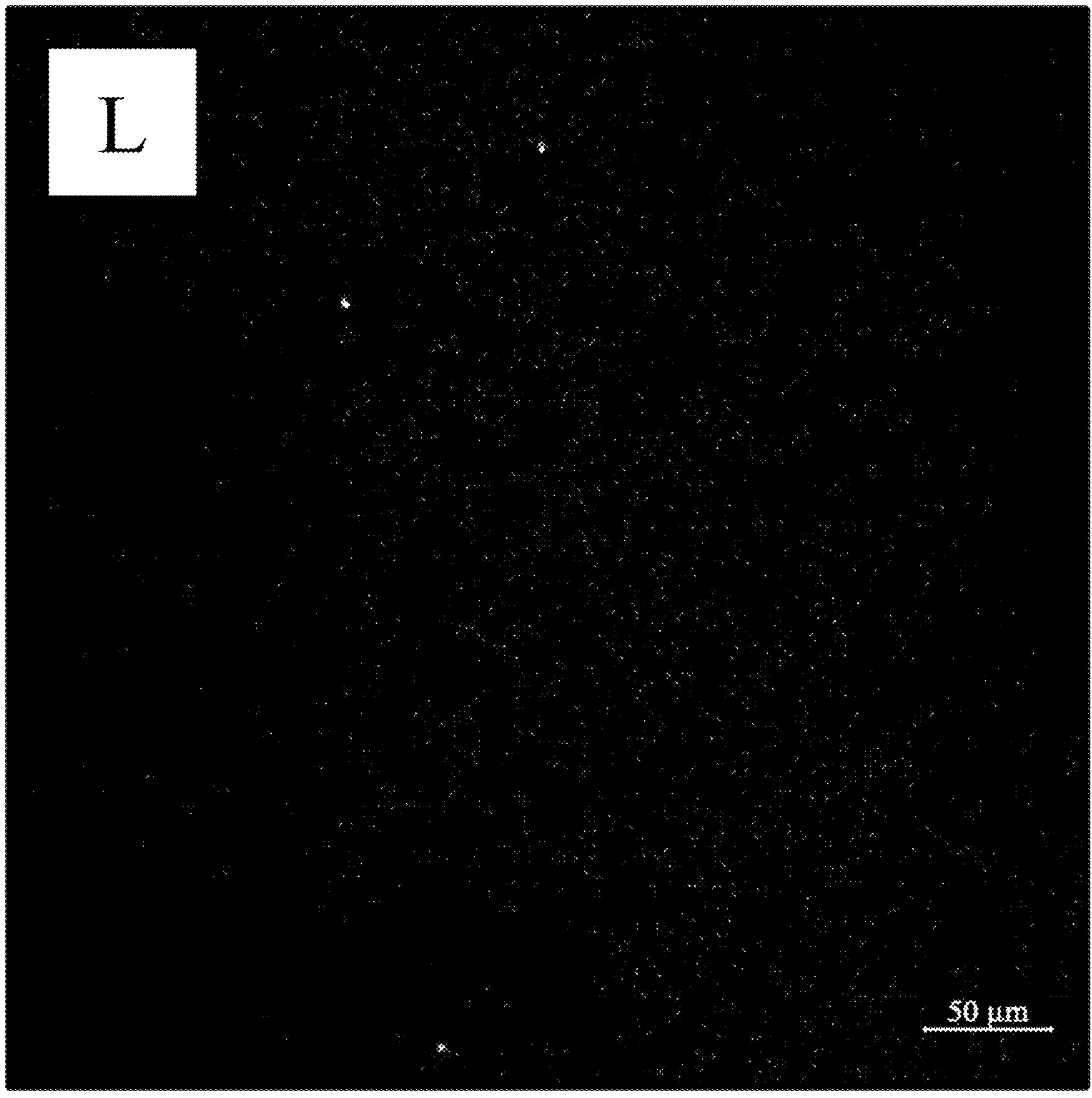
Figure 7A:
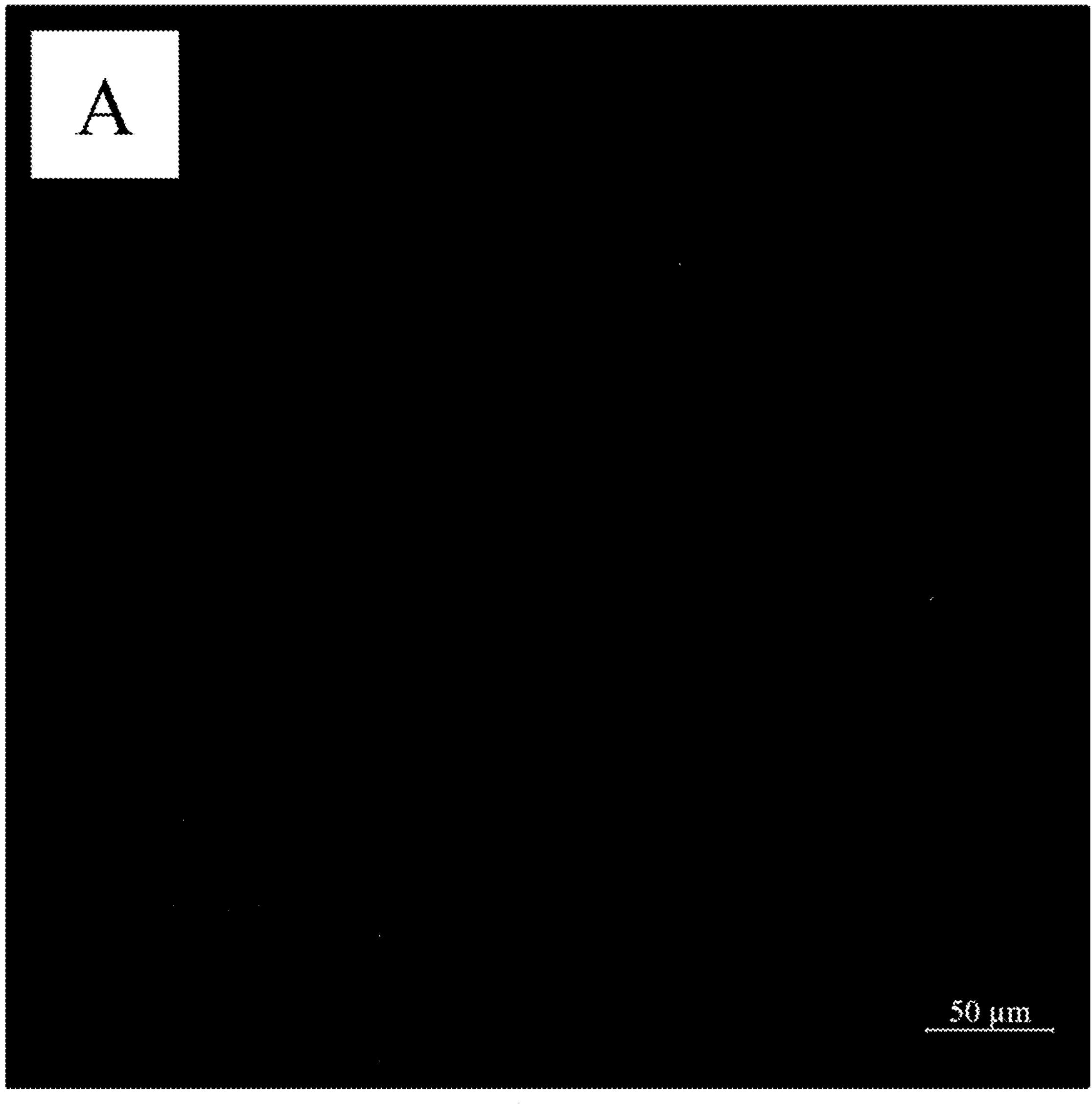
FIGS. 7A-7F. Fluorescence images of *S. mutans* in LPAA by CLSM.
Figure 7B:
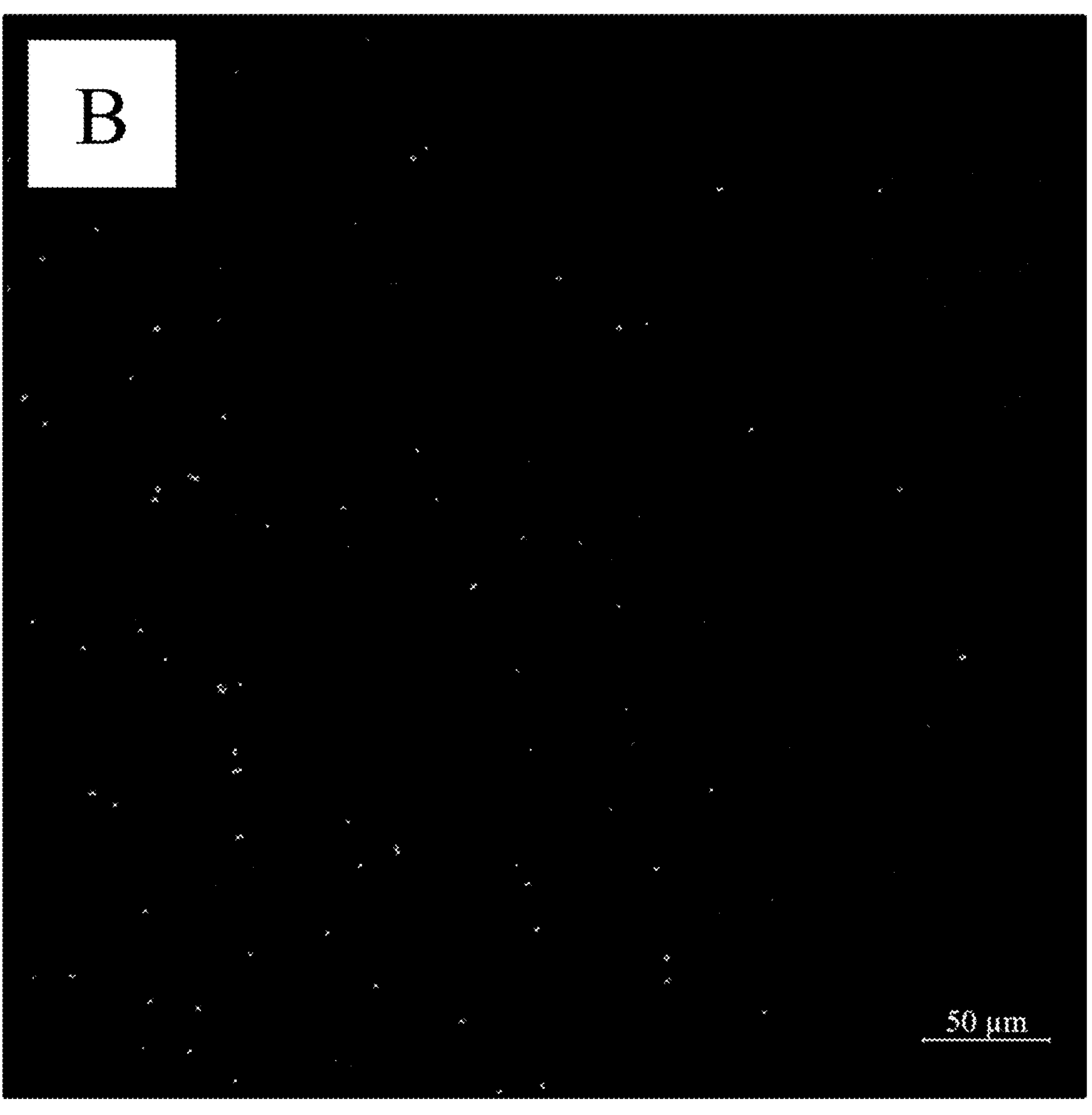
Figure 7C:
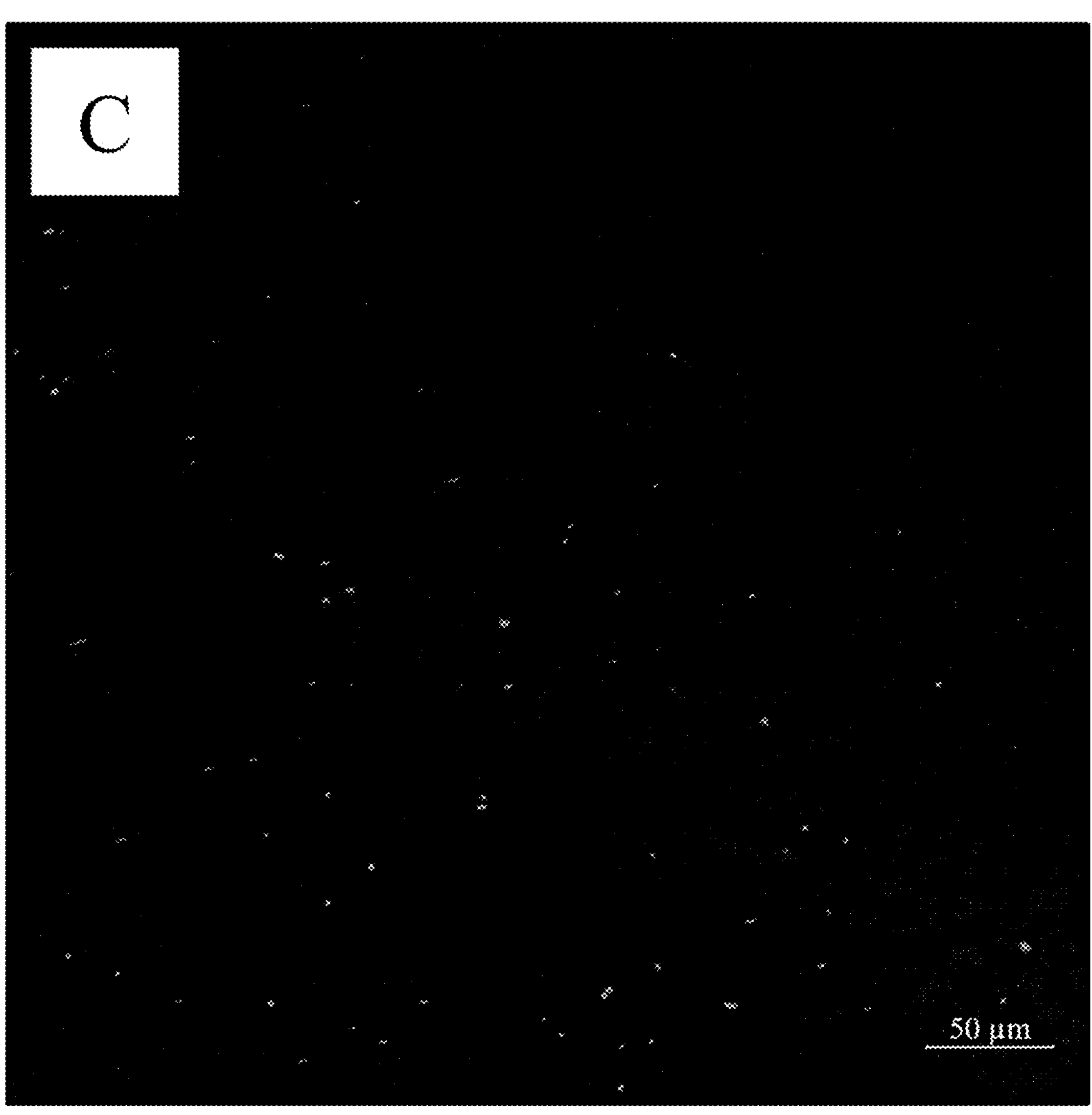
Figure 7D:
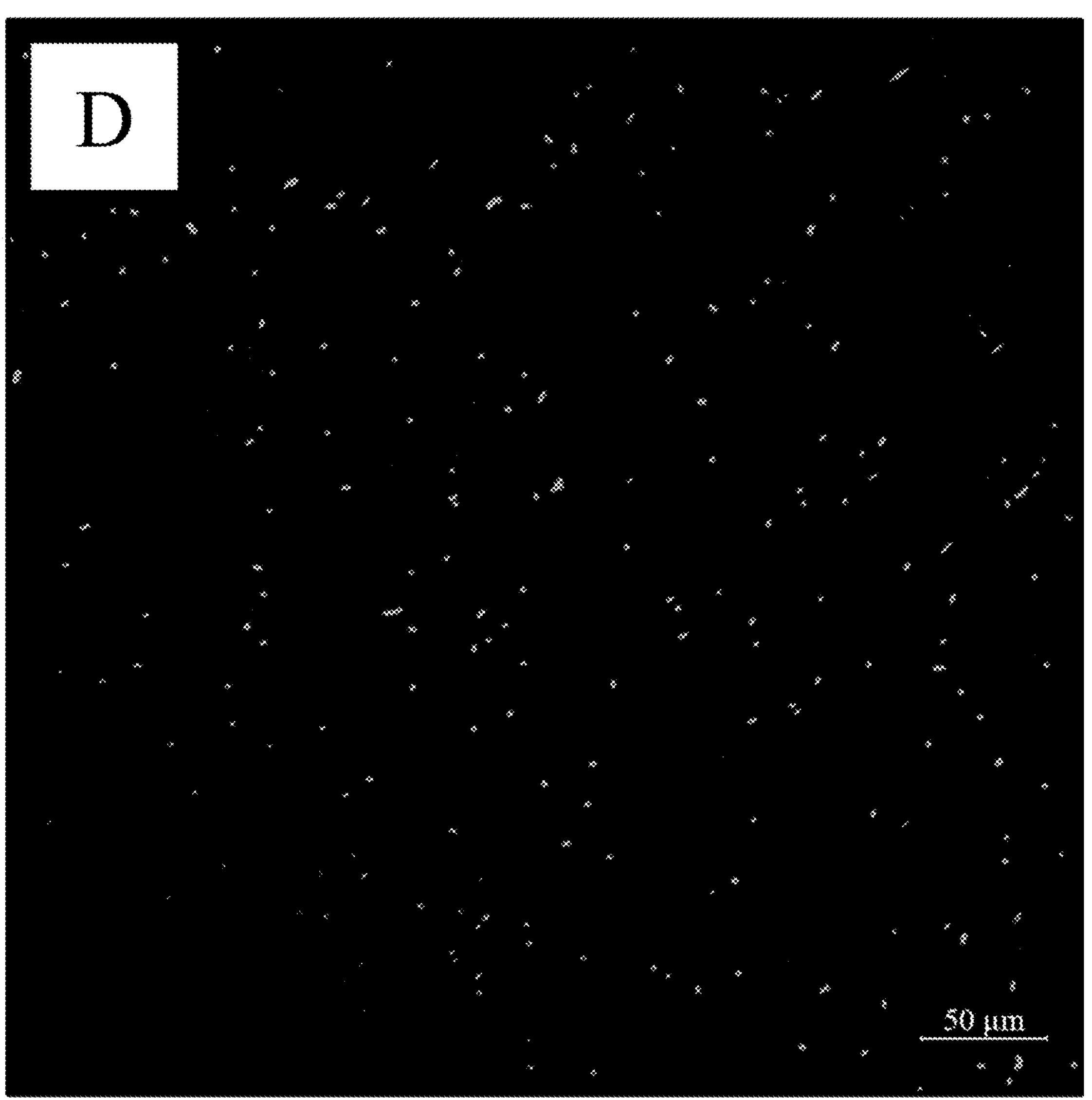
Figure 7E:
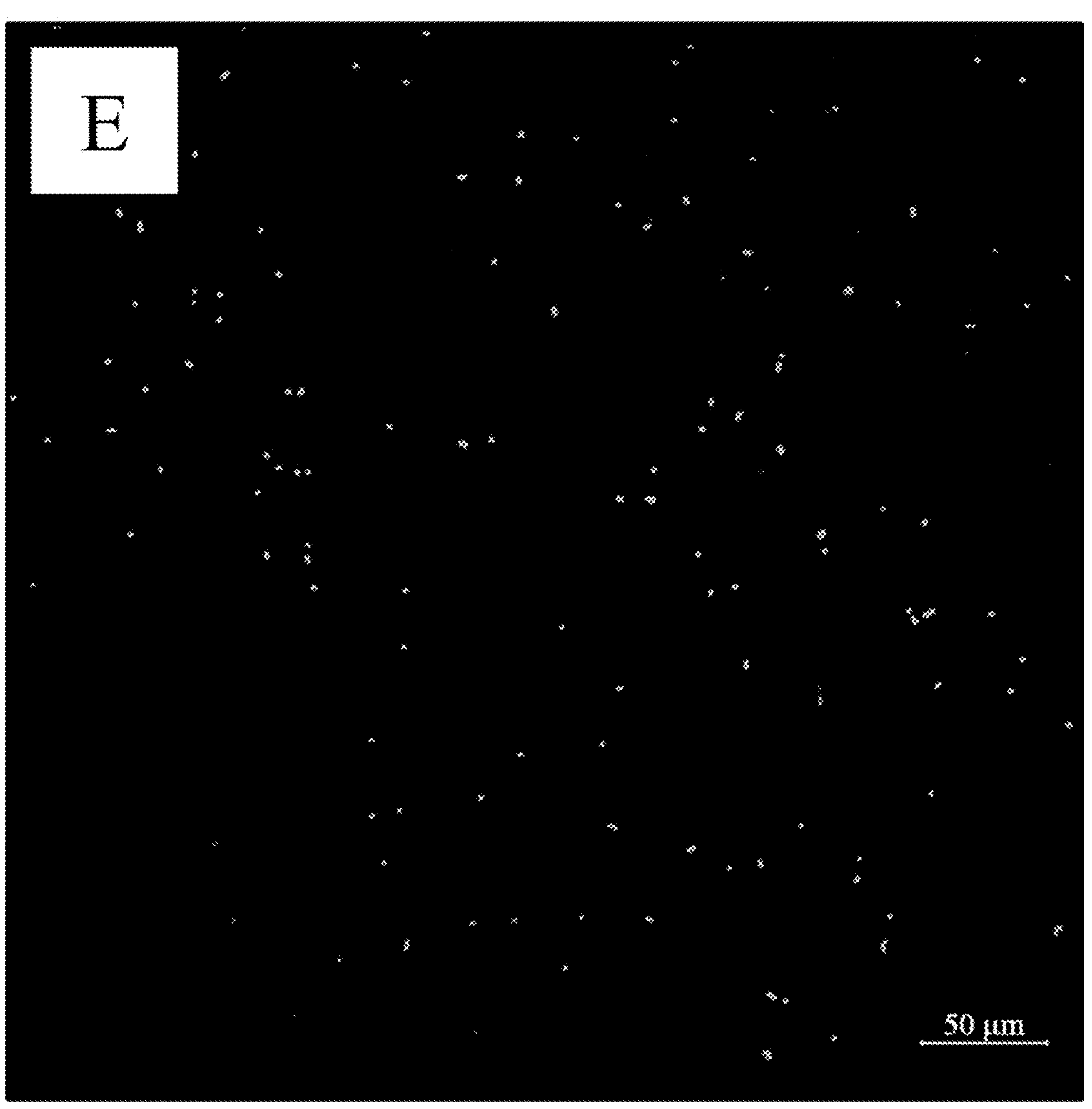
Figure 7F:
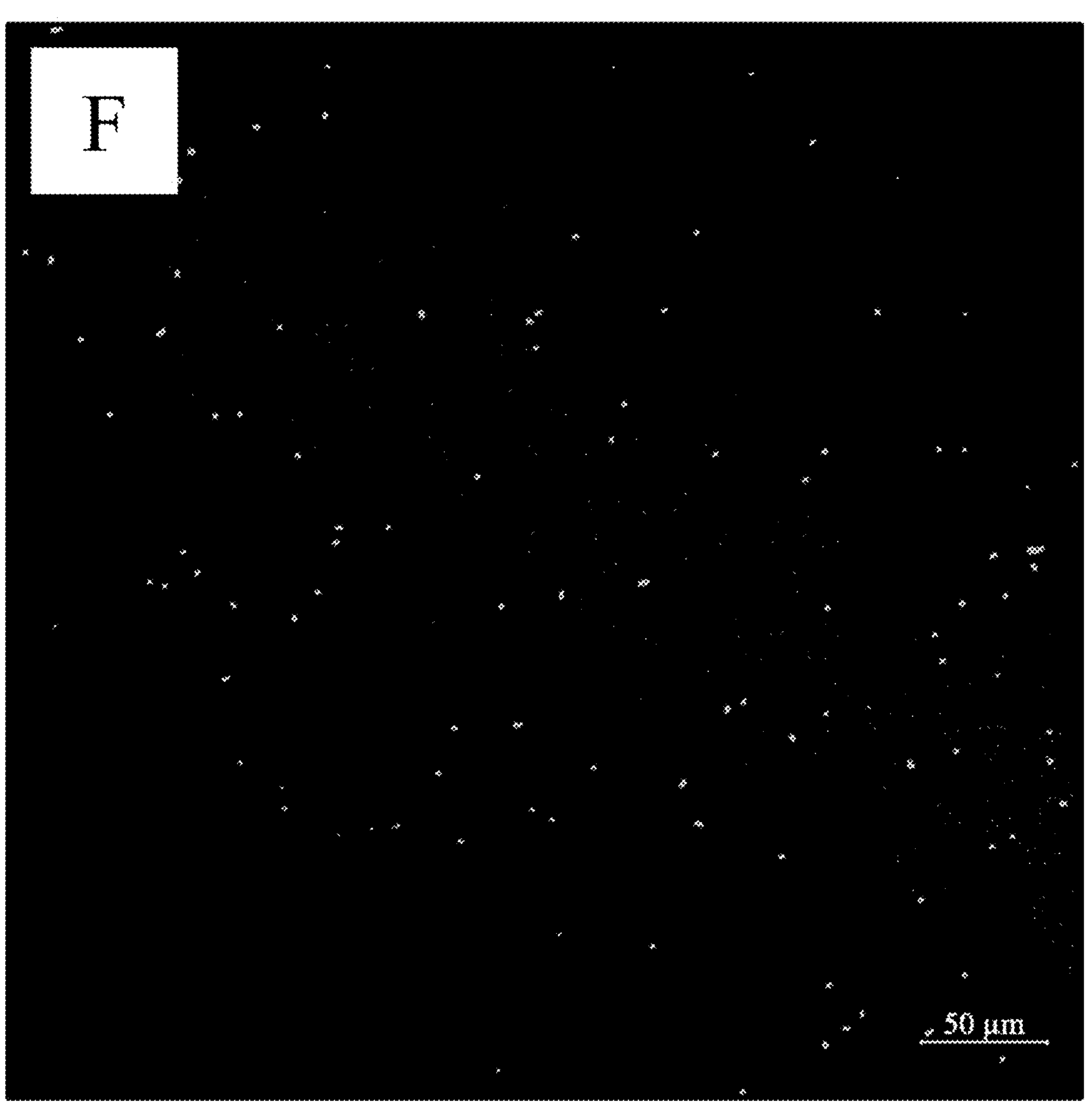
Figure 8A:
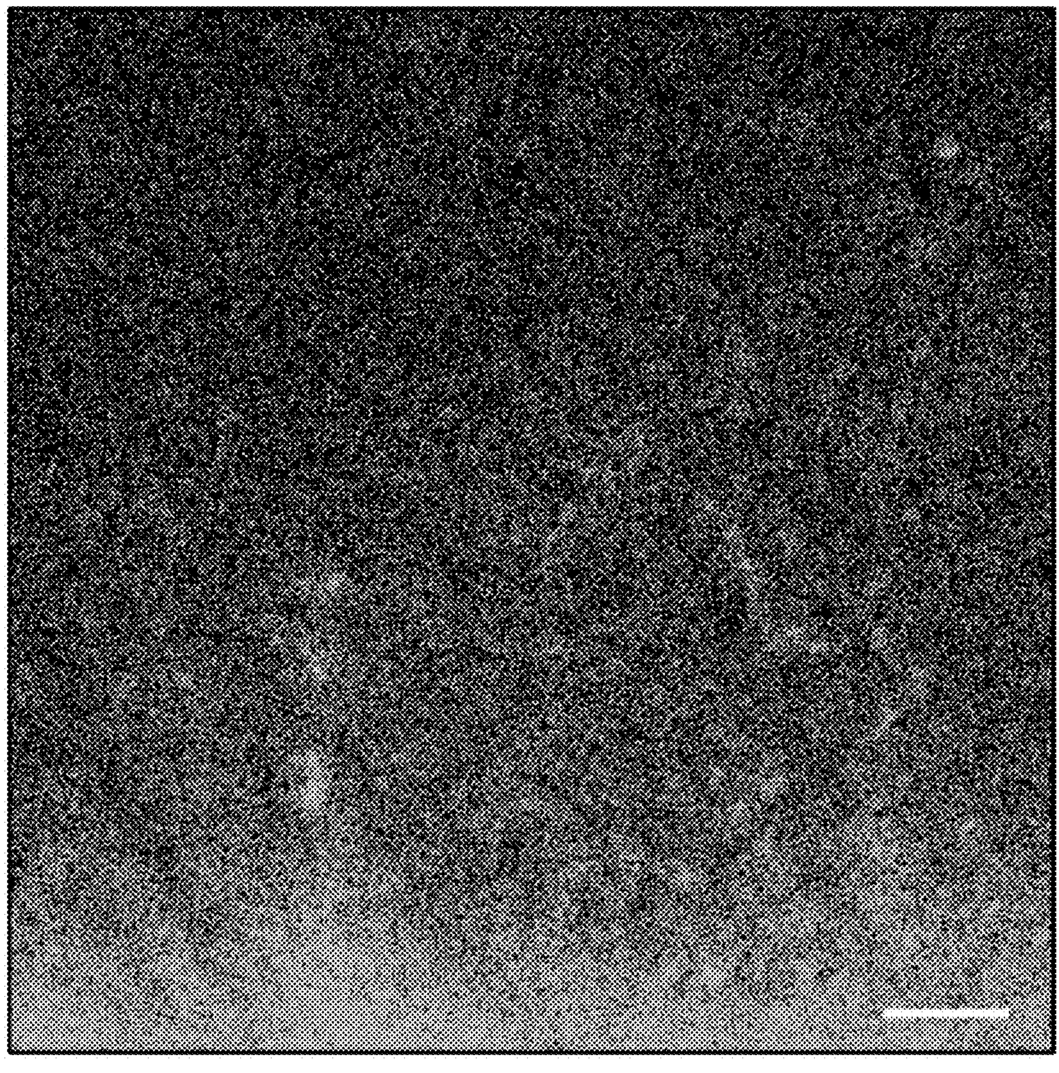
FIGS. 8A-8D. Fluorescence images of *S. mutans* by CLSM on various sample surfaces.
Figure 8B:
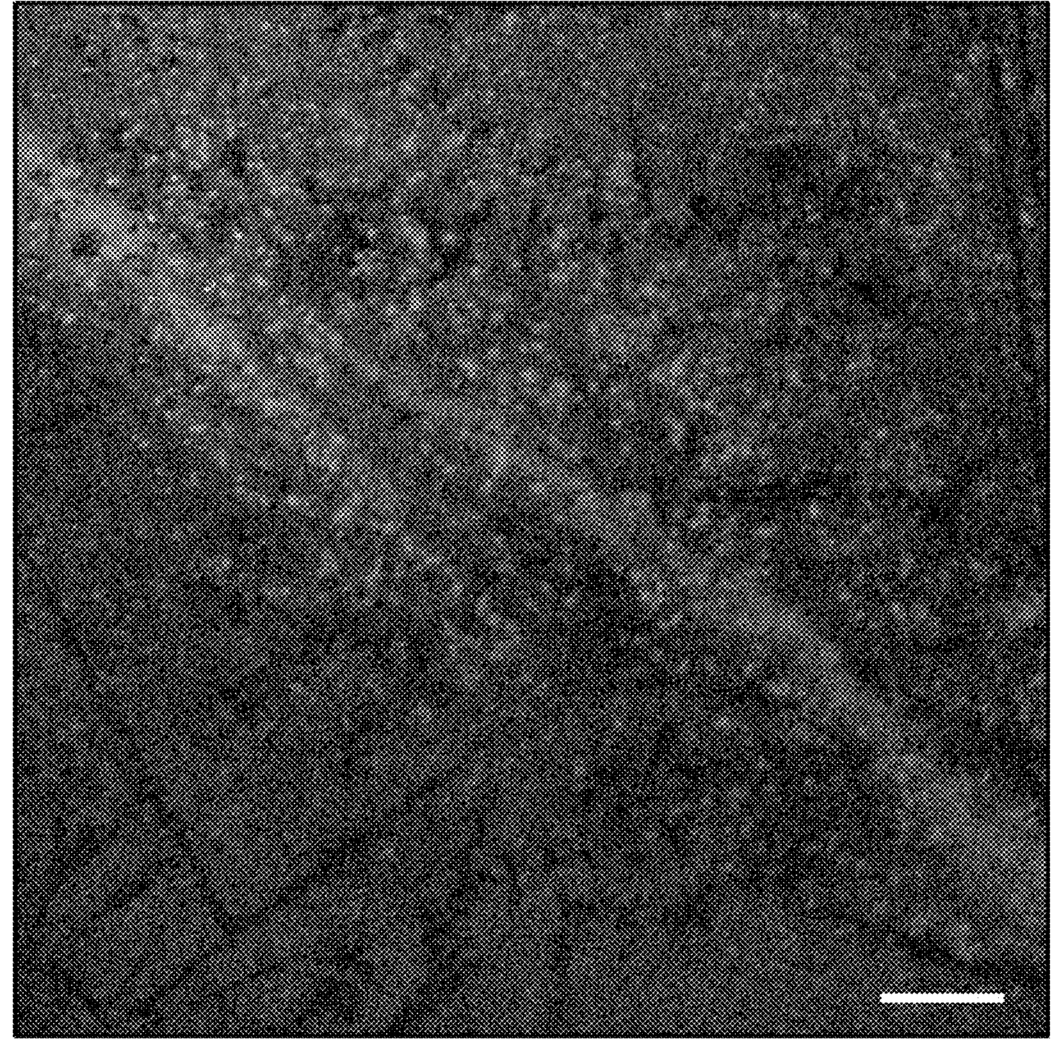
Figure 8C:
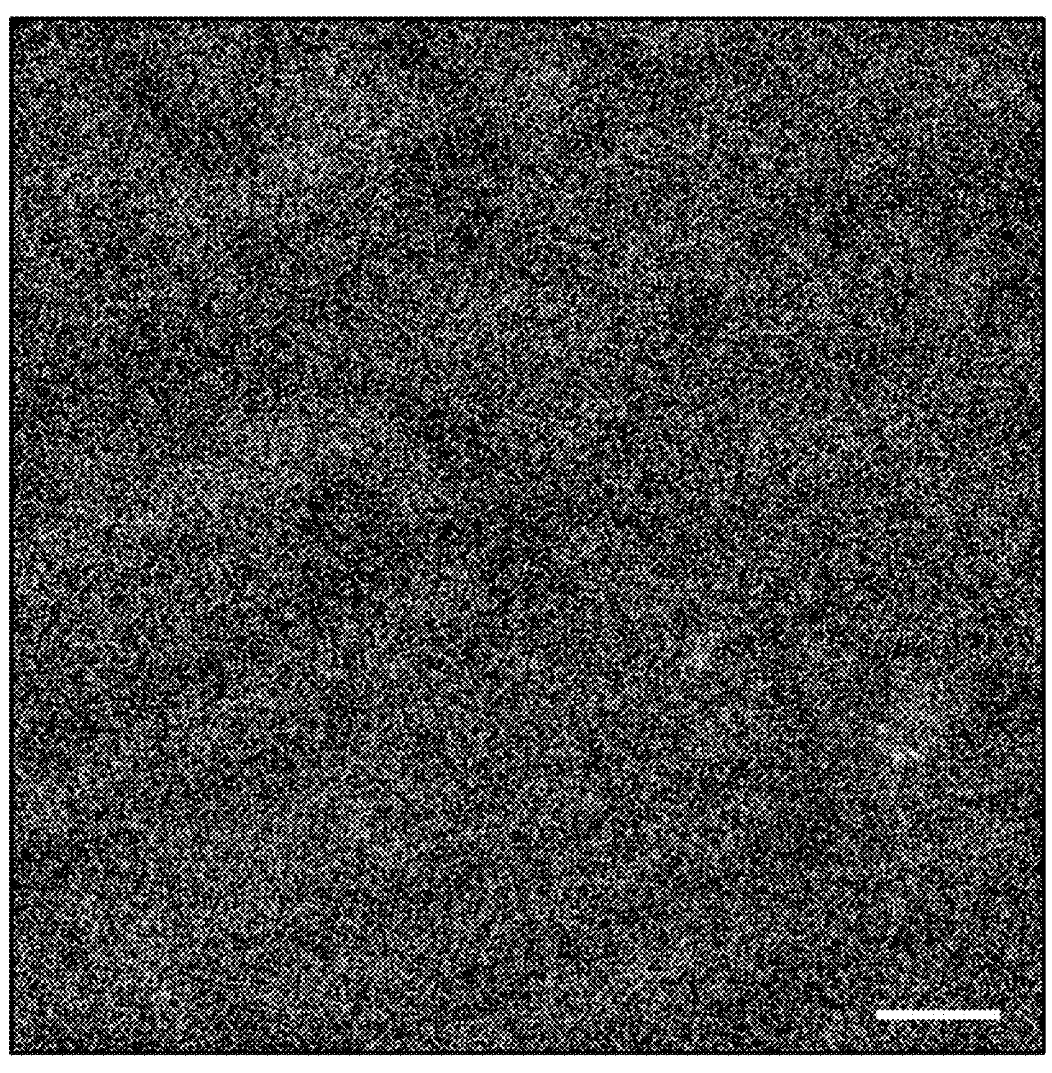
Figure 8D:
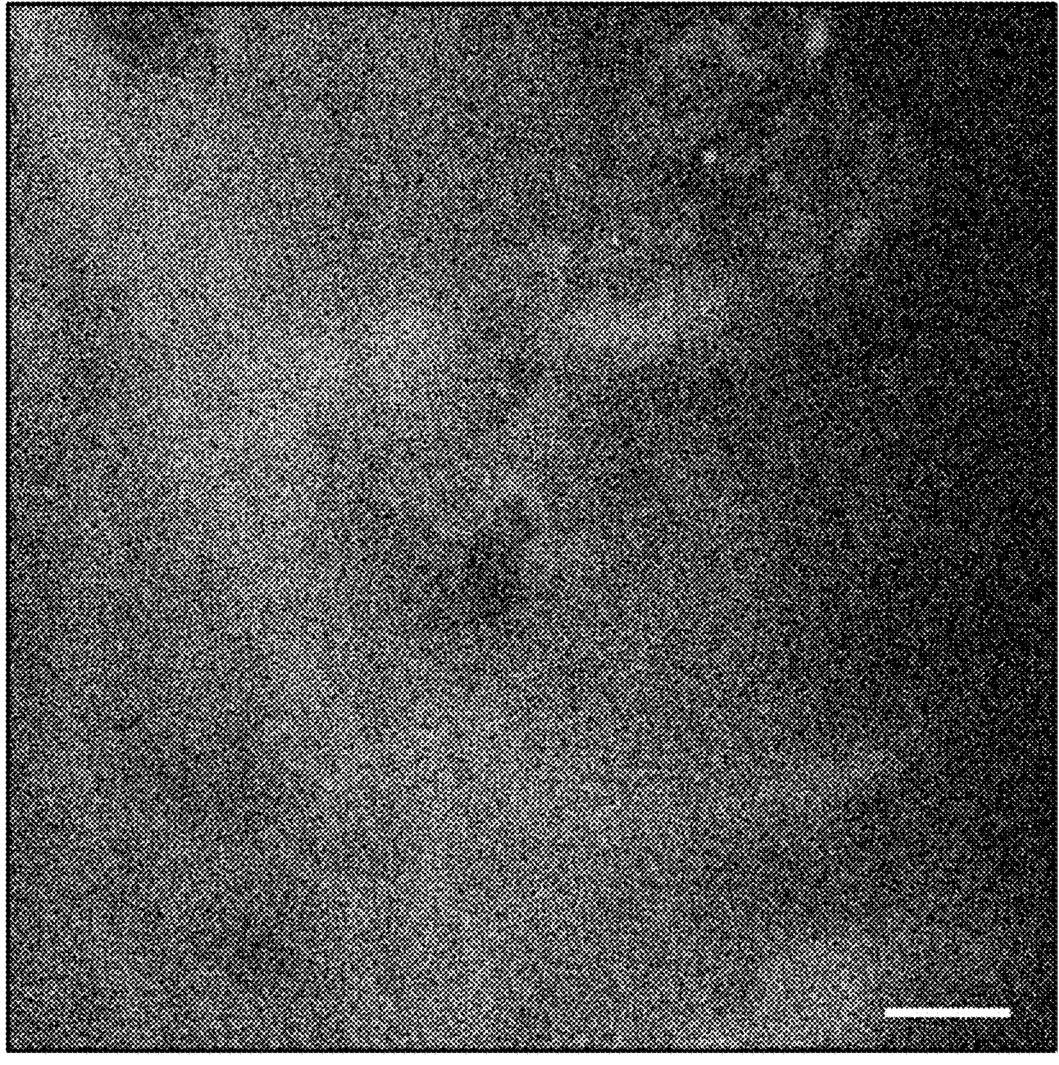
Figure 9A:
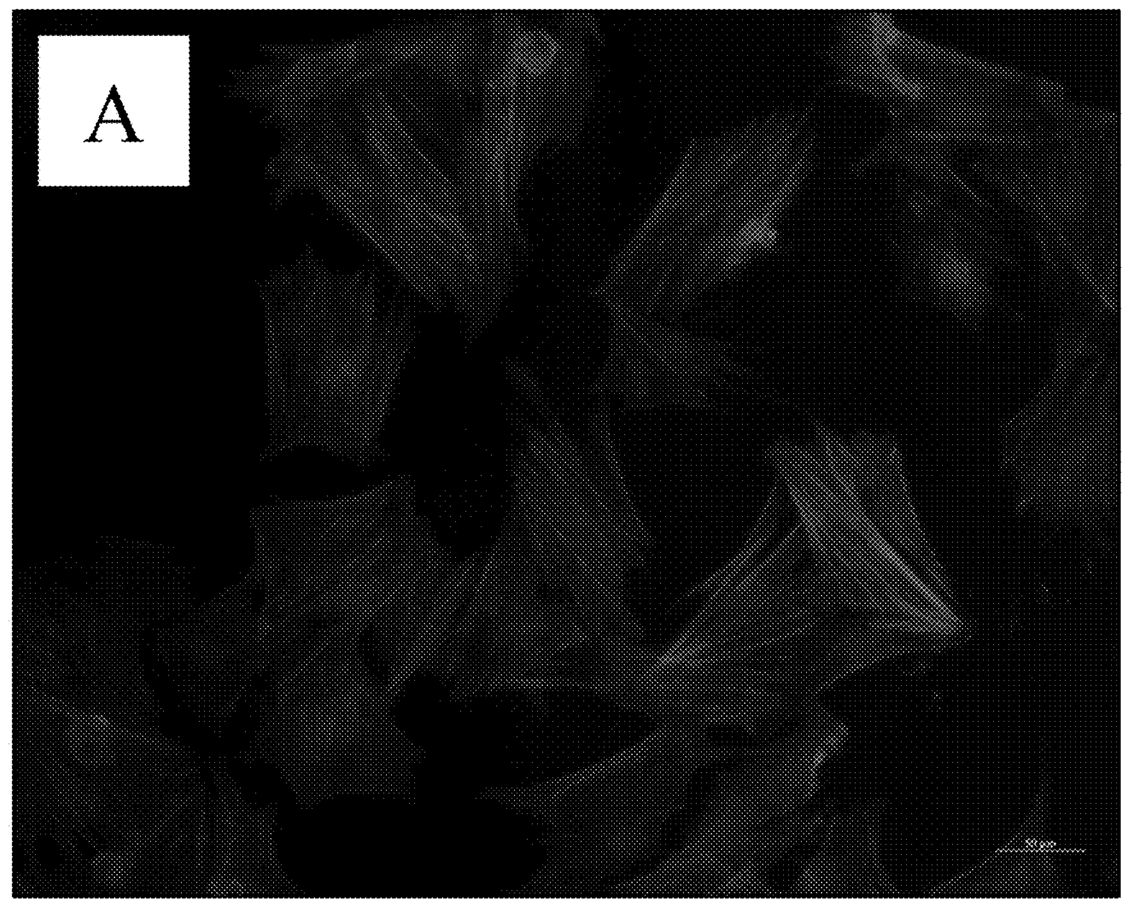
FIGS. 9A-9M. Cell morphology stained by 4',6-diamidino-2-phenylindole (DAPI) and phalloidine, and cell proliferation measured by CCK-8. Fluorescence images.
Figure 9B:
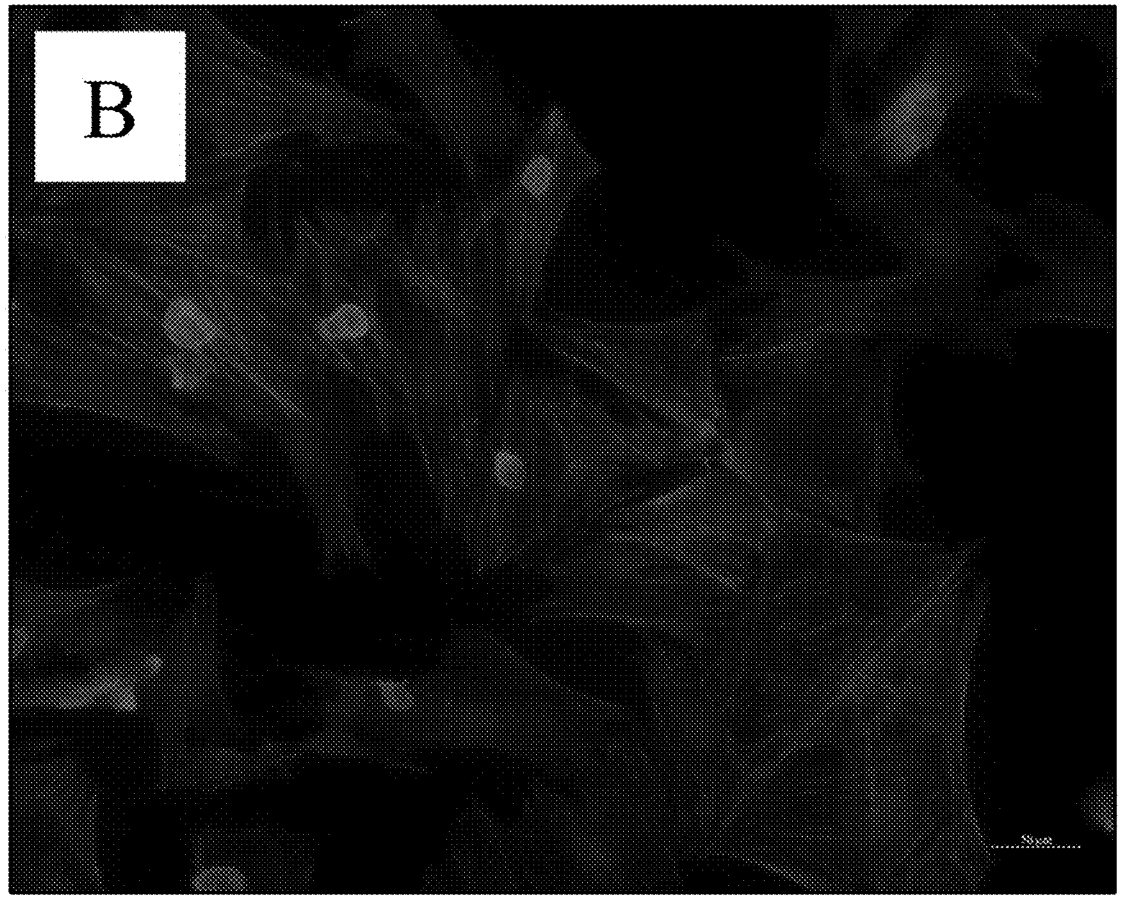
Figure 9C:
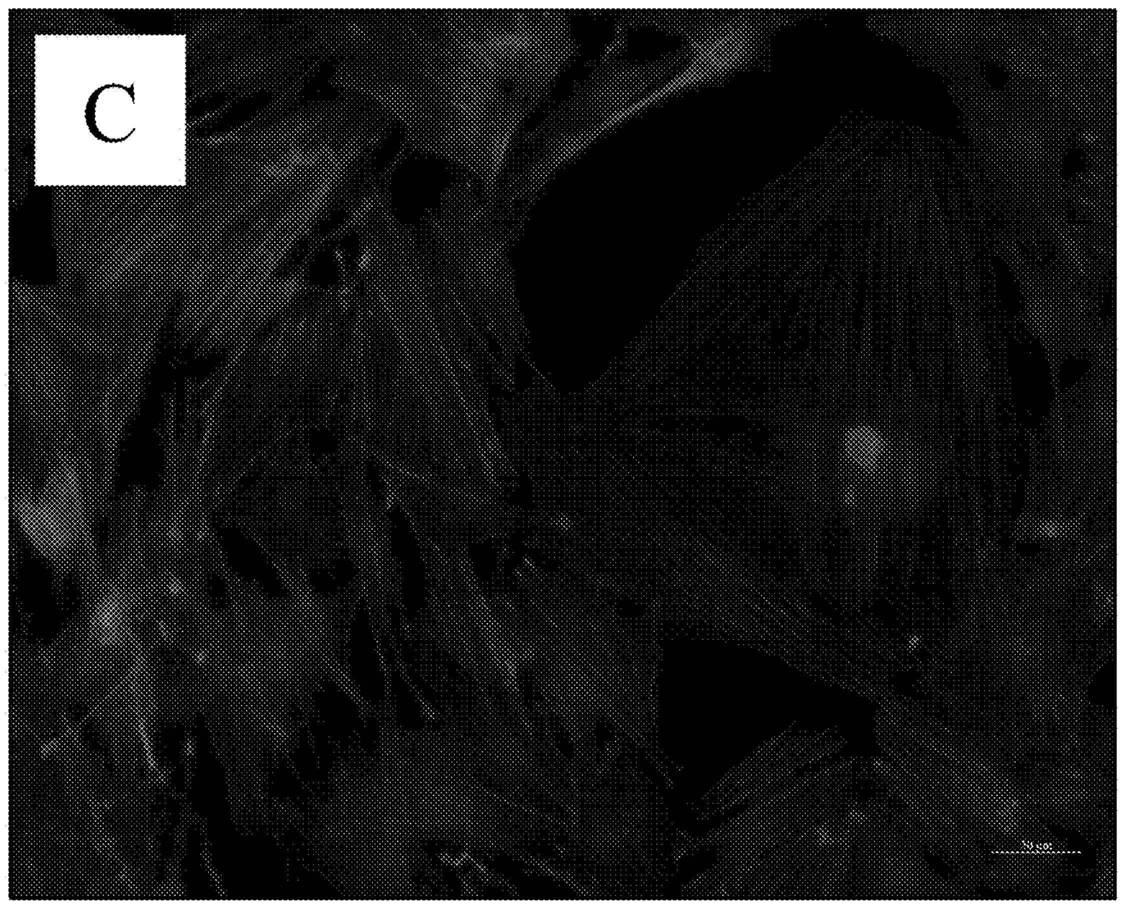
Figure 9D:
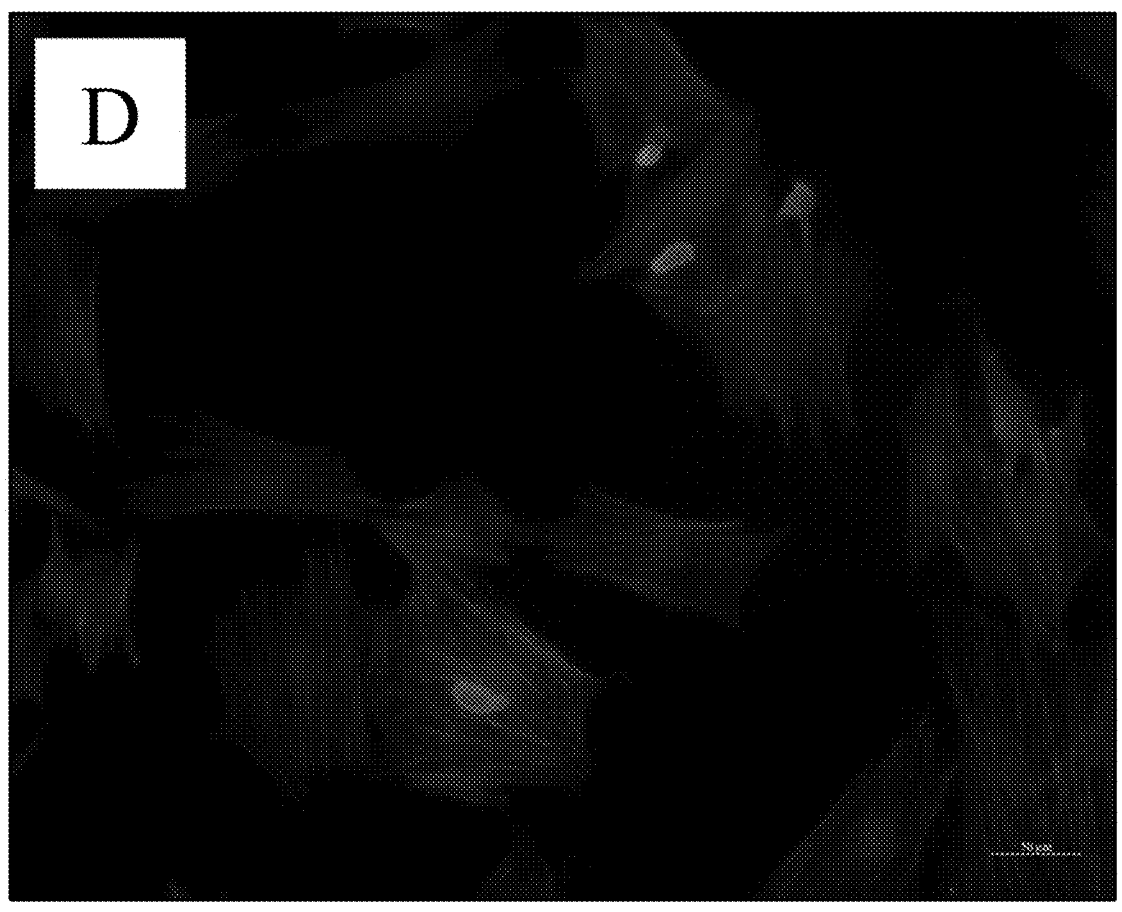
Figure 9E:
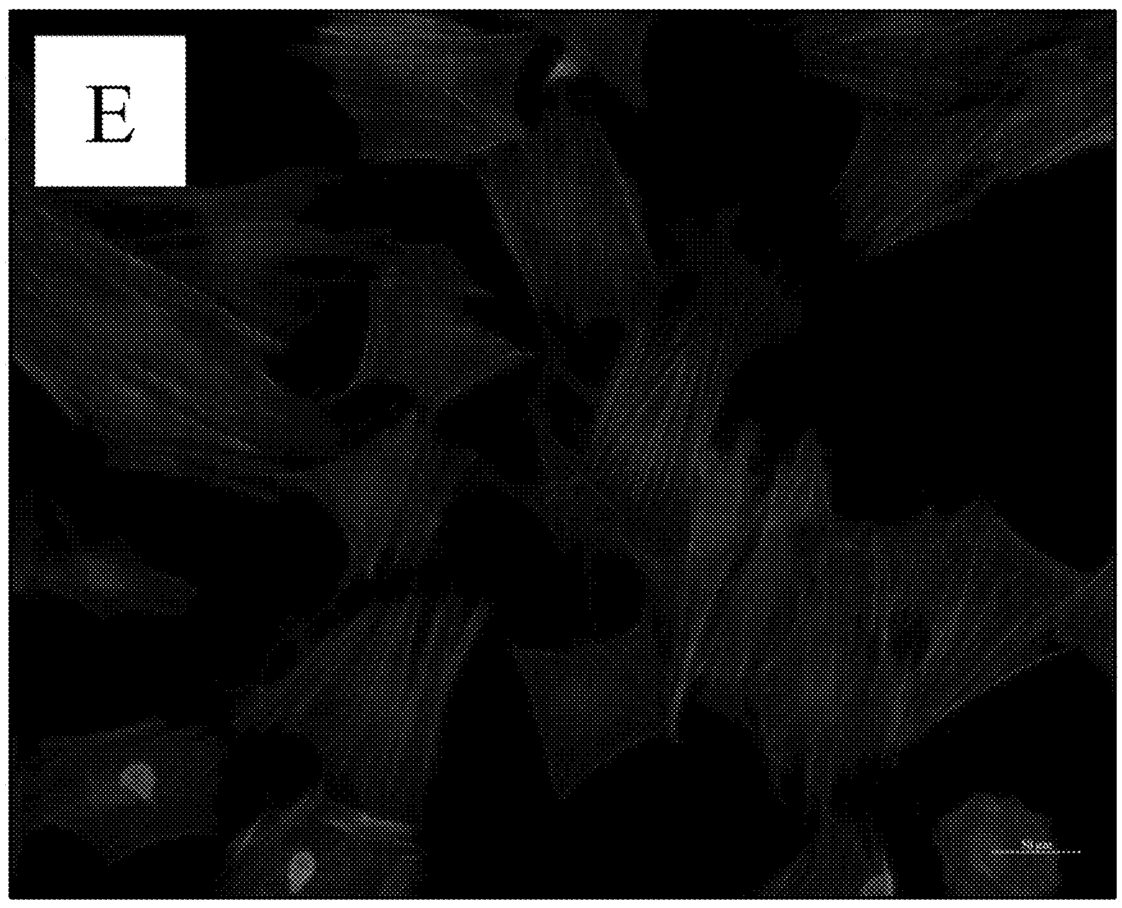
Figure 9F:
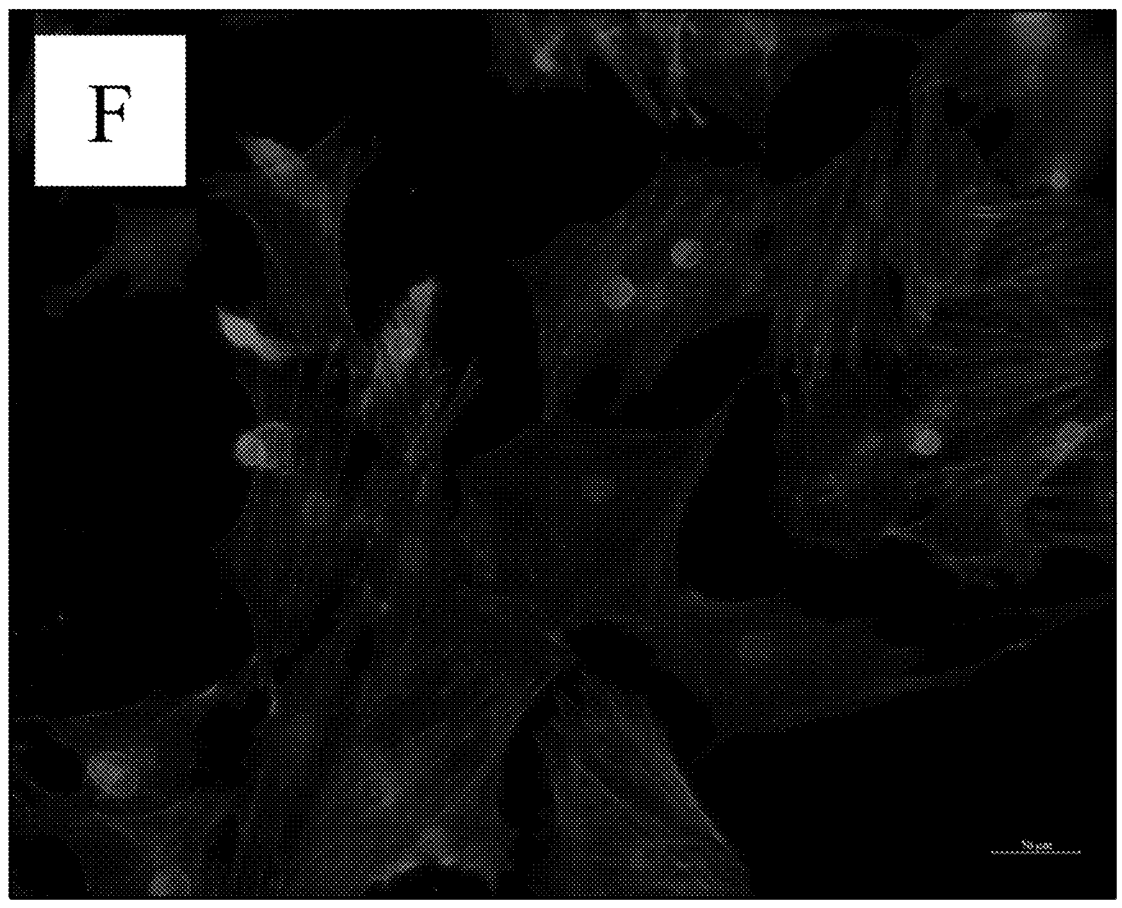
Figure 9G:
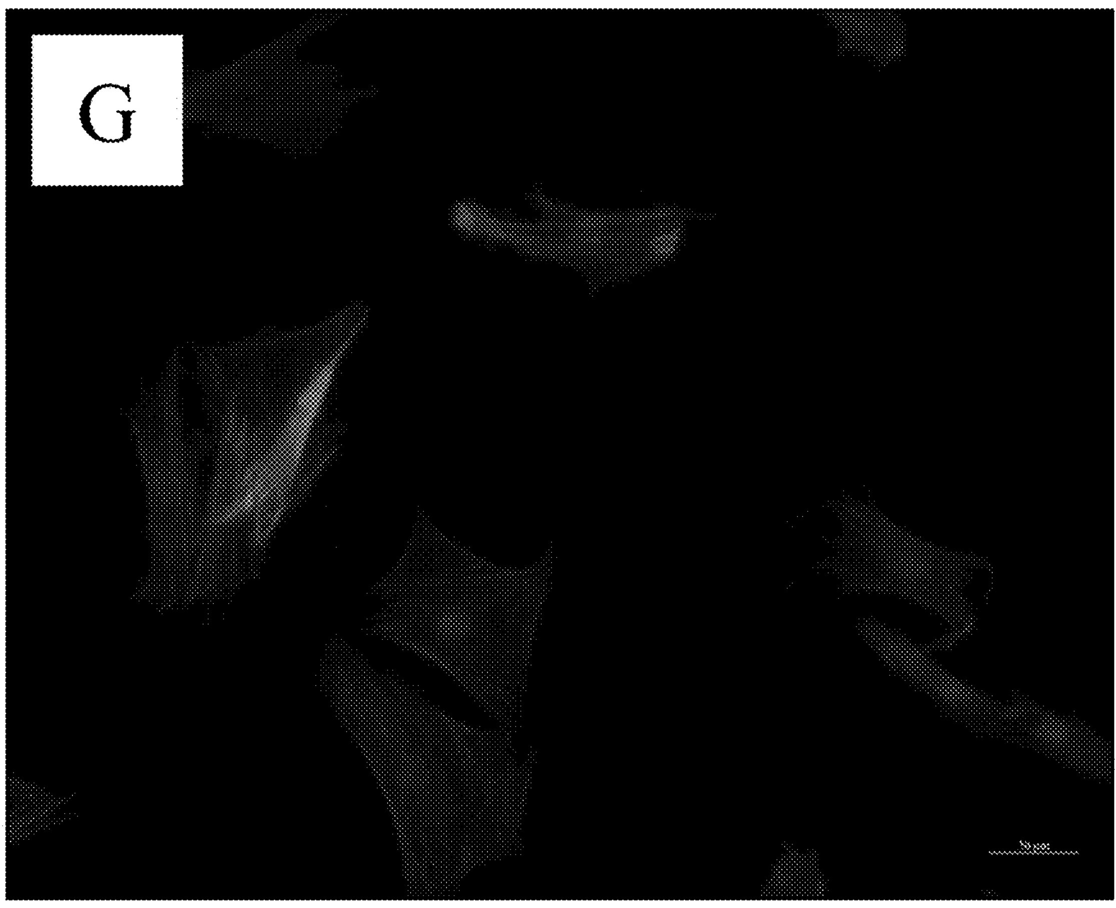
Figure 9H:
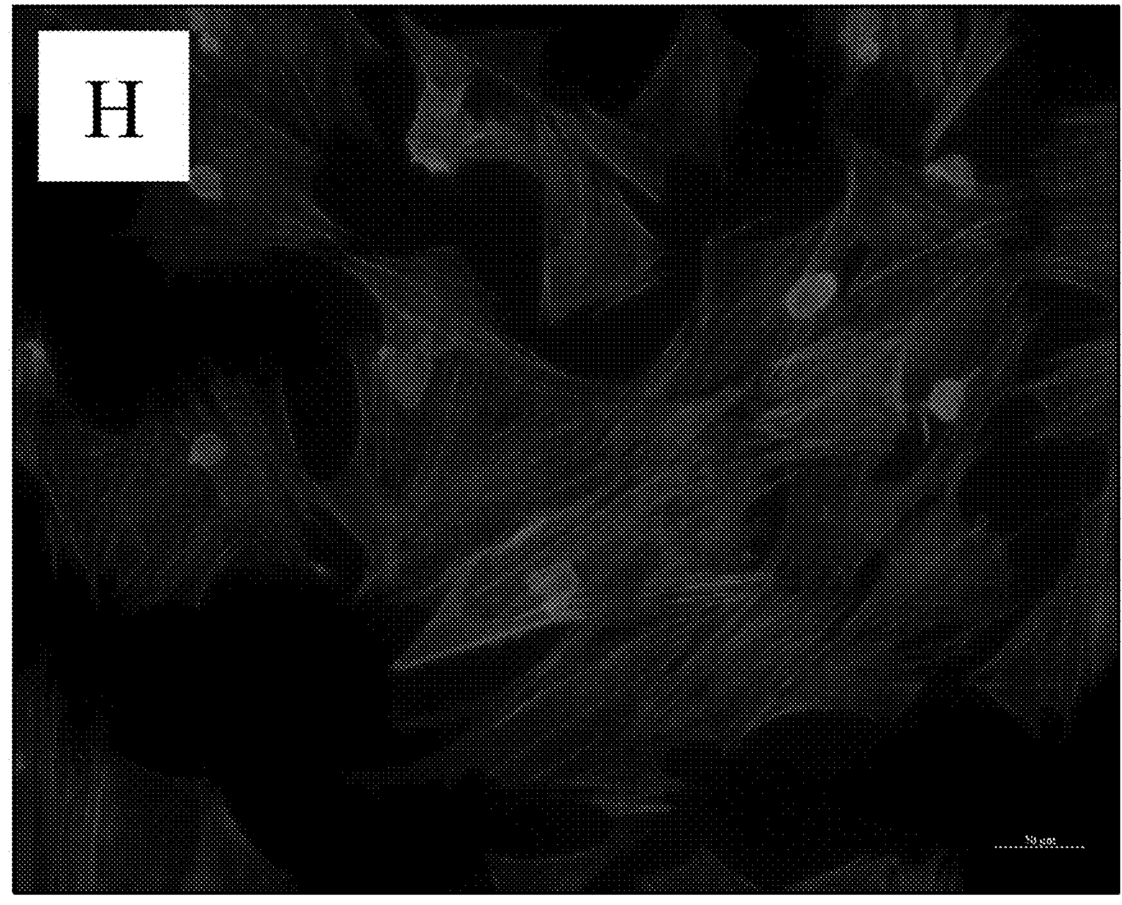
Figure 9I:
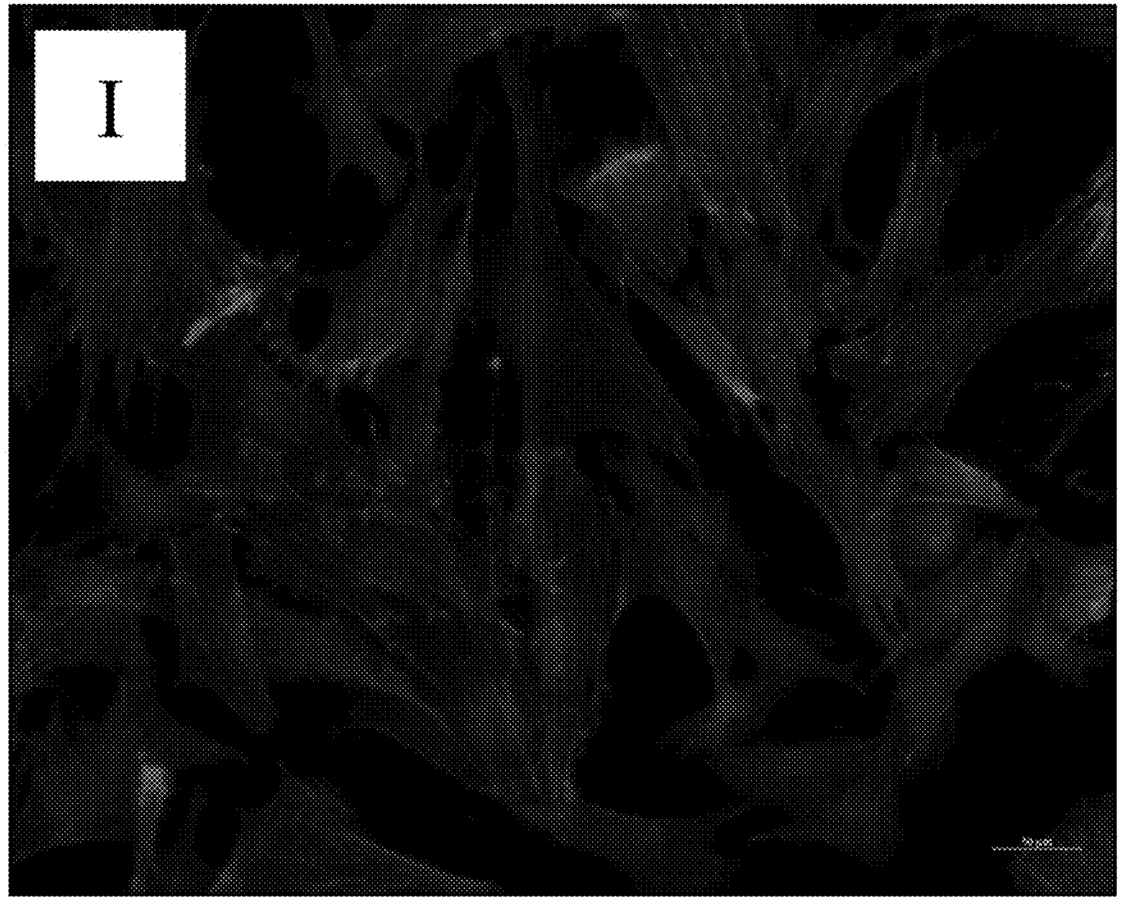
Figure 9J:
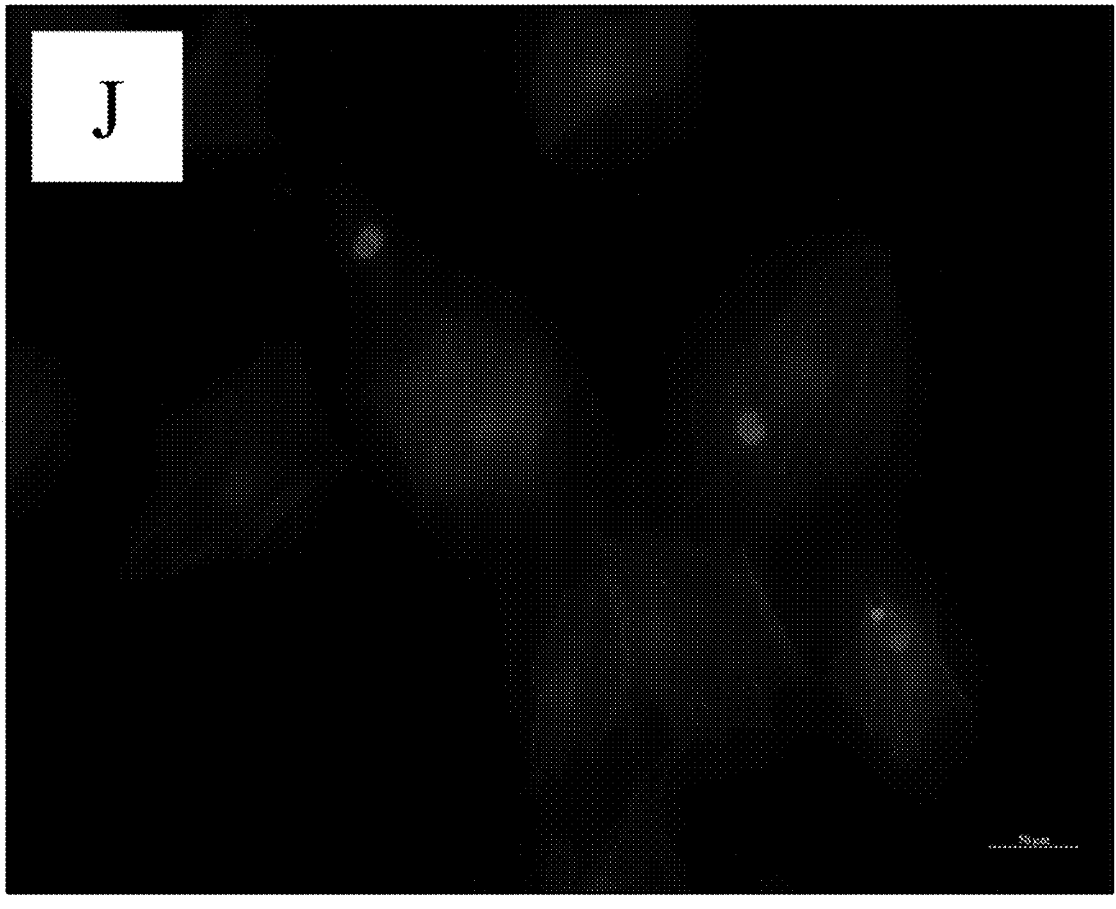
Figure 9K:
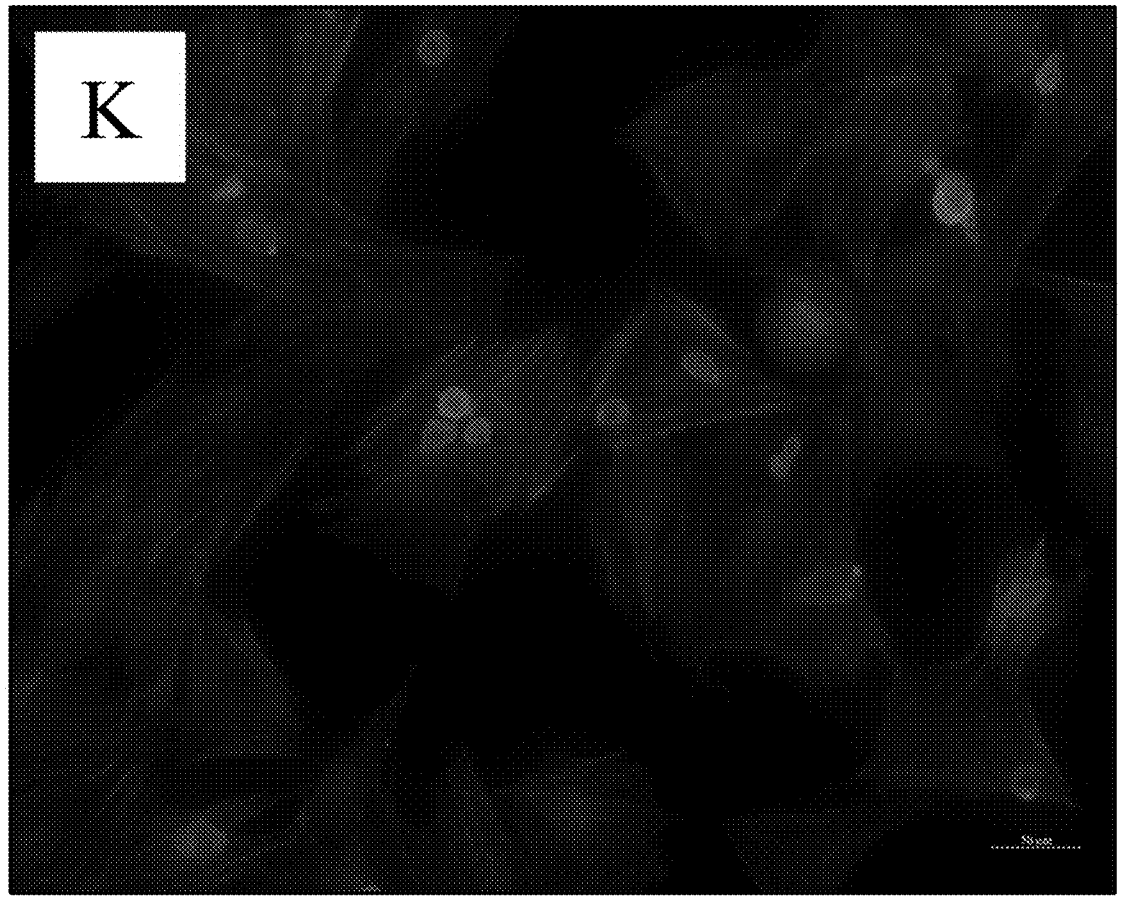
Figure 9L:
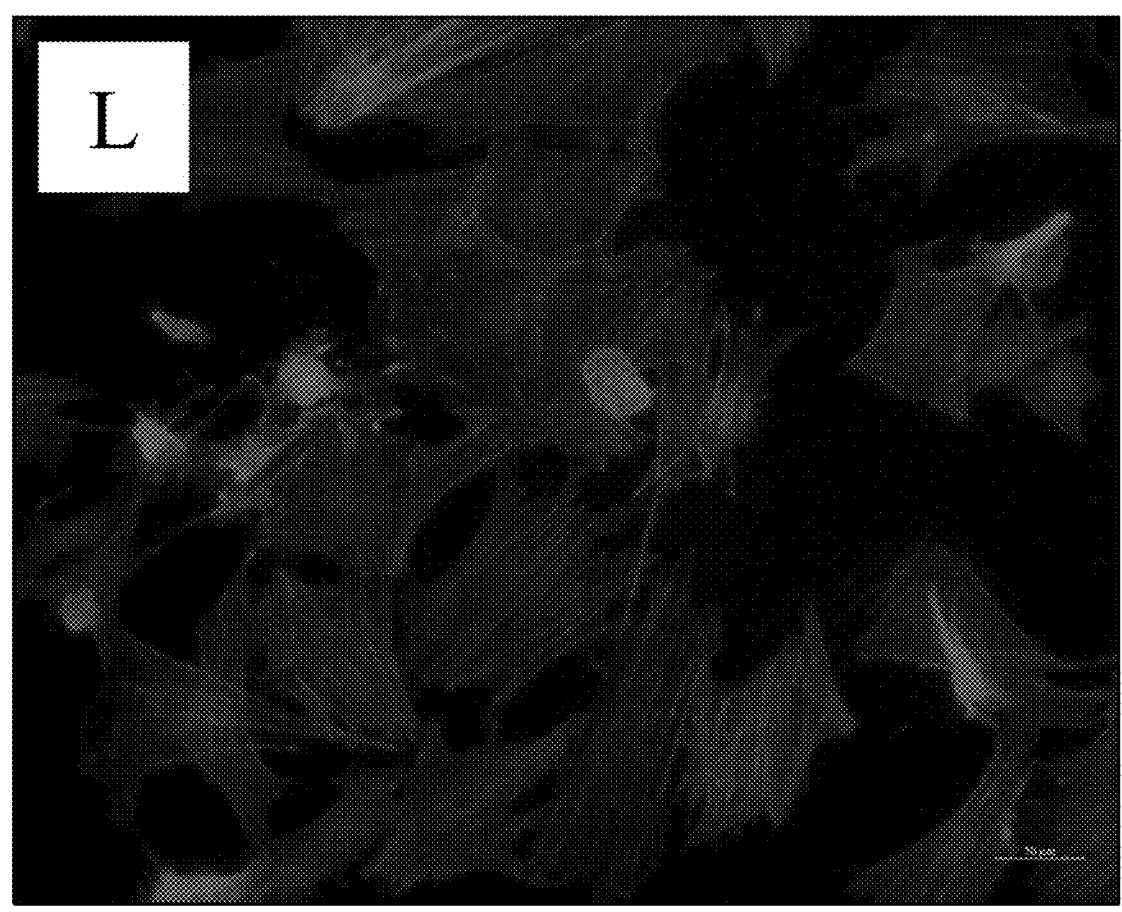
Figure 9M:
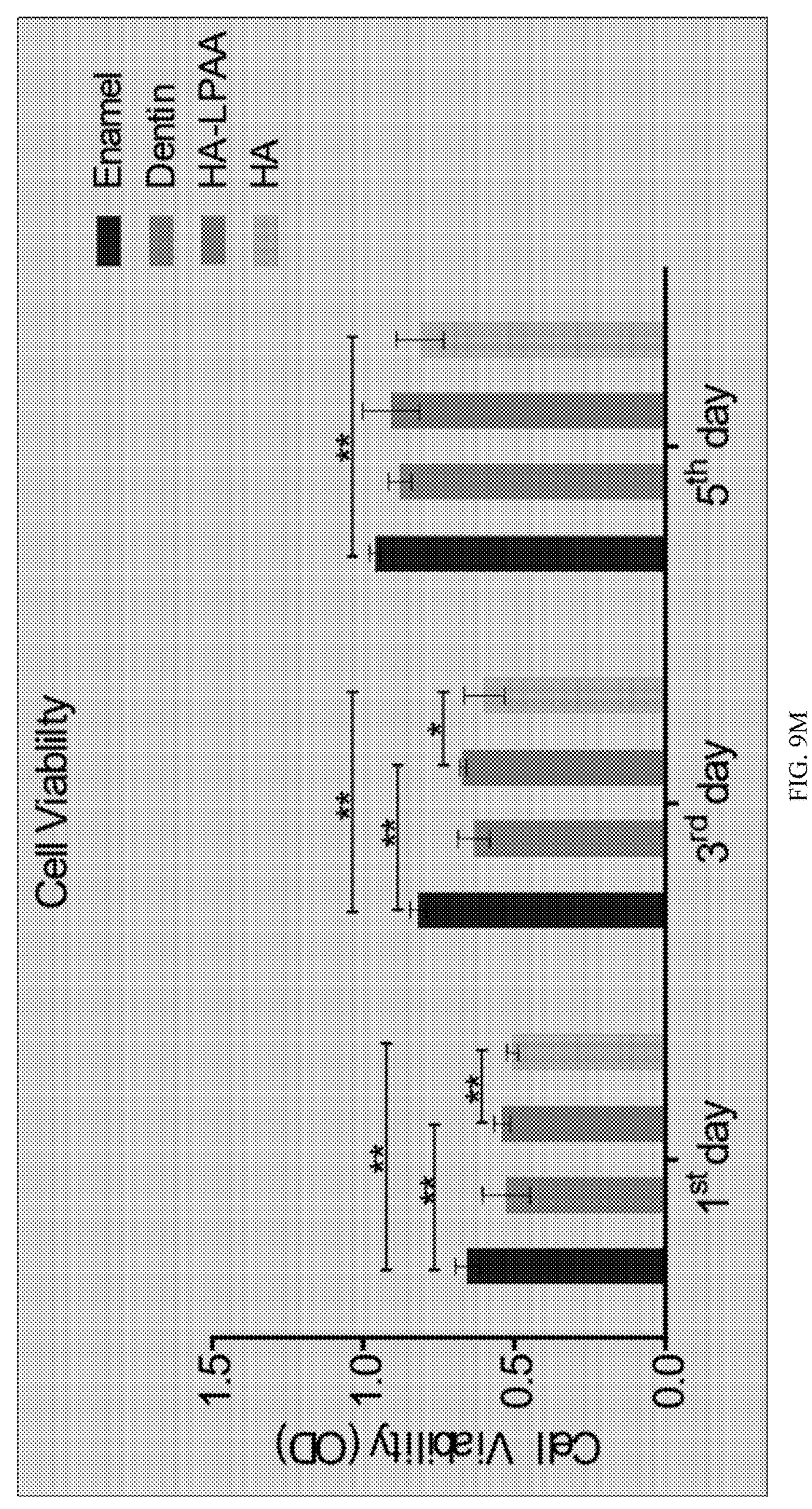
Figure 10:
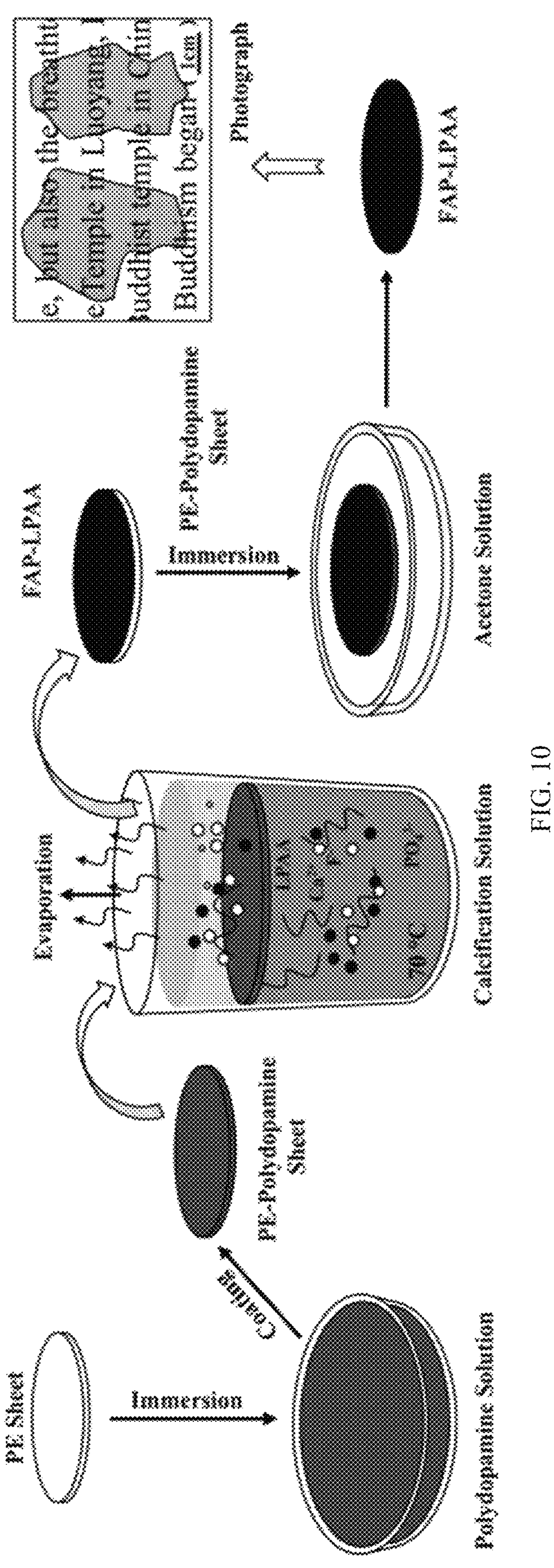

The compositions of the present invention comprise a mixture of FAP and LPAA in an antibacterial enamel-like structure generated by evaporation triggered deposition.

Selected Definitions

As used herein, the term "enamel-like" refers to a composite that has a similar microstructure, similar composition, and similar mechanical properties to tooth enamel.

The term "antibacterial", as used herein, refers to various forms of components, including a sheet or powder, that inhibit the growth and/or kill populations of bacteria.

The term "evaporation triggered deposition", as used herein, refers to an evaporation and crystal growth process triggered by a suitable temperature.

As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising". The transitional terms/phrases (and any grammatical variations thereof) "comprising", "comprises", "comprise", "consisting essentially of", "consists essentially of", "consisting" and "consists" can be used interchangeably.

The phrases "consisting essentially of" or "consists essentially of" indicate that the claim encompasses embodiments containing the specified materials or steps and those that do not materially affect the basic and novel characteristic(s) of the claim.

The term "about" means within an acceptable error range for the particular value as determined by one of ordinary skill in the art, which depends in part on how the value is measured, i.e., the limitations of the measurement system. In the context of compositions containing amounts of ingredients where the terms "about" is used, these compositions contain the stated amount of the ingredient with a variation (error range) of 0-10% around the value (X±10%). In other contexts the term "about" is provides a variation (error range) of 0-10% around a given value (X±10%). As is apparent, this variation represents a range that is up to 10% above or below a given value, for example, X±1%, X±2%, X±3%, X±4%, X±5%, X±6%, X±7%, X±8%, X±9%, or X±10%.

In the present disclosure, ranges are stated in shorthand to avoid having to set out at length and describe each and every value within the range. Any appropriate value within the range can be selected, where appropriate, as the upper value, lower value, or the terminus of the range. For example, a range of 0.1-1.0 represents the terminal values of 0.1 and 1.0, as well as the intermediate values of 0.2, 0.3, 0.4, 0.5, 0.6, 0.7, 0.8, 0.9, and all intermediate ranges encompassed within 0.1-1.0, such as 0.2-0.5, 0.2-0.8, 0.7-1.0, etc. Values having at least two significant digits within a range are envisioned, for example, a range of 5-10 indicates all the values between 5.0 and 10.0 as well as between 5.00 and 10.00 including the terminal values. When ranges are used herein, combinations and subcombinations of ranges (e.g., subranges within the disclosed range) and specific embodiments therein are explicitly included.

As used herein, the term "subject" refers to an animal, needing or desiring delivery of the benefits provided by a therapeutic composition. The animal may be for example, humans, pigs, horses, goats, cats, mice, rats, dogs, apes, fish, chimpanzees, orangutans, guinea pigs, hamsters, cows, sheep, birds, chickens, as well as any other vertebrate or invertebrate. These benefits can include, but are not limited to, the treatment of a health condition, disease or disorder; prevention of a health condition, disease or disorder; immune health; enhancement of the function of enamel, an organ, tissue, or system in the body. The preferred subject in the context of this invention is a human. The subject can be of any age or stage of development, including infant, toddler, adolescent, teenager, adult, or senior.

As used herein, the terms "therapeutically-effective amount," "therapeutically-effective dose," "effective amount," and "effective dose" are used to refer to an amount or dose of a compound or composition that, when administered to a subject, is capable of treating or improving a condition, disease, or disorder in a subject or that is capable of providing enhancement in health or function to an organ, tissue, or body system. In other words, when administered to a subject, the amount is "therapeutically effective." The actual amount will vary depending on a number of factors including, but not limited to, the particular condition, disease, or disorder being treated or improved; the severity of the condition; the particular organ, tissue, or body system of which enhancement in health or function is desired; the weight, height, age, and health of the patient; and the route of administration.

As used herein, the term "treatment" refers to eradicating, reducing, ameliorating, or reversing a sign or symptom of a health condition, disease or disorder to any extent, and includes, but does not require, a complete cure of the condition, disease, or disorder. Treating can be curing, improving, or partially ameliorating a disorder. "Treatment" can also include improving or enhancing a condition or characteristic, for example, bringing the function of a particular system in the body to a heightened state of health or homeostasis.

As used herein, "preventing" a health condition, disease, or disorder refers to avoiding, delaying, forestalling, or minimizing the onset of a particular sign or symptom of the condition, disease, or disorder. Prevention can, but is not required, to be absolute or complete; meaning, the sign or symptom may still develop at a later time. Prevention can include reducing the severity of the onset of such a condition, disease, or disorder, and/or inhibiting the progression of the condition, disease, or disorder to a more severe condition, disease, or disorder.

By "reduces" is meant a negative alteration of at least 1%, 5%, 10%, 25%, 50%, 75%, or 100%.

By "increases" is meant as a positive alteration of at least 1%, 5%, 10%, 25%, 50%, 75%, or 100%.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Preparation of Fluorapatite (FAP) Compositions

In certain embodiments, generation of enamel-like FAP ($Ca_5(PO_4)_3F$) can be performed using a novel evaporation strategy. In certain embodiments, a polymer plate, such as, for example, a PS plate, a polypropylene plate, or any other polymer that is stable in water at 70° C. but can be easily dissolved by organic solvents, such, as, for example, acetone or isoamyl acetate, can be used as a removable substrate for the continuous growth of FAP. In certain embodiments, the polymer plate can be immersed in a polydopamine solution or other solutions that have phenolic hydroxyl groups at a concentration of about 2 mg/ml. The immersion can last for at least 24 hours, 36 hours, 48 hours, or longer. Plastic foams can be fixed on polydopamine-activated polymer plates via PE wires to provide additional buoyancy force for the polymer plate to ensure a constant distance of about 3 mm from the polymer plate to the liquid surface when the polymer plate can then be placed into a calcification solution.

In certain embodiments, a fluorine ion at a concentration of about 0.1 mmol/L to about 10 mmol/L, about 1 mmol/L to about 5 mmol/L, or about 1.17 mmol/L can be added into calcification solution for the generation of enamel-like FAP with improved resistance of teeth to acid erosion caused acid produced by bacteria. Meanwhile, LPAA at a concentration of about 25 mg/L can be applied to modulate the crystal growth process of the enamel-like FAP structure. In certain embodiments, the crystals form a prism-like structure. The calcification solution can be incubated at about 70° C. for rapid evaporation and refreshed at least every 1 hour, 2 hours, 3 hours, 4 hours, 5, hours, 6 hours, 7 hours, 8 hours, 9 hours, 10 hours, 11 hours, 12 hours 15 hours, 18 hours, 24 hours or 36 hours. Replacing the evaporated solution replenishes calcium ions, phosphate groups, fluorine ions, LPAA molecules, and water. The frequency of replenishing the solution can be determined by the evaporation rate of the solution, which can be altered based on the temperature of the solution or size of the container relative to the surface area of the solution. For example, if the calcification solution is processed in a larger-capacity beaker, such as, for example, larger than 250 mL, the solution may not need to be refreshed for at least 12 hours. In certain embodiments, the LPAA can be added into the calcification solution before the refreshed solution can be added into the beaker. When the mineralization process ends, the FAP-LPAA ($Ca_5(PO_4)_3F—(C_3H_4O_2)_n$) sheet on the polymer surface can be separated from the polymer surface by dissolving polymer sheet with a solvent, such as, for example, acetone or isoamyl acetate. The mineralization time depends on the needed thickness of the enamel-like FAP. The thicker enamel-like structure that is needed, the longer time of mineralization will be needed. For example, when the designed thickness of the enamel-like structure is about 100 μm, the time needed can be about 1 day to about 60 days, about 14 days to about 40 days, or about 30 days.

In certain embodiments, the FAP-LPAA composition comprises, for example, a concentration of FAP of at least about 80%, about 90%, about 92%, about 93%, about 94%, about 95%, about 96%, or, preferably, about 97%. In certain embodiments, the FAP-LPAA composition comprises, for example, a concentration of LPAA of at about 1% to about 20%, about 2% to about 15%, about 3% to about 10%, or, preferably, about 5%.

The antibacterial agent useful in the compositions of the present invention includes LPAA having a mass average molecular weight of 3,000. The antibacterial ability of graphene oxide was significantly better than that of unoxidized graphene. Therefore, We deduced that the antibacterial mechanism of LPAA, similar to graphene oxide, benefited from the carboxyl group.

Additionally, LPAA can bind to alkali metal ions by repeated carboxy group. Therefore, the LPAA can bind to FAP by carboxy group.

In certain embodiments, the concentration of LPAA used in the present calcification solution is about 25 mg/L. And the mass ratio in the enamel-like FAP-LPAA composite is about 3%, similar to the organic content ratio in dental enamel.

In certain embodiments, a poly-dopamine activated surface, including a polystyrene surface, can induce an uniform and dense nucleation of FAP. Poly-dopamine can bind to LPAA chains by its carboxy group, thus can generate uniform and dense nucleation sites. These nucleation sites can promote the parallel arrangement of crystals and generate enamel-like structure finally. Without poly-dopamine activation, supersaturation of calcium and phosphate ions can only lead to isolated crystals on the substrate and lead to gap between isolated crystal clusters.

The high temperature was beneficial to the acceleration of crystal growth. However, high temperature alone did not effectively control the crystal orientation. The rapid evaporation caused by high temperature and the resulting local supersaturation and liquid flow provided a constant supply of calcium ions and phosphate ions to the activated substrate near the liquid level and promoted the crystal growth perpendicular to the substrate in a competitive manner. Both high temperature and evaporation played important roles in generating an enamel-like structure Methods of Using Compounds of the Subject Invention In certain embodiments, the FAP-LPAA composition can be applied to the enamel and/or dentin of a tooth of a subject. The FAP-LPAA can be bonded to enamel and/or dentin surface by dental adhesives.

In one embodiment, the subject is infected with *Streptococcus mutans* or any other bacteria known to be involved dental caries. In certain embodiments, the FAP-LPAA composition can be used to treat bacterial infections or prevent bacterial infections, particularly of the tooth or gums. In certain embodiments, the compositions of the subject invention can be used to reduce tooth decay caused by bacteria.

In certain embodiments, the FAP-LPAA sheet has comparable physicochemical property including, for example, mechanical properties to dental enamel and has excellent biocompatibility and antimicrobial properties, which can be indicated by dyeing bacteria to determine that FAP-LPAA killed the bacterial cells. Elastic modulus and hardness of the material can be measured by nanoindentation. Wear depth of the material can be measured by micro-scale abrasion tests. The biocompatibility of the material can be related to the safety of the materials, and the measurement of biocompatibility can indicate if the materials have potential toxicity to cells of the subject. The biocompatibility of the material is measured by cell counting, such as, for example, using the Cell Counting Kit-8 (CCK-8) and dyeing of cytoskeleton and cell nucleus. The FAP-LPAA can be administered to a subject, specifically on one or more teeth of a subject. The subject can have dental carries, tooth decay, enamel hypoplasia, tooth lesions, or bone-filling material. The FAP-LPAA can be applied directly to the tooth, bone, or enamel and bonded to said tooth, enamel, or bone via dental adhesives.

It should be understood that the examples and embodiments described herein are for illustrative purposes only and that various modifications or changes in light thereof will be suggested to persons skilled in the art and are to be included within the spirit and purview of this application. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

What is claimed is:

1. A method of synthesizing an enamel-like sheet, comprising:

i. providing a polymer plate;

ii. immersing the polymer plate in a polydopamine solution or other solutions that have phenolic hydroxyl groups at a concentration of about 2 mg/ml for at least 24 hours;

iii optionally, fixing plastic foams on the polydopamine-activated polymer plate to provide additional buoyance force for the polymer plate;

iv. placing the polymer plate in a calcification solution comprising low-molecular-weight polyacrylic acid (LPAA) and fluorapatite (FAP) Ca5(PO4)3F, ensuring a constant distance of about 3 mm from the polymer plate to the liquid surface of the calcification solution;

v. carrying out a mineralization process by incubating the system from step iv at about 70° C. for rapid evaporation and refreshing the evaporated solution by replenishing LPAA, FAP and water; and vi. dissolving the polymer plate with a solvent to obtain the enamel-like sheet, wherein the frequency of replenishing the solution can be determined by the evaporation rate of the solution, wherein the mineralization time depends on the needed thickness of the enamel like sheet, wherein the polymer plate is stable in water at 70° C. but can be dissolved by organic solvents selected from the group consisting of acetone and isoamyl acetate, wherein in the calcification solution, the concentration of fluorine ion is 0.1-10 mmol/L, and the concentration of LPAA is about 25 mg/L, wherein the LPAA has mass average molecular weight of 3,000.

2. The method of claim 1, wherein the calcification solution is replaced with new calcification solution about every 12 hours.

3. The method of claim 1, wherein the polymer plate is a polystyrene (PS) plate, a polypropylene plate, or a polymer plate.

4. The method of claim 1, wherein the fluorine ion is at a concentration of about 1.17 mmol/L.

5. A method of reducing bacteria in the mouth of a subject, the method comprising: contacting the mouth of the subject with an effective amount of the enamel-like sheet produced by the method of claim 1.

6. The method of claim 5, further comprising adhering the enamel-like sheet to the teeth, bone, and/or enamel of the subject.

7. A method of replacement of decayed enamel tooth lesion sites or bone comprising:

contacting one or more teeth or bone of a subject with an effective amount of the enamel-like sheet produced by the method of claim 1.

8. The method of claim 7, further comprising adhering the enamel-like sheet to the teeth, bone, and/or enamel of the subject.

9. A enamel-like composition produced by the method of claim 7.

10. The composition of claim 9, further comprising neutral buffered saline.

11. The composition of claim 9, wherein the composition is orally consumable.

12. The composition of claim 9, wherein the concentration of FAP is about 95%, and the concentration of LPAA is at about 5%.

* * * * *